United States Patent
Reddy et al.

[11] Patent Number: 6,054,587
[45] Date of Patent: Apr. 25, 2000

[54] INDOLE AND AZAINDOLE INHIBITORS OF FRUCTOSE-1,6-BISPHATASE

[75] Inventors: K. Raja Reddy, San Diego; Gerard R. Scarlato, La Jolla; Qun Dang, San Diego; Mark D. Erion, Del Mar; Srinivas Rao Kasibhatla; M. Rami Reddy, both of San Diego, all of Calif.

[73] Assignee: Metabasis Therapeutics, Inc., San Diego, Calif.

[21] Appl. No.: 09/036,328

[22] Filed: Mar. 6, 1998

Related U.S. Application Data

[60] Provisional application No. 60/040,624, Mar. 7, 1997.

[51] Int. Cl.$^7$ ........................................ C07F 9/24
[52] U.S. Cl. ........................................ 548/113
[58] Field of Search ........................................ 548/113

[56] References Cited

U.S. PATENT DOCUMENTS

| | | | |
|---|---|---|---|
| 3,931,206 | 1/1976 | Bowler et al. | 260/295 |
| 4,000,305 | 12/1976 | Bowler et al. | 424/274 |
| 4,968,790 | 11/1990 | DeVries et al. | 536/117 |
| 5,395,826 | 3/1995 | Naumann et al. | 514/107 |
| 5,498,617 | 3/1996 | Naumann et al. | 514/315 |
| 5,658,889 | 8/1997 | Gruber et al. | 514/43 |
| 5,661,174 | 8/1997 | Naumann et al. | 514/416 |

FOREIGN PATENT DOCUMENTS

| | | |
|---|---|---|
| 1324383 | 11/1993 | Canada . |
| 0 354 322 A2 | 2/1990 | European Pat. Off. . |
| 0 354 806 | 2/1990 | European Pat. Off. . |
| 0 449 196 A3 | 10/1991 | European Pat. Off. . |
| 0 620 227 A1 | 10/1994 | European Pat. Off. . |
| 0 427 799 B1 | 11/1994 | European Pat. Off. . |
| 28 55 659 | 7/1980 | Germany . |
| 5-97883 | 4/1993 | Japan . |
| 92/13864 | 8/1992 | WIPO . |
| 94/07867 | 4/1994 | WIPO . |
| 94/20508 | 9/1994 | WIPO . |
| 96/21644 | 7/1996 | WIPO . |

OTHER PUBLICATIONS

Garuti, R., Synthesis and Biological Evaluation of Some New Phosphonates, Pharmazie, 47, Dec. 1992.

Yoshino et al., "Organic phosphorus compounds. 2. Synthesis and coronary vasodilator activity of (Benzothiazolylbenzyl) phosphonate derivatives," *J. Med. Chem.* 32:1528–1532 (1989).

McNeil et al., J. Med. Chem. 106:7851 (1984).

Patent Abstracts of Japan, 17(442) (C–1097), Aug. 16, 1993 & JP 05 097883 A.

Shoji, et al., "Preparation of imidazo[1,2–a]pyridine derivatives as antihyperlipidemics and ischemia–reperfusion injury improvers and their intermediates as alpha–haloketone derivatives", Chemical Abstracts 118(5), Feb. 1, 1993.

*Primary Examiner*—Johann Richter
*Assistant Examiner*—Dominic Keating
*Attorney, Agent, or Firm*—Lyon & Lyon LLP

[57] ABSTRACT

Novel indole and azaindole compounds of the following structure and their use as fructose-1,6-bisphosphatase inhibitors is described:

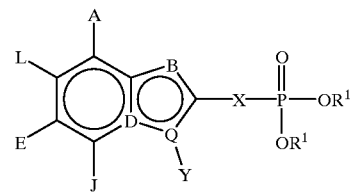

and pharmaceutically acceptable prodrugs and salts thereof.

47 Claims, 3 Drawing Sheets

*In Vitro* Inhibition of hIFBPase

INDOLE AND AZAINDOLE INHIBITORS OF FRUCTOSE-1,6-BISPHOSPHATASE

This application is a continuation in part of Provisional Application Ser. No. 60/040,629, filed Mar. 7, 1997, now abandoned.

FIELD OF THE INVENTION

This invention relates to novel indole and azaindole compounds that are inhibitors of Fructose-1,6-bisphosphatase at the AMP site. The invention also relates to the preparation and use of these indole and azaindole analogs in the treatment of diabetes, and other diseases where the inhibition of gluconeogenesis, control of blood glucose levels, reduction in glycogen stores, or reduction in insulin levels is beneficial.

BACKGROUND AND INTRODUCTION TO THE INVENTION

Diabetes mellitus (or diabetes) is one of the most prevalent diseases in the world today. Diabetes patients have been divided into two classes, namely type I or insulin-dependent diabetes mellitus and type II or non-insulin dependent diabetes mellitus (NIDDM). Non-insulin-dependent diabetes mellitus (NIDDM) accounts for approximately 90% of all diabetics and is estimated to affect 12–14 million adults in the U.S. alone (6.6% of the population). NIDDM is characterized by both fasting hyperglycemia and exaggerated postprandial increases in plasma glucose levels. NIDDM is associated with a variety of long-term complications, including microvascular diseases such as retinopathy, nephropathy and neuropathy, and macrovascular diseases such as coronary heart disease. Numerous studies in animal models demonstrate a causal relationship between long term complications and hyperglycemia. Recent results from the Diabetes Control and Complications Trial (DCCT) and the Stockholm Prospective Study demonstrate this relationship for the first time in man by showing that insulin-dependent diabetics with tighter glycemic control are at substantially lower risk for development and progression of these complications. Tighter control is also expected to benefit NIDDM patients.

Current therapies used to treat NIDDM patients entail both controlling lifestyle risk factors and pharmaceutical intervention. First-line therapy for NIDDM is typically a tightly-controlled regimen of diet and exercise since an overwhelming number of NIDDM patients are overweight or obese ($\approx$67%) and since weight loss can improve insulin secretion, insulin sensitivity and lead to normoglycemia. Normalization of blood glucose occurs in less than 30% of these patients due to poor compliance and poor response. Patients with hyperglycemia not controlled by diet alone are subsequently treated with oral hypoglycemics or insulin. Until recently, the sulfonylureas were the only class of oral hypoglycemic agents available for NIDDM. Treatment with sulfonylureas leads to effective blood glucose lowering in only 70% of patients and only 40% after 10 years of therapy. Patients that fail to respond to diet and sulfonylureas are subsequently treated with daily insulin injections to gain adequate glycemic control.

Although the sulfonylureas represent a major therapy for NIDDM patients, four factors limit their overall success. First, as mentioned above, a large segment of the NIDDM population do not respond adequately to sulfonylurea therapy (i.e. primary failures) or become resistant (i.e. secondary failures). This is particularly true in NIDDM patients with advanced NIDDM since these patients have severely impaired insulin secretion. Second, sulfonylurea therapy is associated with an increased risk of severe hypoglycemic episodes. Third, chronic hyperinsulinemia has been associated with increased cardiovascular disease although this relationship is considered controversial and unproven. Last, sulfonylureas are associated with weight gain, which leads to worsening of peripheral insulin sensitivity and thereby can accelerate the progression of the disease.

Recent results from the U.K. Diabetes prospective study also showed that patients undergoing maximal therapy of a sulfonylurea, metformin, or a combination of the two, were unable to maintain normal fasting glycemia over the six year period of the study. U.K. Prospective Diabetes Study 16. *Diabetes*, 1995, 44,1249–158. These results further illustrate the great need for alternative therapies. Three therapeutic strategies that could provide additional health benefits to NIDDM patients beyond the currently available therapies, include drugs that would: (i) prevent the onset of NIDDM; (ii) prevent diabetic complications by blocking detrimental events precipitated by chronic hyperglycemia; or (iii) normalize glucose levels or at least decrease glucose levels below the threshold reported for microvascular and macrovascular diseases.

Hyperglycemia in NIDDM is associated with two biochemical abnormalities, namely insulin resistance and impaired insulin secretion. The relative roles of these metabolic abnormalities in the pathogenesis of NIDDM has been the subject of numerous studies over the past several decades. Studies of offspring and siblings of NIDDM patients, mono- and dizygotic twins, and ethnic populations with high incidence of NIDDM (e.g. Pima Indians) strongly support the inheritable nature of the disease.

Despite the presence of insulin resistance and impaired insulin secretion, fasting blood glucose (FBG) levels remain normal in pre-diabetic patients due to a state of compensatory hyperinsulinemia. Eventually, however, insulin secretion is inadequate and fasting hyperglycemia ensues. With time insulin levels decline. Progression of the disease is characterized by increasing FBG levels and declining insulin levels.

Numerous clinical studies have attempted to define the primary defect that accounts for the progressive increase in FBG. Results from these studies indicate that excessive hepatic glucose output (HGO) is the primary reason for the elevation in FBG with a significant correlation found for HGO and FBG once FBG exceeds 140 mg/dL. Kolterman, et al., *J. Clin. Invest.* 1981, 68, 957; DeFronzo, *Diabetes* 1988, 37, 667.

HGO comprises glucose derived from breakdown of hepatic glycogen (glycogenolysis) and glucose synthesized from 3-carbon precursors (gluconeogenesis). A number of radioisotope studies and several studies using $^{13}$C-NMR spectroscopy have shown that gluconeogenesis contributes between 50–100% of the glucose produced by the liver in the postabsorptive state and that gluconeogenesis flux is excessive (2- to 3-fold) in NIDDM patients. Magnusson, et al. *J. Clin. Invest.* 1992, 90, 1323–1327; Rothman, et al., *Science* 1991, 254, 573–76; Consoli, et al. *Diabetes* 1989, 38, 550–557.

Gluconeogenesis from pyruvate is a highly regulated biosynthetic pathway requiring eleven enzymes (FIG. 1). Seven enzymes catalyze reversible reactions and are common to both gluconeogenesis and glycolysis. Four enzymes catalyze reactions unique to gluconeogenesis, namely pyruvate carboxylase, phosphoenolpyruvate carboxykinase, fructose-1,6-bisphosphatase and glucose-6-phosphatase. Overall flux through the pathway is controlled by the specific activities of these enzymes, the enzymes that catalyzed the corresponding steps in the glycolytic direction, and by substrate availability. Dietary factors (glucose, fat) and hormones (insulin, glucagon, glucocorticoids, epinephrine) coordinatively regulate enzyme activities in the gluconeogenesis and glycolysis pathways through gene expression and post-translational mechanisms.

Of the four enzymes specific to gluconeogenesis, fructose-1,6-bisphosphatase (hereinafter "FBPase") is the most suitable target for a gluconeogenesis inhibitor based on efficacy and safety considerations. Studies indicate that nature uses the FBPase/PFK cycle as a major control point (metabolic switch) responsible for determining whether metabolic flux proceeds in the direction of glycolysis or gluconeogenesis. Claus, et al., *Mechanisms of Insulin Action,* Belfrage, P. editor, pp.305–321, Elsevier Science 1992; Regen, et al. *J. Theor. Biol.,* 1984, 111, 635–658; Pilkis, et al. *Annu. Rev. Biochem,* 1988, 57, 755–783. FBPase is inhibited by fructose- 2,6-bisphosphate in the cell. Fructose-2,6-bisphosphate binds to the substrate site of the enzyme. AMP binds to an allosteric site on the enzyme.

Synthetic inhibitors of FBPase have also been reported. McNiel reported that fructose-2,6-bisphosphate analogs inhibit FBPase by binding to the substrate site, *J. Med. Chem.,* 1984, 106, 7851; U.S. Pat. No. 4,968,790 (1984). These compounds, however, were relatively weak and did not inhibit glucose production in hepatocytes presumably due to poor cell penetration.

Gruber reported that some nucleosides can lower blood glucose in the whole animal through inhibition of FBPase. These compounds exert their activity by first undergoing phosphorylation to the corresponding monophosphate. EP 0 427 799 B1.

Gruber et al. U.S. Pat. No. 5,658,889 described the use of inhibitors of the AMP site of FBPase to treat diabetes.

European Patent Application EP 0 449 196 A3 discloses certain ethyl phosphonates of indole compounds where X is C2–C3 alkylaminocarbonyl. The publication describes inhibitory activity of bone resorption. There is no suggestion that such compounds could be FBPase inhibitors or used to lower blood glucose.

European Patent Application EP 0 620 227 A1 published on Oct. 19, 1994 discloses certain heterocycles including indoles having a phosphonic acid where the X linker is alkylamino and alkylaminoalkyl. These compounds are said to inhibit bone resorption. There is no suggestion that the disclosed compounds were FBPase inhibitors or that they have blood glucose lowering activity.

Japanese Patent Application JP 5-97883 discloses certain indole phosphonates and phosphonate lower alkyl esters where X is a 1,4 linked alkylaryl group. The reference discloses their use for treating hyperlipemia and diabetes mellitus activity. There is no suggestion that such compounds would be FBPase inhibitors. Furthermore, such compounds would not be suitable FBPase inhibitors because a 1,4 linked 6-membered arylalkyl group would have too great a distance between the phosphorus and the indole ring for activity as an FBPase inhibitor at the AMP site.

SUMMARY OF THE INVENTION

Figure 1:
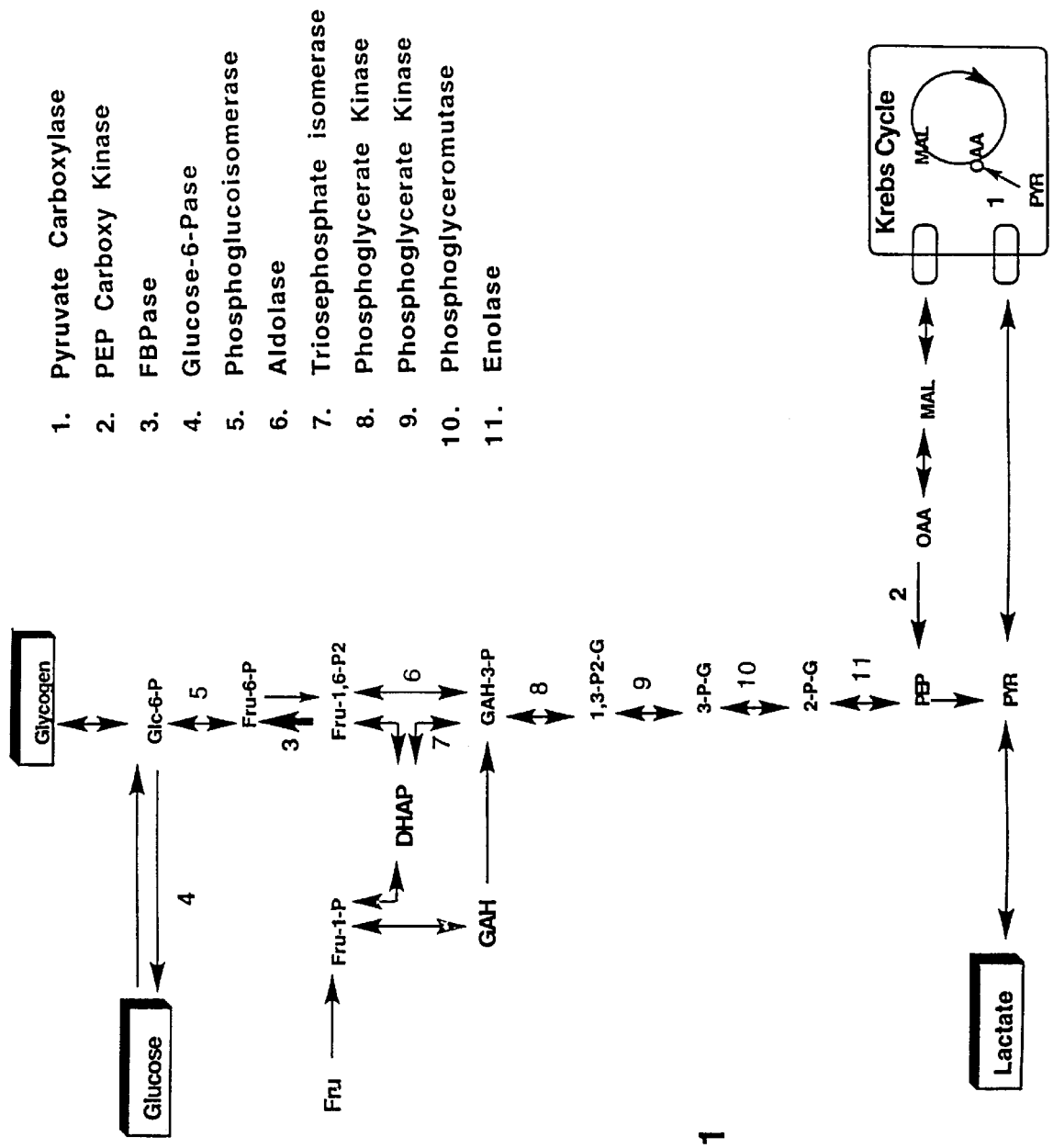
FIG. 1 is a scheme depicting the eleven enzymes of the gluconeogenesis pathway.

The present invention is directed towards novel indole compounds which bind to the AMP site and are potent FBPase inhibitors. In another aspect, the present invention is directed to the preparation of these novel indole compounds and to the in vitro and in vivo FBPase inhibitory activity of these compounds. Another aspect of the present invention is directed to the clinical use of the novel FBPase inhibitors as a method of treatment or prevention of diseases responsive to inhibition of gluconeogenesis and in diseases responsive to lowered blood glucose levels.

The compounds are also useful in treating or preventing excess glycogen storage diseases and insulin dependent diseases such as cardiovascular diseases including atherosclerosis.

The invention comprises the novel indole analogs as specified below in formula 1. Also included in the scope of the present invention are prodrugs of the compounds of formula 1.

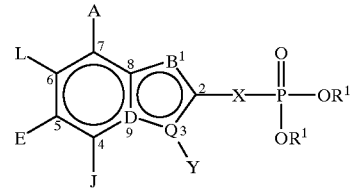

Formula 1

Since these compounds may have asymmetric centers, the present invention is directed not only to racemic mixtures of these compounds, but also to individual stereoisomers. The present invention also includes pharmaceutically acceptable and/or useful salts of the compounds of formula 1, including acid addition salts. The present inventions also encompass prodrugs of compounds of formula 1.

Definitions

In accordance with the present invention and as used herein, the following terms are defined with the following meanings, unless explicitly stated otherwise.

The term "aryl" refers to aromatic groups which have at least one ring having a conjugated pi electron system and includes carbocyclic aryl, heterocyclic aryl and biaryl groups, all of which may be optionally substituted.

Carbocyclic aryl groups are groups wherein the ring atoms on the aromatic ring are carbon atoms. Carbocyclic aryl groups include monocyclic carbocyclic aryl groups and polycyclic or fused compounds such as optionally substituted naphthyl groups.

Heterocyclic aryl groups are groups having from 1 to 4 heteroatoms as ring atoms in the aromatic ring and the remainder of the ring atoms being carbon atoms. Suitable heteroatoms include oxygen, sulfur, and nitrogen. Suitable heteroaryl groups include furanyl, thienyl, pyridyl, pyrrolyl, N-lower alkyl pyrrolyl, pyridyl-N-oxide, pyrimidyl, pyrazinyl, imidazolyl, and the like, all optionally substituted.

The term "biaryl" represents aryl groups containing more than one aromatic ring including both fused ring systems and aryl groups substituted with other aryl groups.

The term "alicyclic" means compounds which combine the properties of aliphatic and cyclic compounds and include but are not limited to aromatic, cycloalkyl and bridged cycloalkyl compounds. The cyclic compound includes heterocycles. Cyclohexenylethyl, cyclohexanylethyl, and norbornyl are suitable alicyclic groups. Such groups may be optionally substituted.

The term "optionally substituted" or "substituted" includes groups substituted by one to four substituents, independently selected from lower alkyl, lower aryl, lower aralkyl, lower alicyclic, hydroxy, lower alkoxy, lower aryloxy, perhaloalkoxy, aralkoxy, heteroaryl, heteroaryloxy, heteroarylalkyl, heteroaralkoxy, azido, amino, guanidino, halogen, lower alkylthio, oxa, ketone, carboxy esters, carboxyl, carboxamido, nitro, acyloxy, alkylamino, aminoalkyl, alkylaminoaryl, alkylaryl, alkylaminoalkyl, alkoxyaryl, arylamino, aralkylamino, phosphonate, sulfonate, carboxamidoalkylaryl, carboxamidoaryl, hydroxyalkyl, haloalkyl, alkylaminoalkylcarboxy, aminocarboxamidoalkyl, cyano, lower alkoxyalkyl, and lower perhaloalkyl.

The term "aralkyl" refers to an alkyl group substituted with an aryl group. Suitable aralkyl groups include benzyl, picolyl, and the like, and may be optionally substituted.

The term "lower" referred to herein in connection with organic radicals or compounds respectively defines such as with up to and including 10, preferably up to and including 6, and advantageously one to four carbon atoms. Such groups may be straight chain, branched, or cyclic.

The terms "arylamino" (a), and "aralkylamino" (b), respectively, refer to the group —NRR' wherein respectively, (a) R is aryl and R' is hydrogen, alkyl, aralkyl or aryl, and (b) R is aralkyl and R' is hydrogen or aralkyl, aryl, alkyl.

The term "acyl" refers to —C(O)R where R is alkyl and aryl.

The term "carboxy esters" refers to —C(O)OR where R is alkyl, aryl, aralkyl, and alicyclic, all optionally substituted.

The term "oxa" refers to =O in an alkyl group.

The term "alkylamino" refers to —NRR' where R and R' are independently selected from hydrogen or alkyl.

The term "carbonylamine" or "carbonylamino" refers to —CONR$_2$ where each R is independently hydrogen or alkyl.

The term "halogen" or "halo" refers to —F, —Cl, —Br and —I.

The term "oxyalkylamino" refers to —O-alk-NR—, where "alk" is an alkylene group and R is H or alkyl.

The term "alkylsulfonate" refers to the group -alk-S(O)$_2$—O— where "alk" is an alkylene group.

The term "alkylaminoalkylcarboxy" refers to the group -alk-NR-alk-C(O)—O— where "alk" is an alkylene group, and R is a H or lower alkyl.

The term "alkylaminocarbonyl" refers to the group -alk-NR—C(O)— where "alk" is an alkylene group, and R is a H or lower alkyl.

The term "oxyalkyl" refers to the group —O-alk- where "alk" is an alkylene group.

The term "alkylcarboxyalkyl" refers to the group -alk-C(O)—O-alkyl where each alk is independently an alkylene group.

The term "alkyl" refers to saturated aliphatic groups including straight-chain, branched chain and cyclic groups. Alkyl groups may be optionally substituted.

The term "bidentate" refers to an alkyl group that is attached by its terminal ends to the same atom to form a cyclic group. For example, propylene imine contains a bidentate propylene group.

The term "cyclic alkyl" refers to alkyl groups that are cyclic.

The term "heterocyclic" and "heterocyclic alkyl" refer to cyclic alkyl groups containing at least one heteroatom. Suitable heteroatoms include oxygen, sulfur, and nitrogen. Heterocyclic groups may be attached through a heteroatom or through a carbon atom in the ring.

The term "alkenyl" refers to unsaturated groups which contain at least one carbon-carbon double bond and includes straight-chain, branched-chain and cyclic groups. Alkene groups may be optionally substituted.

The term "alkynyl" refers to unsaturated groups which contain at least one carbon—carbon triple bond and includes straight-chain, branched-chain and cyclic groups. Alkyne groups may be optionally substituted.

The term "alkylene" refers to a divalent straight chain, branched chain or cyclic saturated aliphatic radical.

The term "acyloxy" refers to the ester group —O—C(O)R, where R is H, alkyl, alkenyl, alkynyl, aryl, aralkyl, or alicyclic.

The term "alkylaryl" refers to the group -alk-aryl- where "alk" is an alkylene group. "Lower alkylaryl" refers to such groups where alkylene is lower alkyl.

The term "alkylamino" refers to the group -alk-NR— wherein "alk" is an alkylene group.

The term "alkyl(carboxyl)" refers to carboxyl substituted off the alkyl chain. Similarly, "alkyl(hydroxy)", "alkyl (phosphonate)", and "alkyl(sulfonate)" refers to substituents off the alkyl chain.

The term "alkylaminoalkyl" refers to the group alk-NR-alk- wherein each "alk" is an independently selected alkylene, and R is H or lower alkyl. "Lower alkylaminoalkyl" refers to groups where each alkylene group is lower alkyl.

The term "alkylaminoaryl" refers to the group -alk-NR-aryl- wherein "alk" is an alkylene group. In "lower alkylaminoaryl", the alkylene group is lower alkyl.

The term "alkyloxyaryl" refers to an alkylene group substituted with an aryloxy group. In "lower alkyloxyaryl", the alkylene group is lower alkyl.

The term "alkylacylamino" refers to the group -alk-N—(COR)— wherein alk is alkylene and R is lower alkyl. In "lower alkylacylamino", the alkylene group is lower alkyl.

The term "alkoxyalkylaryl" refers to the group -alk-O-alk-aryl- wherein each "alk" is independently an alkylene group. "Lower aloxyalkylaryl" refers to such groups where the alkylene group is lower alkyl.

The term "alkylacylaminoalkyl refers to the group -alk-N—(COR)-alk- where each alk is an independently selected alkylene group. In "lower alkylacylaminoalkyl" the alkylene groups are lower alkyl.

The term "alkoxy" refers to the group -alk-O- wherein alk is an alkylene group.

The term "alkoxyalkyl" refers to the group -alk-O-alk- wherein each alk is an independently selected alkylene group. In "lower alkoxyalkyl", each alkylene is lower alkyl.

The term "alkylthio" refers to the group -alk-S— wherein alk is alkylene group.

The term "alkylthioalkyl" refers to the group -alk-S-alk- wherein each alk is an independently selected alkylene group. In "lower alkylthioalkyl" each alkylene is lower alkylene.

The term "aralkylamino" refers to an amine substituted with an aralkyl group.

The term "alkylcarboxamido" refers to the group -alk-C (O)N(R)— wherein alk is an alkylene group and R is H or lower alkyl.

The term "alkylcarboxamidoalkyl" refers to the group alk-C(O)N(R)-alk- wherein each alk is an independently selected alkylene group and R is lower alkyl. In "lower alkylcarboxamidoalkyl" each alkylene is lower alkyl.

The term "alkylcarboxamidoalkylaryl" refers to the group -alk$_1$-C(O)—NH-alk$_2$Ar— wherein alk$_1$ and alk$_2$ are independently selected alkylene groups and alk$_2$ is substituted with an aryl group, Ar. In "lower alkylcarboxamidoalkylaryl", each alkylene is lower alkyl.

The term "heteroalicyclic" refers to an alicyclic group having 1 to 4 heteroatoms selected from nitrogen, sulfur, phosphorus and oxygen.

The term "aminocarboxamidoalkyl" refers to the group —NH—C(O)—N(R)—R wherein each R is an independently selected alkyl group. "Lower aminocaboxamidoalkyl" refers to such groups wherein each R is lower alkyl.

The term "heteroarylalkyl" refers to an alkyl group substituted with a heteroaryl group.

The term "perhalo" refers to groups wherein every C—H bond has been replaced with a C-halo bond on an aliphatic or aryl group. Suitable perhaloalkyl groups include —CF$_3$ and —CFCl$_2$.

The term "guanidine" refers to both —NR—C(NR)—NR$_2$ as well as —N=C(NR$_2$)$_2$ where each R group is independently selected from the group of —H, alkyl, alkenyl, alkynyl, aryl, and alicyclic, all optionally substituted.

The term "amidine" refers to —C(NR)—NR$_2$ where each R group is independently selected from the group of —H, alkyl, alkenyl, alkynyl, aryl, and alicyclic, all optionally substituted.

The term "pharmaceutically acceptable salt" includes salts of compounds of formula 1 and its prodrugs derived from the combination of a compound of this invention and an organic or inorganic acid or base.

The term "prodrug" as used herein refers to any compound that when administered to a biological system generates the "drug" substance either as a result of spontaneous chemical reaction(s) or by enzyme catalyzed or metabolic reaction(s). Reference is made to various prodrugs such as acyl esters, carbonates, and carbamates, included herein. The groups illustrated are exemplary, not exhaustive, and one skilled in the art could prepare other known varieties of prodrugs. Such prodrugs of the compounds of formula 1, fall within the scope of the present invention.

The term "prodrug ester" as employed herein includes, but is not limited to, the following groups and combinations of these groups:

[1] Acyloxyalkyl esters which are well described in the literature (Farquhar et al., *J. Pharm. Sci.* 72, 324–325 (1983)) and are represented by formula A

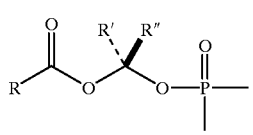

Formula A wherein R, R', and R" are independently H, alkyl, aryl, alkylaryl, and alicyclic; (see WO 90/08155; WO 90/10636).

[2] Other acyloxyalkyl esters are possible in which an alicyclic ring is formed such as shown in formula B. These esters have been shown to generate phosphorus-containing nucleotides inside cells through a postulated sequence of reactions beginning with deesterification and followed by a series of elimination reactions (e.g. Freed et al., *Biochem. Pharm.* 38: 3193–3198 (1989)).

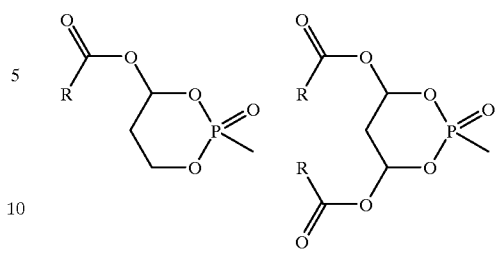

Formula B wherein R is —H, alkyl, aryl, alkylaryl, alkoxy, aryloxy, alkylthio, arylthio, alkylamino, arylamino, cycloalkyl, or alicyclic.

[3] Another class of these double esters known as alkyloxycarbonyloxymethyl esters, as shown in formula A, where R is alkoxy, aryloxy, alkylthio, arylthio, alkylamino, and arylamino; R', and R" are independently H, alkyl, aryl, alkylaryl, and alicyclic, have been studied in the area of β-lactam antibiotics (Tatsuo Nishimura et al. *J. Antibiotics*, 1987, 40(1), 81–90; for a review see Ferres, H., *Drugs of Today*, 1983,19, 499. ). More recently Cathy, M. S., et al. (Abstract from AAPS Western Regional Meeting, April, 1997) showed that these alkyloxycarbonyloxymethyl ester prodrugs on (9-[(R)-2-phosphonomethoxy)propyl]adenine (PMPA) are bioavailable up to 30% in dogs.

[4] Aryl esters have also been used as phosphonate prodrugs (e.g. Erion, DeLambert et al., *J. Med. Chem.* 37: 498, 1994; Serafinowska et al., *J. Med. Chem.* 38: 1372, 1995). Phenyl as well as mono and poly-substituted phenyl proesters have generated the parent phosphonic acid in studies conducted in animals and in man (Formula C). Another approach has been described where Y is a carboxylic ester ortho to the phosphate. Khamnei and Torrence, *J. Med. Chem.*; 39:4109–4115 (1996).

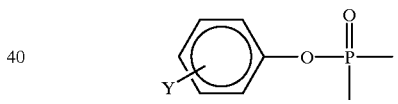

Formula C wherein Y is H, alkyl, aryl, alkylaryl, alkoxy, acetoxy, halogen, amino, alkoxycarbonyl, hydroxy, cyano, alkylamino, and alicyclic.

[5] Benzyl esters have also been reported to generate the parent phosphonic acid. In some cases, using substituents at the para-position can accelerate the hydrolysis. Benzyl analogs with 4-acyloxy or 4-alkyloxy group [Formula D, X=H, OR or O(CO)R or O(CO)OR] can generate the 4-hydroxy compound more readily through the action of enzymes, e.g. oxidases, esterases, etc. Examples of this class of prodrugs are described in Mitchell et al., *J. Chem. Soc. Perkin Trans. I* 2345 (1992); Brook, et al. WO 91/19721.

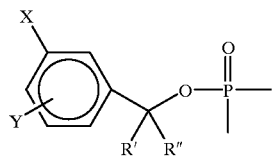

Formula D wherein X and Y are independently H, alkyl, aryl, alkylaryl, alkoxy, acetoxy, hydroxy, cyano, nitro, perhaloalkyl, halo, or alkyloxycarbonyl; and R' and R" are independently H, alkyl, aryl, alkylaryl, halogen, and alicyclic.

[6] Thio-containing phosphonate proesters have been described that are useful in the delivery of FBPase inhibitors to hepatocytes. These proesters contain a protected thioethyl moiety as shown in formula E. One or more of the oxygens of the phosphonate can be esterified. Since the mechanism that results in de-esterification requires the generation of a free thiolate, a variety of thiol protecting groups are possible. For example, the disulfide is reduced by a reductase-mediated process (Puech et al., *Antiviral Res.*, 22: 155–174 (1993)). Thioesters will also generate free thiolates after esterase-mediated hydrolysis. Benzaria, et al., *J. Med. Chem.*, 39:4958 (1996). Cyclic analogs are also possible and were shown to liberate phosphonate in isolated rat hepatocytes. The cyclic disulfide shown below has not been previously described and is novel.

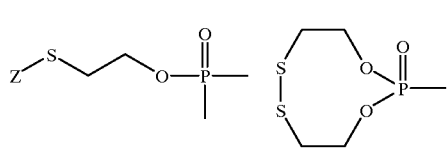

Formula E wherein Z is alkylcarbonyl, alkoxycarbonyl, arylcarbonyl, aryloxycarbonyl, or alkylthio.

Other examples of suitable prodrugs include proester classes exemplified by Biller and Magnin (U.S. Pat. No. 5,157,027); Serafinowska et al. (*J. Med. Chem.* 38, 1372 (1995)); Starrett et al. (*J. Med. Chem.* 37,1857 (1994)); Martin et al. *J. Pharm. Sci.* 76, 180 (1987); Alexander et al., *Collect. Czech. Chem. Comnun*, 59, 1853 (1994)); and EPO patent application 0 632 048 A1. Some of the structural classes described are optionally substituted, including fused lactones attached at the omega position and optionally substituted 2-oxo-1,3-dioxolenes attached through a methylene to the phosphorus oxygen such as:

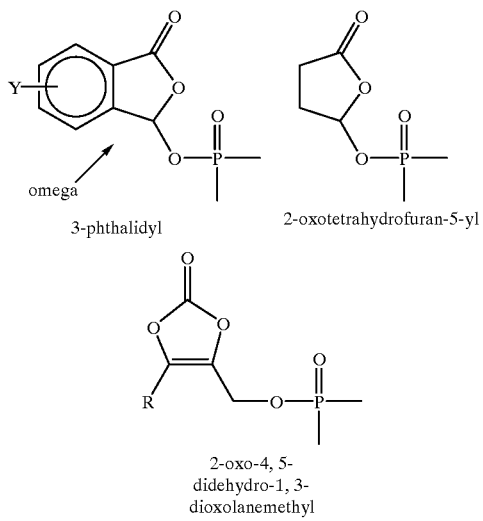

3-phthalidyl  2-oxotetrahydrofuran-5-yl 2-oxo-4, 5-didehydro-1, 3-dioxolanemethyl wherein R is —H, alkyl, cycloalkyl, or alicyclic; and
wherein Y is —H, alkyl, aryl, alkylaryl, cyano, alkoxy, acetoxy, halogen, amino, alkylamino, alicyclic, and alkoxycarbonyl.

[7] Propyl phosphonate proesters can also be used to deliver FBPase inhibitors into hepatocytes. These proesters may contain a hydroxyl and hydroxyl group derivatives at the 3-position of the propyl group as shown in formula F. The R and X groups can form a cyclic ring system as shown in formula F. One or more of the oxygens of the phosphonate can be esterified.

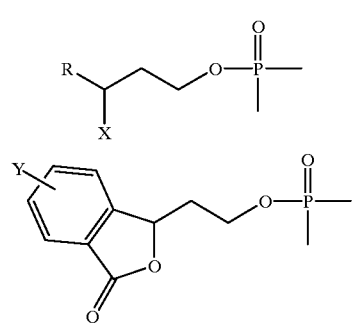

Formula F wherein R is alkyl, aryl, heteroaryl;
X is hydrogen, alkylcarbonyloxy, alkyloxycarbonyloxy; and
Y is alkyl, aryl, heteroaryl, alkoxy, alkylamino, alkylthio, halogen, hydrogen, hydroxy, acetoxy, amino.

[8] The cyclic propyl phosphonate esters as in Formula G are shown to activate to phosphonic acids. The activation of prodrug can be mechanistically explained by in vivo oxidation and elimination steps. These prodrugs inhibit glucose production in isolated rat hepatocytes and are also shown to deliver FBPase inhibitors to the liver following oral administration.

Formula G wherein
V and W are independently selected from the group consisting of hydrogen, aryl, substituted aryl, heteroaryl, substituted heteroaryl, 1-alkenyl, 1-alkynyl, and —$R^9$; or
together V and Z are connected to form a cyclic group containing 3–5 atoms, optionally 1 heteroatom, substituted with hydroxy, acyloxy, alkoxycarboxy, or aryloxycarboxy attached to a carbon atom that is three atoms from an oxygen attached to the phosphorus; or
together V and W are connected to form a cyclic group containing 3 carbon atoms substituted with hydroxy, acyloxy, alkoxycarboxy, alkylthiocarboxy, hydroxymethyl, and aryloxycarboxy attached to a carbon atom that is three atoms from an oxygen attached to the phosphorus;
Z is selected from the group consisting of —$CH_2OH$, —$CH_2OCOR^3$, —$CH_2OC(O)SR^3$, —$CH_2OCO_2R^3$, —$SR^3$, —$S(O)R^3$, —$CH_2N_3$, —$CH_2NR^2{}_2$, —$CH_2Ar$, —$CH(Ar)OH$, —$CH(CH=CR^2R^2)OH$, —$CH(C\equiv CR^2)OH$, and —$R^2$;
with the provisos that:
a) V, Z, W are not all —H; and
b) when Z is —$R^2$, then at least one of V and W is not —H or —$R^9$;

$R^2$ is selected from the group consisting of $R^3$ and —H;

$R^3$ is selected from the group consisting of alkyl, aryl, alicyclic, and aralkyl; and $R^9$ is selected from the group consisting of alkyl, aralkyl, and alicyclic.

[9] Phosphoramidate derivatives have been explored as potential phosphonate prodrugs (e.g. McGuigan et al., *Antiviral Res.* 1990, 14: 345; 1991, 15: 255. Serafinowska et al., *J. Med. Chem.*, 1995, 38, 1372). Most phosphoramidates are unstable under aqueous acidic conditions and are hydrolyzed to the corresponding phosphonic acids. Cyclic phosphoramidates have also been studied as phosphonate prodrugs because of their potential for greater stability compared to non cyclic phosphoramidates (e.g. Starrett et al., *J. Med. Chem.*, 1994, 37: 1857).

Other prodrugs are possible based on literature reports such as substituted ethyls for example, bis(trichloroethyl) esters as disclosed by McGuigan, et al. *Bioorg Med. Chem. Lett.*, 3:1207–1210 (1993), and the phenyl and benzyl combined nucleotide esters reported by Meier, C. et al. *Bioorg. Med. Chem. Lett.*, 7:99–104 (1997).

X group nomenclature as used herein in formula 1 describes the group attached to the phosphonate and ends with the group attached to the 2-position of the indole ring. For example, when X is alkylamino, the following structure is intended:

(ring)-NR-alk-P(O)(OR$^1$)$_2$

Y group nomenclature likewise ends with the group attached to the ring.

DETAILED DESCRIPTION OF THE INVENTION

Preferred compounds of the present invention are inhibitors of the AMP site of FBPase of the following formula (1).

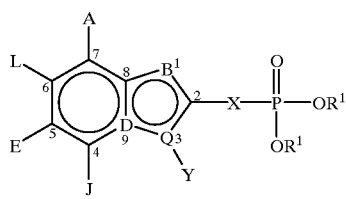

wherein:

B is selected from the group consisting of —NH—, —N= and —CH=;

D is selected from the group consisting of

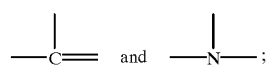

Q is selected from the group consisting of —C= and —N— with the proviso that when B is —NH— then Q is —C= and D is

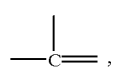

when B is —CH= then Q is —N— and D is

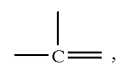

when B is —N=, then D is

and Q is —C=;

A, E, and L are selected from the group consisting of —NR$^8$$_2$, —NO$_2$, —H, —OR$^7$, —SR$^7$, —C(O)NR$^4$$_2$, halo, —COR$^{11}$, —SO$_2$R$^3$, guanidine, amidine, —NHSO$_2$R$^5$, —SO$_2$NR$^4$$_2$, —CN, sulfoxide, perhaloacyl, perhaloalkyl, perhaloalkoxy, C1–C5 alkyl, C2–C5 alkenyl, C2–C5 alkynyl, and lower alicyclic, or together A and L form a cyclic group, or together L and E form a cyclic group, or together E and J form a cyclic group including aryl, cyclic alkyl, and heterocyclic;

J is selected from the group consisting of —NR$^8$$_2$, —NO$_2$, —H, —OR$^7$, —SR$^7$, —C(O)NR$^4$$_2$, halo, —C(O)R$^{11}$, —CN, sulfonyl, sulfoxide, perhaloalkyl, hydroxyalkyl, perhaloalkoxy, alkyl, haloalkyl, aminoalkyl, alkenyl, alkynyl, alicyclic, aryl, and aralkyl, or together with Y forms a cyclic group including aryl, cyclic alkyl and heterocyclic alkyl;

X is selected from the group consisting of alkylamino, alkyl(hydroxy), alkyl(carboxyl), alkyl(phosphonate), alkyl, alkenyl, alkynyl, alkyl(sulfonate), aryl, carbonylalkyl, 1,1-dihaloalkyl, aminocarbonylamino, alkylaminoalkyl, alkoxyalkyl, alkylthioalkyl, alkylthio, alkylaminocarbonyl, alkylcarbonylamino, alicyclic, aralkyl, and alkylaryl, all optionally substituted; or together with Y forms a cyclic group including aryl, cyclic alkyl, and heterocyclic;

Y is selected from the group consisting of —H, alkyl, alkenyl, alkynyl, aryl, alicyclic, aralkyl, aryloxyalkyl, alkoxyalkyl, —C(O)R$^3$, —S(O)$_2$R$^3$, —C(O)—OR$^3$, —CONHR$^3$, —NR$^2$$_2$, and —OR$^3$, all except H are optionally substituted; or together with X forms a cyclic group including aryl, cyclic alkyl, and heterocyclic;

R$^1$ is independently selected from the group consisting of —H, alkyl, aryl, alicyclic where the cyclic moiety contains a carbonate or thiocarbonate, —C(R$^2$)$_2$-aryl, alkylaryl, —C(R$^2$)$_2$OC(O)NR$^2$$_2$, —NR$^2$—C(O)—R$^3$, —C(R$^2$)$_2$—OC(O)R$^3$, C(R$^2$)$_2$—O—C(O)OR$^3$, —C(R$^2$)$_2$OC(O)SR$^3$, alkyl-S—C(O)R$^3$, alkyl-S—S-alkylhydroxy, and alkyl-S—S—S-alkylhydroxy, or together R$^1$ and R$^1$ are -alkyl-S—S-alkyl to form a cyclic group, or together R$^1$ and R$^1$ are

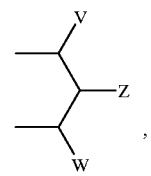

wherein

V and W are independently selected from the group consisting of hydrogen, aryl, substituted aryl, heteroaryl, substituted heteroaryl, 1-alkenyl, 1-alkynyl, and —R$^9$; or together V and Z are connected to form a cyclic group containing 3–5 atoms, optionally 1 heteroatom, substituted with hydroxy, acyloxy, alkoxycarboxy, or aryloxycarboxy attached to a carbon atom that is three atoms from an oxygen attached to the phosphorus; or together V and W are connected to form a cyclic group containing 3 carbon atoms substituted with hydroxy, acyloxy, alkoxycarboxy, alkylthiocarboxy, hydroxymethyl, and aryloxycarboxy attached to a carbon atom that is three atoms from an oxygen attached to the phosphorus;

Z is selected from the group consisting of —CH$_2$OH, —CH$_2$OCOR$^3$, —CH$_2$OC(O)SR$^3$, —CH$_2$OCO$_2$R$^3$, —SR$^3$, —S(O)R$^3$, —CH$_2$N$_3$, —CH$_2$NR$^2{}_2$, —CH$_2$Ar, —CH(Ar)OH, —CH(CH=CR$^2$R$^2$)OH, —CH(C≡CR$^2$)OH, and —R$^2$;

with the provisos that:

a) V, Z, W are not all —H; and b) when Z is —R$^2$, then at least one of V and W is not —H or —R$^9$;

R$^2$ is selected from the group consisting of R$^3$ and —H;

R$^3$ is selected from the group consisting of alkyl, aryl, alicyclic, and aralkyl;

R$^4$ is independently selected from the group consisting of —H, lower alkyl, lower alicyclic, lower aralkyl, and lower aryl;

R$^5$ is selected from the group consisting of lower alkyl, lower aryl, lower aralkyl, and lower alicyclic;

R$^6$ is independently selected from the group consisting of —H, and lower alkyl;

R$^7$ is independently selected from the group consisting of —H, lower alkyl lower alicyclic, lower aralkyl, lower aryl, and —C(O)R$^{10}$;

R$^8$ is independently selected from the group consisting of —H, lower alkyl, lower aralkyl, lower aryl, lower alicyclic, —C(O)R$^{10}$, or together they form a bidentate alkyl;

R$^9$ is selected from the group consisting of alkyl, aralkyl, and alicyclic;

R$^{10}$ is selected from the group consisting of —H, lower alkyl, —NH$_2$, lower aryl, and lower perhaloalkyl;

R$^{11}$ is selected from the group consisting of alkyl, aryl, —OH, —NH$_2$ and —OR$^3$; and pharmaceutically acceptable prodrugs and salts thereof; with the provisos that:

a) R$^1$ is not a lower alkyl of 1–4 carbon atoms;

b) X is not alkylamine and alkylaminoalkyl substituted with phosphonic esters or acids;

c) A, L, E, J, Y, and X together may only form 0–2 cyclic groups; and d) X is not aryl and alkylaryl linked 1,4 through a 6-membered aromatic ring.

Preferred compounds for the method of use claims are inhibitors of the AMP site of FBPase of the following formula (1):

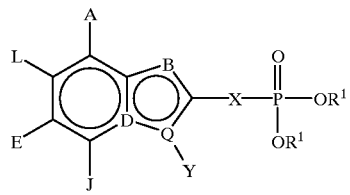

wherein:

B is selected from the group consisting of —NH—, —N= and —CH=;

D is selected from the group consisting of

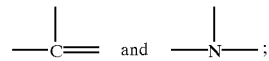

Q is selected from the group consisting of —C= and —N— with the proviso that when B is —NH— then Q is —C= and D is

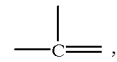

when B is —CH= then Q is —N— and D is

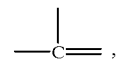

when B is —N=, then D is

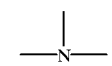

and Q is —C=;

A, E, and L are selected from the group consisting of —NR$^8{}_2$, —NO$_2$, —H, —OR$^7$, —SR$^7$, —C(O)NR$^4{}_2$, halo, —COR$^{11}$, —SO$_2$R$^3$, guanidine, amidine, —NHSO$_2$R$^5$, —SO$_2$NR$^4{}_2$, —CN, sulfoxide, perhaloacyl, perhaloalkyl, perhaloalkoxy, C1–C5 alkyl, C2–C5 alkenyl, C2–C5 alkynyl, and lower alicyclic, or together A and L form a cyclic group, or together L and E form a cyclic group, or together E and J form a cyclic group including aryl, cyclic alkyl, and heterocyclic;

J is selected from the group consisting of —NR$^8{}_2$, —NO$_2$, —H, —OR$^7$, —SR$^7$, —C(O)NR$^4{}_2$, halo, —C(O)R$^{11}$, —CN, sulfonyl, sulfoxide, perhaloalkyl, hydroxyalkyl, perhaloalkoxy, alkyl, haloalkyl, aminoalkyl, alkenyl, alkynyl, alicyclic, aryl, and aralkyl, or together with Y forms a cyclic group including aryl, cyclic alkyl and heterocyclic alkyl;

X is selected from the group consisting of alkylamino, alkyl(hydroxy), alkyl(carboxyl), alkyl(phosphonate), alkyl, alkenyl, alkynyl, alkyl(sulfonate), aryl, carbonylalkyl, 1,1-dihaloalkyl, aminocarbonylamino, alkylaminoalkyl, alkoxyalkyl, alkylthioalkyl, alkylthio, alkylaminocarbonyl, alkylcarbonylamino, alicyclic, aralkyl, and alkylaryl, all optionally substituted; or together with Y forms a cyclic group including aryl, cyclic alkyl, and heterocyclic;

Y is selected from the group consisting of —H, alkyl, alkenyl, alkynyl, aryl, alicyclic, aralkyl, aryloxyalkyl, alkoxyalkyl, —C(O)R³, —S(O)₂R³, —C(O)—OR³, CONHR³, —NR²₂, and —OR³, all except H are optionally substituted; or together with X forms a cyclic group including aryl, cyclic alkyl, and heterocyclic;

R is independently selected from the group consisting of —H, alkyl, aryl, alicyclic where the cyclic moiety contains a carbonate or thiocarbonate, —C(R²)₂-aryl, alkylaryl, —C(R²)₂OC(O)NR²₂, —NR²—C(O)—R³, —C(R²)₂—OC(O)R³, C(R²)₂—O—C(O)OR³, —C(R²)₂OC(O)SR³, alkyl-S—C(O)R³, alkyl-S—S-alkylhydroxy, and alkyl-S—S—S-alkylhydroxy, or together R¹ and R¹ are -alkyl-S—S-alkyl to form a cyclic group, or together R¹ and R¹ are

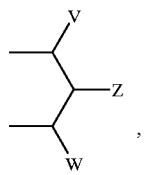

wherein

V and W are independently selected from the group consisting of hydrogen, aryl, substituted aryl, heteroaryl, substituted heteroaryl, 1-alkenyl, 1-alkynyl, and —R⁹; or together V and Z are connected to form a cyclic group containing 3–5 atoms, optionally 1 heteroatom, substituted with hydroxy, acyloxy, alkoxycarboxy, or aryloxycarboxy attached to a carbon atom that is three atoms from an oxygen attached to the phosphorus; or together V and W are connected to form a cyclic group containing 3 carbon atoms substituted with hydroxy, acyloxy, alkoxycarboxy, alkylthiocarboxy, hydroxymethyl, and aryloxycarboxy attached to a carbon atom that is three atoms from an oxygen attached to the phosphorus;

Z is selected from the group consisting of —CH₂OH, —CH₂OCOR³, —CH₂OC(O)SR³, —CH₂OCO₂R³, —SR³, —S(O)R³, —CH₂N₃, —CH₂NR²₂, —CH₂Ar, —CH(Ar)OH, —CH(CH=CR²R²)OH, —CH(C≡CR²)OH, and —R²;

with the provisos that:
a) V, Z, W are not all —H; and
b) when Z is —R², then at least one of V and W is not —H or —R⁹;

R² is selected from the group consisting of R³ and —H;
R³ is selected from the group consisting of alkyl, aryl, alicyclic, and aralkyl;
R⁴ is independently selected from the group consisting of —H, lower alkyl, lower alicyclic, lower aralkyl, and lower aryl;
R⁵ is selected from the group consisting of lower alkyl, lower aryl, lower aralkyl, and lower alicyclic;
R⁶ is independently selected from the group consisting of —H, and lower alkyl;
R⁷ is independently selected from the group consisting of —H, lower alkyl, lower alicyclic, lower aralkyl, lower aryl, and —C(O)R¹⁰;
R' is independently selected from the group consisting of —H, lower alkyl, lower aralkyl, lower aryl, lower alicyclic, —C(O)R¹⁰, or together they form a bidentate alkyl;

R⁹ is selected from the group consisting of alkyl, aralkyl, and alicyclic;
R¹⁰ is selected from the group consisting of —H, lower alkyl, —NH₂, lower aryl, and lower perhaloalkyl;
R¹¹ is selected from the group consisting of alkyl, aryl, —OH, —NH₂ and —OR³; and pharmaceutically acceptable prodrugs and salts thereof.

Preferred Compounds of Formula 1

Suitable alkyl groups include groups having from 1 to about 20 carbon atoms. Suitable aryl groups include groups having from 1 to about 20 carbon atoms. Suitable aralkyl groups include groups having from 2 to about 21 carbon atoms. Suitable acyloxy groups include groups having from 1 to about 20 carbon atoms. Suitable alkylene groups include groups having from 1 to about 20 carbon atoms. Suitable alicyclic groups include groups having 3 to about 20 carbon atoms. Suitable heteroaryl groups include groups having from 1 to about 20 carbon atoms and from 1 to 5 heteroatoms, preferably independently selected from nitrogen, oxygen, phosphorous, and sulfur. Suitable heteroalicyclic groups include groups having from 2 to about twenty carbon atoms and from 1 to 5 heteroatoms, preferably independently selected from nitrogen, oxygen, phosphorous, and sulfur.

Preferred A, L, and E groups include —H, —NR⁸₂, —NO₂, hydroxy, halogen, —OR⁷, alkylaminocarbonyl, —SR⁷, lower perhaloalkyl, and C1–C5 alkyl, or together E and J form a cyclic group. Such a cyclic group may be aromatic or cyclic alkyl, and may be optionally substituted. Suitable aromatic groups include thiazole. Particularly preferred A, L and E groups are —NR⁸₂, —H, hydroxy, halogen, lower alkoxy, lower perhaloalkyl, and lower alkyl.

Preferred A groups include —NR⁸₂, lower alkyl, —H, halogen, and lower perhaloalkyl.

Preferred L and E groups include —H, lower alkoxy, lower alkyl, and halogen.

Preferred J groups include -H, halogen, lower alkyl, lower hydroxyalkyl, —NR⁸₂, lower R⁸₂N-alkyl, lower haloalkyl, lower perhaloalkyl, lower alkenyl, lower alkynyl, lower aryl, heterocyclic, and alicyclic or together with Y forms a cyclic group. Such a cyclic group may be aromatic or cyclic alkyl, and may be optionally substituted. Particularly preferred J groups —H, halogen, lower alkyl, lower hydroxyalkyl, —NR⁸₂, lower R⁸₂N-alkyl, lower haloalkyl, lower alkenyl, alicyclic, and aryl.

Preferred X groups include alkyl, alkynyl, alkoxyalkyl, alkylthio, aryl, alkylaminocarbonyl, alkylcarbonylamino, 1,1-dihaloalkyl, carbonylalkyl, alkyl(OH), and alkyl (sulfonate). Particularly preferred is 1,1-dihaloalkyl, alkyl (sulfonate), alkylaminocarbonyl, alkoxyalkyl, and heteroaryl. Such compounds that are especially preferred are heteroaryl, alkylaminocarbonyl, and alkoxyalkyl. Most preferred is methylaminocarbonyl, methoxymethyl, and furanyl.

In one preferred aspect, X is not (C2–C3 alkyl) aminocarbonyl.

In one preferred aspect, when X is alkyl and alkene substituted with a phosphonic acid or ester, then A is —N(R")₂ and Y is not —H. In another preferred aspect, X is not substituted with a phosphonic acid or ester.

Preferred Y groups include —H, alkyl, aryl, aralkyl, and alicyclic, all except —H may be optionally substituted. Particularly preferred Y groups include lower alkyl, and alicyclic.

Preferred $R^1$ groups include —H, alkyl, aryl, alicyclic where the cyclic moiety contains a carbonate or thiocarbonate, optionally substituted phenyl, optionally substituted benzyl, optionally substituted alkylaryl, —C($R^2$)$_2$OC(O)$R^3$, C($R^2$)$_2$—O—C(O)O$R^3$, —C($R^2$)$_2$—OC(O)S$R^3$, -alkyl-S—C(O) $R^3$, alkyl-S—S-alkylhydroxyl, and -alkyl-S—S—S-alkylhydroxy, or together $R^1$ and $R^1$ are alkyl-S—S-alkyl to form a cyclic group, or $R^1$ and $R^1$ together are

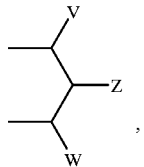

wherein

V and W are independently selected from the group consisting of hydrogen, aryl, substituted aryl, heteroaryl, substituted heteroaryl, 1-alkenyl, 1-alkynyl, and —$R^9$; or together V and Z are connected to form a cyclic group containing 3–5 atoms, optionally 1 heteroatom, substituted with hydroxy, acyloxy, alkoxycarboxy, or aryloxycarboxy attached to a carbon atom that is three atoms from an oxygen attached to the phosphorus; or together V and W are connected to form a cyclic group containing 3 carbon atoms substituted with hydroxy, acyloxy, alkoxycarboxy, alkylthiocarboxy, hydroxymethyl, and aryloxycarboxy attached to a carbon atom that is three atoms from an oxygen attached to the phosphorus;

Z is selected from the group consisting of —CH$_2$OH, —CH$_2$OCO$R^3$, —CH$_2$OC(O)S$R^3$, —CH$_2$OCO$_2R^3$, —S$R^3$, —S(O)$R^3$, —CH$_2$N$_3$, —CH$_2$N$R^2{}_2$, —CH$_2$Ar, —CH(Ar)OH, —CH(CH=C$R^2R^2$)OH, —CH(C≡C$R^2$)OH, and —$R^2$;

with the provisos that:
a) V, Z, W are not all —H; and
b) when Z is —$R^2$, then at least one of V and W is not —H or —$R^9$;

$R^2$ is selected from the group consisting of $R^3$ and —H;

$R^3$ is selected from the group consisting of alkyl, aryl, alicyclic, and aralkyl; and $R^9$ is selected from the group consisting of alkyl, aralkyl, and alicyclic.

Preferred such $R^1$ groups include optionally substituted phenyl, optionally substituted benzyl, —H, and —C($R^2$)$_2$OC(O)$R^3$. Also preferred are such groups where at least one $R^1$ is aryl or —C($R^2$)$_2$ aryl. Particularly preferred is H. Also preferred is when at least one $R^1$ is alkyl, preferably greater than 4 carbon atoms. Another preferred aspect is when at least one $R^1$ is —C($R^2$)$_2$—OC(O)$R^3$, —C($R^2$)$_2$—OC(O)OH$^3$, —C($R^2$)$_2$—OC(O)S$R^3$. Also particularly preferred is when $R^1$ and $R^1$ together are optionally substituted, including fused, lactones attached at the omega position or are optionally substituted 2-oxo-1,3-dioxolenes attached through a methylene to the phosphorus oxygen. Also preferred is when at least one $R^1$ is -alkyl-S—S-alkylhydroxyl, -alkyl-S—C(O)$R^3$, and -alkyl-S—S—S-alkylhydroxy, or together RH and $R^1$ are -alkyl-S—S-alkyl- to form a cyclic group. Also preferred is where $R^1$ and $R^1$ together are

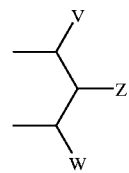

to form a cyclic group,

V and W are independently selected from the group consisting of hydrogen, aryl, substituted aryl, heteroaryl, substituted heteroaryl, 1-alkenyl, 1-alkynyl, and —$R^9$; or together V and Z are connected to form a cyclic group containing 3–5 atoms, optionally 1 heteroatom, substituted with hydroxy, acyloxy, alkoxycarboxy, or aryloxycarboxy attached to a carbon atom that is three atoms from an oxygen attached to the phosphorus; or together V and W are connected to form a cyclic group containing 3 carbon atoms substituted with hydroxy, acyloxy, alkoxycarboxy, alkylthiocarboxy, hydroxymethyl, and aryloxycarboxy attached to a carbon atom that is three atoms from an oxygen attached to the phosphorus;

Z is selected from the group consisting of —CH$_2$OH, —CH$_2$OCO$R^3$, —CH$_2$OC(O)S$R^3$, —CH$_2$OCO$_2R^3$, —S$R^3$, —S(O)$R^3$, —CH$_2$N$_3$, —CH$_2$N$R^2{}_2$, —CH$_2$Ar, —CH(Ar)OH, —CH(CH=C$R^2R^2$)OH, —CH(C≡C$R^2$)OH, and —$R^2$;

with the provisos that:
a) V, Z, W are not all —H; and
b) when Z is —$R^2$, then at least one of V and W is not —H or —$R^9$;

$R^2$ is selected from the group consisting of $R^3$ and —H;

$R^3$ is selected from the group consisting of alkyl, aryl, alicyclic, and aralkyl; and $R^9$ is selected from the group consisting of alkyl, aralkyl, and alicyclic.

Particularly preferred are such groups wherein V and W both form a 6-membered carbocyclic ring substituted with 0–4 groups, selected from the group consisting of hydroxy, acyloxy, alkoxycarbonyloxy, and alkoxy; and Z is —$R^2$. Also particularly preferred are such groups wherein V and W are hydrogen; and Z is selected from the group consisting of hydroxyalkyl, acyloxyalkyl, alkyloxyalkyl, and alkoxycarboxyalkyl. Also particularly preferred are such groups wherein V and W are independently selected from the group consisting of hydrogen, optionally substituted aryl, and optionally substituted heteroaryl, with the proviso that at least one of V and W is optionally substituted aryl or optionally substituted heteroaryl.

Also particularly preferred are such compounds where $R^1$ is alicyclic where the cyclic moiety contains carbonate or thiocarbonate.

Preferred $R^4$ and $R^7$ groups include —H, and lower alkyl.

In one preferred aspect, B is NH, D is

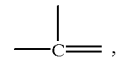

and Q is —C=. In another preferred aspect, B is —N=, D is

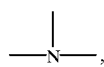

and Q is —C=.

In another preferred aspect, A, L, and E are independently —NR$^8_2$, lower alkyl, lower perhaloalkyl, lower alkoxy, halogen, —OH, or —H, X is aryl, alkoxyalkyl, alkyl, alkylthio, 1,1-dihaloalkyl, carbonylalkyl, alkyl(hydroxy), alkyl(sulfonate), alkylaminocarbonyl, and alkylcarbonylamino, and each R$^4$ and R$^7$ is independently —H, or lower alkyl. Particularly preferred are such compounds where A, L, and E are independently —H, lower alkyl, halogen, and —NR$^8_2$; J is —H, halogen, haloalkyl, hydroxyalkyl, —R$^8_2$N-alkyl, lower alkyl, lower aryl, heterocyclic, and alicyclic, or together with Y forms a cyclic group; and X is heteroaryl, alkylaminocarbonyl, 1,1-dihaloalkyl, and alkoxyalkyl. Especially preferred are such compounds where A is —H, —NH$_2$, —F, or —CH$_3$, L is —H, —F, —OCH$_3$, or —CH$_3$, E is —H, or —Cl, J is —H, halo, C1–C5 hydroxyalkyl, C1–C5 haloalkyl, C1–C5 R$^8_2$N-alkyl, C1–C5 alicyclic or C1–C5 alkyl, X is —CH$_2$OCH$_2$—, or 2,5-furanyl; and Y is lower alkyl. Preferred are such compounds where B is NH, D is

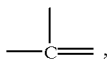

and Q is —C= or where B is —N=, D is

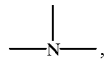

and Q is —C=.

Most preferred are compounds where:
1) A is —NH$_2$, L is —F, E is —H, J is —H, Y is isobutyl, and X is 2,5-furanyl;
2) A is —NH$_2$, L is —F, E is —H, J is —Cl, Y is isobutyl, and X is 2,5-furanyl.
3) A is —H, L is —H, E is —Cl, J is —H, B is —NH, D is

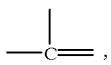

Q is —C=, and Y is isobutyl; and
4) A is —CH$_3$, L is —H, E is —H, J is —H, B is —N=, D is

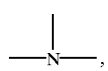

Q is —C=, and Y is isobutyl.

Particularly preferred are such compounds where R$^1$ is —CH$_2$OC(O)—C(CH$_3$)$_3$.

Another especially preferred aspect are such compounds where A, L, and E are —H, lower alkyl, halogen, or —NR$^8_2$, J is —H, halogen, lower alkyl, lower aryl, heterocyclic, or alicyclic, or together with Y forms a cyclic group, and X is heteroaryl, alkylaminocarbonyl, or alkoxyalkyl.

In the following examples of preferred compounds, the following prodrugs are preferred:

Acyloxyalkyl esters;
Alkoxycarbonyloxyalkyl esters;
Aryl esters;
Benzyl and substituted benzyl esters;
Disulfide containing esters;
Substituted (1,3-dioxolen-2-one)methyl esters;
Substituted 3-phthalidyl esters;
Cyclic-[2'-hydroxymethyl]-1,3-propanyl diesters and hydroxy protected forms; Lactone type esters; and all mixed esters resulted from possible combinations of above esters.

More preferred are the following:
Bis-pivaloyloxymethyl esters;
Bis-isobutyryloxymethyl esters;
Cyclic-[2'-hydroxymethyl]-1,3-propanyl diester;
Cyclic-[2'-acetoxymethyl]-1,3-propanyl diester;
Cyclic-[2'-methyloxycarbonyloxymethyl]-1,3-propanyl diester;
Bis-benzoylthiomethyl esters;
Bis-benzoylthioethyl esters;
Bis-benzoyloxymethyl esters;
Bis-p-fluorobenzoyloxymethyl esters;
Bis-6-chloronicotinoyloxymethyl esters;
Bis-5-bromonicotinoyloxymethyl esters;
Bis-thiophenecarbonyloxymethyl esters;
Bis-2-furoyloxymethyl esters;
Bis-3-furoyloxymethyl esters;
Diphenyl esters;
Bis-(4-methoxyphenyl) esters;
Bis-(2-methoxyphenyl) esters;
Bis-(2-ethoxyphenyl) esters;
Mono-(2-ethoxyphenyl) esters;
Bis-(4-acetamidophenyl) esters;
Bis-(4-aceyloxyphenyl) esters;
Bis-(4-hydroxyphenyl) esters;
Bis-(2-acetoxyphenyl) esters;
Bis-(3-acetoxyphenyl) esters;
Bis-(4-morpholinophenyl) esters;
Bis-[4-(1-triazolophenyl) esters;
Bis-(3-N,N-dimethylaminophenyl) esters;
Bis-(2-tetrahydronapthyl) esters;
Bis-(3-chloro-4-methoxy)benzyl esters;
Bis-(3-bromo-4-methoxy)benzyl esters;
Bis-(3-cyano-4-methoxy)benzyl esters;
Bis-(3-chloro-4-acetoxy)benzyl esters;
Bis-(3-bromo-4-acetoxy)benzyl esters;
Bis-(3-cyano-4-acetoxy)benzyl esters;
Bis-(4-chloro)benzyl esters;
Bis-(4-acetoxy)benzyl esters;
Bis-(3,5-dimethoxy-4-acetoxy)benzyl esters;
Bis-(3-methyl-4-acetoxy)benzyl esters;
Bis-(benzyl)esters;
Bis-(3-methoxy-4-acetoxy)benzyl esters;
Bis-(3-chloro-4-acetoxy)benzyl esters;
cyclic-(2,2-dimethylpropyl)phosphonoamidate;
cyclic-(2-hydroxymethylpropyl) ester;
Bis-(6'-hydroxy-3',4'-disulfide)hexyl esters;
Bis-(6'-acetoxy-3',4'-disulfide)hexyl esters;
(3',4'-Dithia)cyclononane esters;
Bis-(5-methyl-1,3-dioxolen-2-one-4-yl)methyl esters;
Bis-(5-ethyl-1,3-dioxolen-2-one-4-yl)methyl esters;
Bis-(5-tert-butyl-1,3-dioxolen-2-one-4-yl)methyl esters;
Bis-3-(5,6,7-trimethoxy)phthalidyl esters;
Bis-(cyclohexyloxycarbonyloxymethyl) esters;
Bis-(isopropyloxycarbonyloxymethyl) esters;
Bis-(ethyloxycarbonyloxymethyl) esters;
Bis-(methyloxycarbonyloxymethyl) esters;

Bis-(isopropylthiocarbonyloxymethyl) esters;
Bis-(phenyloxycarbonyloxymethyl) esters;
Bis-(benzyloxycarbonyloxymethyl) esters;
Bis-(phenylthiocarbonyloxymethyl) esters;
Bis-(p-methoxyphenyloxycarbonyloxymethyl) esters;
Bis-(m-methoxyphenyloxycarbonyloxymethyl) esters;
Bis-(o-methoxyphenyloxycarbonyloxymethyl) esters;
Bis-(o-methylphenyloxycarbonyloxymethyl) esters;
Bis-(p-chlorophenyloxycarbonyloxymethyl) esters;
Bis-(1,4-biphenyloxycarbonyloxymethyl) esters;
Bis-[(2-phthalimidoethyl)oxycarbonyloxymethyl]esters;
Bis-(N-Phenyl, N-methylcarbamoyloxymethyl) esters;
Bis-(2-trichloroethyl) esters;
Bis-(2-bromoethyl) esters;
Bis-(2-iodoethyl) esters;
Bis-(2-azidoethyl) esters;
Bis-(2-acetoxyethyl) esters;
Bis-(2-aminoethyl) esters;
Bis-(2-N,N-diaminoethyl) esters;
Bis-(2-aminoethyl) esters;
Bis-(methoxycarbonylmethyl) esters;
Bis-(2-aminoethyl) esters;
Bis-[N, N-di (2-hydroxyethyl)]amidomethylesters;
Bis-(2-aminoethyl) esters;
Bis-(2-methyl-5-thiozolomethyl) esters;
Bis-(bis-2-hydroxyethylamidomthyl) esters.

Most preferred are the following:
Bis-pivaloyloxymethyl esters;
Bis-isobutyryloxymethyl esters;
cyclic-(2-hydroxymethylpropyl) ester;
cyclic-(2-acetoxymethylpropyl) ester;
cyclic-(2-methyloxycarbonyloxymethylpropyl) ester;
cyclic-(2-cyclohexylcarbonyloxymethylpropyl)ester;
cyclic-(2-aminomethylpropyl)ester;
cyclic-(2-azidomethylpropyl)ester;
Bis-benzoylthiomethyl esters;
Bis-benzoylthioethylesters;
Bis-benzoyloxymethyl esters;
Bis-p-fluorobenzoyloxymethyl esters;
Bis-6-chloronicotinoyloxymethyl esters;
Bis-5-bromonicotinoyloxymethyl esters;
Bis-thiophenecarbonyloxymethyl esters;
Bis-2-furoyloxymethyl esters;
Bis-3-furoyloxymethyl esters;
Diphenyl esters;
Bis-(2-methyl)phenyl esters;
Bis-(2-methoxy)phenyl esters;
Bis-(2-ethoxy)phenyl esters;
Bis-(4-methoxy)phenyl esters;
Bis-(3-bromo-4-methoxy)benzyl esters;
Bis-(4-acetoxy)benzyl esters;
Bis-(3,5-dimethoxy-4-acetoxy)benzyl esters;
Bis-(3-methyl-4-acetoxy)benzyl esters;
Bis-(3-methoxy-4-acetoxy)benzyl esters;
Bis-(3-chloro-4-acetoxy)benzyl esters;
Bis-(cyclohexyloxycarbonyloxymethyl) esters;
Bis-(isopropyloxycarbonyloxymethyl) esters;
Bis-(ethyloxycarbonyloxymethyl) esters;
Bis-(methyloxycarbonyloxymethyl) esters;
Bis-(isopropylthiocarbonyloxymethyl) esters;
Bis-(phenyloxycarbonyloxymethyl) esters;
Bis-(benzyloxycarbonyloxymethyl) esters;
Bis-(phenylthiocarbonyloxymethyl) esters;
Bis-(p-methoxyphenyloxycarbonyloxymethyl) esters;
Bis-(m-methoxyphenyloxycarbonyloxymethyl) esters;
Bis-(o-methoxyphenyloxycarbonyloxymethyl) esters;
Bis-(o-methylphenyloxycarbonyloxymethyl) esters;
Bis-(p-chlorophenyloxycarbonyloxymethyl) esters;
Bis-(1,4-biphenyloxycarbonyloxymethyl) esters;
Bis-[(2-phthalimidoethyl)oxycarbonyloxymethyl]esters;
Bis-(6'-hydroxy-3',4'-disulfide)hexyl esters; and
(3',4'-Disulfide)cyclononane esters.
Bis-(2-bromoethyl) esters;
Bis-(2-aminoethyl) esters;
Bis-(2-N,N-diaminoethyl) esters;

Examples of preferred compounds include, but are not limited to the compounds of Table 1 and salts and prodrugs thereof:

TABLE 1

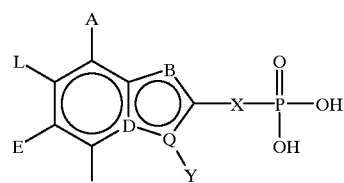

| Table Compound # | Synthetic Example No. | A | L | E | $J^2$ | $Y^3$ | $X^1$ | D | B | Q |
|---|---|---|---|---|---|---|---|---|---|---|
| 1. | | NH2 | F | H | Cl | isobutyl | 2,5-furanyl | C | CH | N |
| 2. | | NH2 | F | H | Br | isobutyl | 2,5-furanyl | C | CH | N |
| 3. | | NH2 | F | H | OH | isobutyl | 2,5-furanyl | C | CH | N |
| 4. | | NH2 | F | H | OMe | isobutyl | 2,5-furanyl | C | CH | N |
| 5. | | NH2 | F | H | CN | isobutyl | 2,5-furanyl | C | CH | N |
| 6. | | NH2 | F | H | CO2H | isobutyl | 2,5-furanyl | C | CH | N |
| 7. | | NH2 | F | H | CO2Me | isobutyl | 2,5-furanyl | C | CH | N |
| 8. | | NH2 | F | H | CONH2 | isobutyl | 2,5-furanyl | C | CH | N |
| 9. | | NH2 | F | H | NHCONH2 | isobutyl | 2,5-furanyl | C | CH | N |
| 10. | | NH2 | F | H | Me | isobutyl | 2,5-furanyl | C | CH | N |
| 11. | | NH2 | F | H | Et | isobutyl | 2,5-furanyl | C | CH | N |
| 12. | | NH2 | F | H | n-Pr | isobutyl | 2,5-furanyl | C | CH | N |
| 13. | | H | F | Cl | i-Pr | isobutyl | 2,5-furanyl | C | NH | C |
| 14. | | H | F | Cl | n-Bu | isobutyl | 2,5-furanyl | C | NH | C |
| 15. | | H | F | Cl | i-butyl | isobutyl | 2,5-furanyl | C | NH | C |
| 16. | | H | F | Cl | n-pentyl | isobutyl | 2,5-furanyl | C | NH | C |
| 17. | | H | F | Cl | 2-pentyl | isobutyl | 2,5-furanyl | C | NH | C |
| 18. | | H | F | Cl | 2-pentyl | isobutyl | 2,5-furanyl | C | NH | C |

TABLE 1-continued

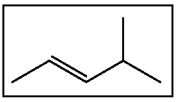

| Table Compound # | Synthetic Example No. | A | L | E | J² | Y³ | X¹ | D | B | Q |
|---|---|---|---|---|---|---|---|---|---|---|
| 19. | | H | F | Cl | 2-chloroethyl | isobutyl | 2,5-furanyl | C | NH | C |
| 20. | | H | F | Cl | 2-bromoethyl | isobutyl | 2,5-furanyl | C | NH | C |
| 21. | | H | F | Cl | 2-hydroxyethyl | isobutyl | 2,5-furanyl | C | CH | N |
| 22. | | H | F | Cl | 2-carboxyethyl | isobutyl | 2,5-furanyl | C | CH | N |
| 23. | | H | F | Cl | 2-carboxyamidoethyl | isobutyl | 2,5-furanyl | C | CH | N |
| 24. | | H | F | Cl | 3-carboxypropyl | isobutyl | 2,5-furanyl | C | CH | N |
| 25. | | H | F | Cl | 3-carboxyamidopropyl | isobutyl | 2,5-furanyl | C | CH | N |
| 26. | | H | F | Cl | 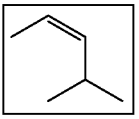 | isobutyl | 2,5-furanyl | C | CH | N |
| 27. | | H | F | Cl | 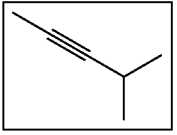 | isobutyl | 2,5-furanyl | C | CH | N |
| 28. | | H | F | Cl | | isobutyl | 2,5-furanyl | C | CH | N |
| 29. | | H | F | Cl | Cyclopentyl | isobutyl | 2,5-furanyl | C | CH | N |
| 30. | | H | H | Cl | Cyclopentylmethyl | isobutyl | 2,5-furanyl | C | CH | N |
| 31. | | H | H | Cl | Cyclopentylethyl | isobutyl | 2,5-furanyl | C | NH | C |
| 32. | | H | H | Cl | Phenyl | isobutyl | 2,5-furanyl | C | NH | C |
| 33. | | H | H | Cl | bentyl | isobutyl | 2,5-furanyl | C | NH | C |
| 34. | | H | H | Cl | phenethyl | isobutyl | 2,5-furanyl | C | NH | C |
| 35. | | H | H | Cl | m-chlorophenyl | isobutyl | 2,5-furanyl | C | NH | C |
| 36. | | H | H | Cl | p-chlorophenyl | isobutyl | 2,5-furanyl | C | NH | C |
| 37. | | H | H | Cl | m-bromophenyl | isobutyl | 2,5-furanyl | C | NH | C |
| 38. | | H | H | Cl | p-bromophenyl | isobutyl | 2,5-furanyl | C | NH | C |
| 39. | | H | H | Cl | m-hydroxyphenyl | isobutyl | 2,5-furanyl | C | NH | C |
| 40. | | H | H | Cl | p-hydroxyphenyl | isobutyl | 2,5-furanyl | C | NH | C |
| 41. | | H | H | Cl | m-carboxyphenyl | isobutyl | 2,5-furanyl | C | NH | C |
| 42. | | H | H | Cl | p-carboxyphenyl | isobutyl | 2,5-furanyl | C | NH | C |
| 43. | | H | H | Cl | m-carboxyamidophenyl | isobutyl | 2,5-furanyl | C | NH | C |
| 44. | | H | H | Cl | p-carboxyamidophenyl | isobutyl | 2,5-furanyl | C | NH | C |
| 45. | | H | H | Cl | N-pyrrolidinyl | isobutyl | 2,5-furanyl | C | CH | N |
| 46. | | H | H | Cl | N-thiomorpholinyl | isobutyl | 2,5-furanyl | C | CH | N |
| 47. | | H | H | Cl | N-imidazolyl | isobutyl | 2,5-furanyl | C | CH | N |
| 48. | | H | H | Cl | N-piperdinylmethyl | isobutyl | 2,5-furanyl | C | CH | N |
| 49. | | H | H | Cl | N-piperazinylmethyl | isobutyl | 2,5-furanyl | C | CH | N |
| 50. | | H | H | Cl | N-morpholinylmethyl | isobutyl | 2,5-furanyl | C | CH | N |
| 51. | | H | H | Cl | N-pyrrolidinemethyl | isobutyl | 2,5-furanyl | C | CH | N |
| 52. | | H | H | Cl | N-piperdinylethyl | isobutyl | 2,5-furanyl | C | CH | N |
| 53. | | H | H | Cl | N-piperazinylethyl | isobutyl | 2,5-furanyl | C | CH | N |
| 54. | | H | H | Cl | N-morpholinylethyl | isobutyl | 2,5-furanyl | C | CH | N |
| 55. | | H | H | Cl | 4-imdazolylethyl | isobutyl | 2,5-furanyl | C | NH | C |
| 56. | | H | H | Cl | 4-oxazolylethyl | isobutyl | 2,5-furanyl | C | NH | C |
| 57. | | H | H | Cl | 4-thiazolylethyl | isobutyl | 2,5-furanyl | C | NH | C |
| 58. | | H | H | Cl | 4-pyrimidylethyl | isobutyl | 2,5-furanyl | C | NH | C |
| 59. | | H | H | Cl | 5-pyrimidylethyl | isobutyl | 2,5-furanyl | C | NH | C |
| 60. | | F | H | Cl | H | isobutyl | 2,5-furanyl | C | NH | C |
| 61. | | Me | Me | Cl | H | isobutyl | 2,5-furanyl | C | NH | C |
| 62. | | Et | Me | Cl | H | isobutyl | 2,5-furanyl | C | NH | C |
| 63. | | n-Pr | F | Cl | H | isobutyl | 2,5-furanyl | C | NH | C |
| 64. | | i-Pr | F | Cl | H | isobutyl | 2,5-furanyl | C | NH | C |
| 65. | | NH2 | F | Cl | H | isobutyl | 2,5-furanyl | C | NH | C |
| 66. | | OH | F | Cl | H | isobutyl | 2,5-furanyl | C | NH | C |

TABLE 1-continued

| Table Compound # | Synthetic Example No. | A | L | E | J² | Y³ | X¹ | D | B | Q |
|---|---|---|---|---|---|---|---|---|---|---|
| 67. | | Cyclopentyl | H | Cl | H | isobutyl | 2,5-furanyl | C | NH | C |
| 68. | | Phenyl | H | Cl | H | isobutyl | 2,5-furanyl | C | NH | C |
| 69. | | acetyl | H | Cl | H | isobutyl | 2,5-furanyl | C | NH | C |
| 70. | | carboxy | H | Cl | H | isobutyl | 2,5-furanyl | C | NH | C |
| 71. | | carboxyamido | H | Cl | H | isobutyl | 2,5-furanyl | C | NH | C |
| 72. | | SH | H | Cl | H | isobutyl | 2,5-furanyl | C | NH | C |
| 73. | | NHNH2 | H | Cl | H | isobutyl | 2,5-furanyl | C | NH | C |
| 74. | | NHOH | H | Cl | H | isobutyl | 2,5-furanyl | C | NH | C |
| 75. | | NH2 | F | Cl | Et | isobutyl | 2,5-furanyl | C | NH | C |
| 76. | | Et | F | H | Et | isobutyl | 2,5-furanyl | C | NH | C |
| 77. | | n-Pr | F | H | Et | isobutyl | 2,5-furanyl | C | NH | C |
| 78. | | OH | F | H | Et | isobutyl | 2,5-furanyl | C | NH | C |
| 79. | | NHNH2 | F | H | Et | isobutyl | 2,5-furanyl | C | NH | C |
| 80. | | NHOH | F | H | nPr | isobutyl | 2,5-furanyl | C | NH | C |
| 81. | | Carboxy | F | H | Et | isobutyl | 2,5-furanyl | C | NH | C |
| 82. | | acetyl | F | H | Et | isobutyl | 2,5-furanyl | C | NH | C |
| 83. | | F | F | H | Et | isobutyl | 2,5-furanyl | C | NH | C |
| 84. | | H | F | Cl | H | isobutyl | 2,5-furanyl | C | NH | C |
| 85. | | NH2 | Cl | Cl | H | isobutyl | 2,5-furanyl | C | NH | C |
| 86. | | NH2 | OH | Cl | Et | isobutyl | 2,5-furanyl | C | NH | C |
| 87. | | H | OMe | Cl | H | isobutyl | 2,5-furanyl | C | NH | C |
| 88. | | H | NO2 | Cl | H | isobutyl | 2,5-furanyl | C | NH | C |
| 89. | | H | Et | Cl | H | isobutyl | 2,5-furanyl | C | NH | C |
| 90. | | H | CN | Cl | H | isobutyl | 2,5-furanyl | C | NH | C |
| 91. | | NH2 | F | Cl | Et | isobutyl | 2,5-furanyl | C | NH | C |
| 92. | | H | CO2NH2 | Cl | H | isobutyl | 2,5-furanyl | C | CH | N |
| 93. | | NH2 | F | Me | Et | isobutyl | 2,5-furanyl | C | CH | N |
| 94. | | H | H | acetenyl | H | isobutyl | 2,5-furanyl | C | CH | N |
| 95. | | H | H | vinyl | H | isobutyl | 2,5-furanyl | C | CH | N |
| 96. | | NH2 | Cl | ethyl | H | isobutyl | 2,5-furanyl | C | CH | N |
| 97. | | H | H | NO2 | H | isobutyl | 2,5-furanyl | C | CH | N |
| 98. | | H | H | NH2 | H | isobutyl | 2,5-furanyl | C | CH | N |
| 99. | | H | H | CN | H | isobutyl | 2,5-furanyl | C | CH | N |
| 100. | | NH2 | F | SMe | H | isobutyl | 2,5-furanyl | C | CH | N |
| 101. | | H | H | OMe | H | isobutyl | 2,5-furanyl | C | CH | N |
| 102. | | H | H | phenyl | H | isobutyl | 2,5-furanyl | C | CH | N |
| 103. | | NH2 | F | CF3 | Et | isobutyl | 2,5-furanyl | C | CH | N |
| 104. | | H | H | NMe2 | H | isobutyl | 2,5-furanyl | C | CH | N |
| 105. | | H | H | N-pyrrolidinyl | H | isobutyl | 2,5-furanyl | C | CH | N |
| 106. | | H | H | F | H | isobutyl | 2,5-furanyl | C | CH | N |
| 107. | | H | H | Br | H | isobutyl | 2,5-furanyl | C | CH | N |
| 108. | | NH2 | F | i-Pr | H | isobutyl | 2,5-furanyl | C | CH | N |
| 109. | | NH2 | F | n-Pr | H | isobutyl | 2,5-furanyl | C | CH | N |
| 110. | | NH2 | F | H | Et | ethyl | 2,5-furanyl | C | CH | N |
| 111. | | NH2 | Cl | F | n-Pr | ethoxy-1-butyl | 2,5-furanyl | C | NH | C |
| 112. | | NH2 | F | F | Et | Cyclohexyl methyl | 2,5-furanyl | C | NH | C |
| 113. | | NH2 | F | Cl | Et | Cyclopentyl ethyl | 2,5-furanyl | C | NH | C |
| 114. | | NH2 | OH | Cl | n-Bu | phenyl | 2,5-furanyl | C | NH | C |
| 115. | | NH2 | F | H | cyclopentyl | phenyl | 2,5-furanyl | C | NH | C |
| 116. | | NH2 | F | F | Et | phenethyl | 2,5-furanyl | C | NH | C |
| 117. | | NH2 | F | Cl | 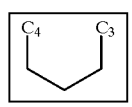 | | 2,5-furanyl | C | NH | C |

TABLE 1-continued

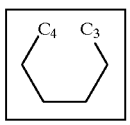

| Table Compound # | Synthetic Example No. | A | L | E | J² | Y³ | X¹ | D | B | Q |
|---|---|---|---|---|---|---|---|---|---|---|
| 118. | | NH2 | F | H | | 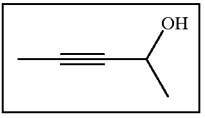 | 2,5-furanyl | C | NH | C |
| 119. | | NH2 | F | H | Et | 4-carboxamido-1-butyl | 2,5-furanyl | C | NH | C |
| 120. | | NH2 | F | H | Et | 4-carboxy-1-butyl | 2,5-furanyl | C | NH | C |
| 121. | | H | H | Cl | H | m-OHPh | 2,5-furanyl | C | NH | C |
| 122. | | H | H | Cl | H | m-CO2HPh | 2,5-furanyl | C | NH | C |
| 123. | | H | H | Cl | H | p-CO2HPh | 2,5-furanyl | C | NH | C |
| 124. | | H | H | Cl | H | m-CONH2Ph | 2,5-furanyl | C | NH | C |
| 125. | | H | H | Cl | H | p-CO2HPh | 2,5-furanyl | C | NH | C |
| 126. | | H | H | Cl | H | m-ClPh | 2,5-furanyl | C | NH | C |
| 127. | | H | H | Cl | H | p-ClPh | 2,5-furanyl | C | NH | C |
| 128. | | H | H | Cl | H | COPh | 2,5-furanyl | C | NH | C |
| 129. | | H | H | Cl | H | SO2Bu | 2,5-furanyl | C | NH | C |
| 130. | | NH2 | F | H | H | isobutyl | 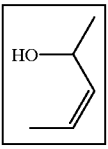 | C | NH | C |
| 131. | | NH2 | F | H | H | isobutyl | 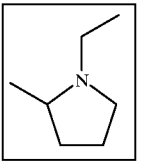 | C | NH | C |
| 132. | | NH2 | F | H | H | isobutyl | CH2CH2CH(OH) | C | NH | C |
| 133. | | NH2 | F | H | H | isobutyl | CH2CH2CH(CO2H) | C | NH | C |
| 134. | | NH2 | F | H | H | isobutyl | CH2CH2CH(SO3H) | C | NH | C |
| 135. | | NH2 | F | H | H | isobutyl | CH2CH2CH(PO3H2) | C | NH | C |
| 136. | | H | H | Cl | H | isobutyl | 1,3-phenyl | C | NH | C |
| 137. | | H | H | Cl | H | isobutyl | 2,6-pyridyl | C | NH | C |
| 138. | | H | H | Cl | H | isobutyl | 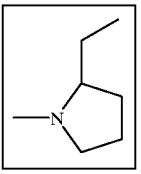 | C | NH | C |
| 139. | | H | H | Cl | H | isobutyl |  | C | NH | C |

TABLE 1-continued

| Table Compound # | Synthetic Example No. | A | L | E | J[2] | Y[3] | X[1] | D | B | Q |
|---|---|---|---|---|---|---|---|---|---|---|
| 140. | | H | H | Cl | H | isobutyl | (N-ethyl-2-methyl-4-hydroxypyrrolidine) | C | NH | C |
| 141. | | H | H | Cl | H | isobutyl | (1-methyl-2-ethylcyclohexyl) | C | NH | C |
| 142. | | H | H | Cl | H | isobutyl | (2-ethyl-methylbenzene) | C | NH | C |
| 143. | | NH2 | F | H | H | isobutyl | CH2OCF2 | C | NH | C |
| 144. | | NH2 | F | H | H | isobutyl | (1-ethoxy-propan-2-ol) | C | NH | C |
| 145. | | H | H | Cl | H | isobutyl | (2-methylpentan-1-ol) | C | CH | N |
| 146. | | H | H | Cl | H | isobutyl | CH(NH2)CH2CH2 | C | CH | N |
| 147. | | H | H | Cl | H | isobutyl | CH(OH)CH2CH2 | C | CH | N |
| 148. | | H | H | Cl | H | isobutyl | (pent-3-en-2-one) | C | CH | N |
| 149. | | NH2 | F | H | H | isobutyl | CONHCH2 | C | CH | N |
| 150. | | NH2 | F | H | H | isobutyl | SO2NHCH2 | C | CH | N |
| 151. | | H | H | Cl | H | isobutyl | NHCOCH2 | C | CH | N |

TABLE 1-continued
| Table Compound # | Synthetic Example No. | A | L | E | J² | Y³ | X¹ | D | B | Q |
|---|---|---|---|---|---|---|---|---|---|---|
| 152. | | H | H | Cl | H | isobutyl | 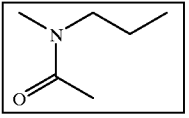 | C | CH | N |
| 153. | | H | H | Cl | H | isobutyl | 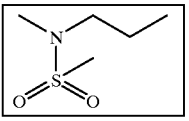 | C | CH | N |
| 154. | | NH2 | F | H | Et | | 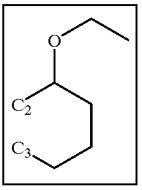 | C | NH | C |
| 155. | | NH2 | F | H | Et | | 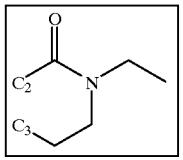 | C | NH | C |
| 156. | | H | H | Cl | H | | 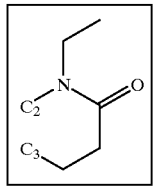 | C | NH | C |
| 157. | | H | H | Cl | H | isobutyl | 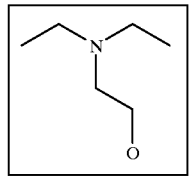 | C | NH | C |
| 158. | | H | H | Cl | H | isobutyl | 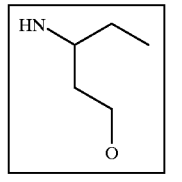 | C | NH | C |

TABLE 1-continued

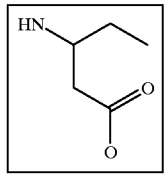

| Table Compound # | Synthetic Example No. | A | L | E | J² | Y³ | X¹ | D | B | Q |
|---|---|---|---|---|---|---|---|---|---|---|
| 159. | | H | H | Cl | H | isobutyl | 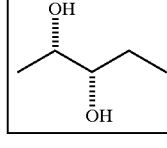 | C | NH | C |
| 160. | | NH2 | F | Cl | H | isobutyl | | C | NH | C |
| 161. | 1.1 | NH2 | H | H | H | H | CONHCH2 | C | NH | C |
| 162. | 3.1 | NH2 | H | H | H | phenethyl | CONHCH2 | C | NH | C |
| 163. | 2.1 | NH2 | H | H | H | Phenyl | CONHCH2 | C | NH | C |
| 164. | 1.4 | H | H | H | H | Me | CONHCH2 | C | CH | N |
| 165. | 1.3 | NH2 | H | OMe | H | H | CONHCH2 | C | NH | C |
| 166. | 1.2 | H | H | H | H | H | CONHCH2 | C | NH | C |
| 167. | 9.1 | NH2 | H | H | H | isobutyl | 2,5-furanyl | C | C | N |
| 168. | 5.1 | H | H | H | H | H | 2,5-furanyl | C | C | N |
| 169. | 6.1 | H | H | H | H | isobutyl | 2,5-furanyl | C | C | N |
| 170. | 7.1 | H | H | H | H | Br | 2,5-furanyl | C | NH | C |
| 171. | 8.1 | H | H | H | H | Cl | 2,5-furanyl | C | NH | C |
| 172. | 7.2 | H | H | H | H | Phenyl | 2,5-furanyl | C | NH | C |
| 173. | | H | F | Cl | i-Pr | isobutyl | 2,5-furanyl | N | N | C |
| 174. | | H | F | Cl | n-Bu | isobutyl | 2,5-furanyl | N | N | C |
| 175. | | H | F | Cl | i-butyl | isobutyl | 2,5-furanyl | N | N | C |
| 175. | | H | F | Cl | n-pentyl | isobutyl | 2,5-furanyl | N | N | C |
| 177. | | H | F | Cl | 2-penyl | isobutyl | 2,5-furanyl | N | N | C |
| 178. | | H | F | Cl | 3-pentyl | isobutyl | 2,5-furanyl | N | N | C |
| 179. | | H | F | Cl | 2-chloroethyl | isobutyl | 2,5-furanyl | N | N | C |
| 180. | | H | F | Cl | 2-bromoethyl | isobutyl | 2,5-furanyl | N | N | C |
| 181. | | H | H | Cl | Cyclopentylethyl | isobutyl | 2,5-furanyl | N | N | C |
| 182. | | H | H | Cl | Phenyl | isobutyl | 2,5-furanyl | N | N | C |
| 183. | | H | H | Cl | benzyl | isobutyl | 2,5-furanyl | N | N | C |
| 184. | | H | H | Cl | phenetnyl | isobutyl | 2,5-furanyl | N | N | C |
| 185. | | H | H | Cl | m-chlorophenyl | isobutyl | 2,5-furanyl | N | N | C |
| 186. | | H | H | Cl | p-chlorophenyl | isobutyl | 2,5-furanyl | N | N | C |
| 187. | | H | H | Cl | m-bromophenyl | isobutyl | 2,5-furanyl | N | N | C |
| 188. | | H | H | Cl | p-bromophenyl | isobutyl | 2,5-furanyl | N | N | C |
| 189. | | H | H | Cl | m-hydroxyphenyl | isobutyl | 2,5-furanyl | N | N | C |
| 190. | | H | H | Cl | p-hydroxyphenyl | isobutyl | 2,5-furanyl | N | N | C |
| 191. | | H | H | Cl | m-carboxphenyl | isobutyl | 2,5-furanyl | N | N | C |
| 192. | | H | H | Cl | p-carboxyphenyl | isobutyl | 2,5-furanyl | N | N | C |
| 193. | | H | H | Cl | m-carboxylmidophenyl | isobutyl | 2,5-furanyl | N | N | C |
| 194. | | H | H | Cl | p-carboxylmidophenyl | isobutyl | 2,5-furanyl | N | N | C |
| 195. | | H | H | Cl | 4-imidazolylethyl | isobutyl | 2,5-furanyl | N | N | C |
| 196. | | H | H | Cl | 4-oxazolylethyl | isobutyl | 2,5-furanyl | N | N | C |
| 197. | | H | H | Cl | 4-thiazolylethyl | isobutyl | 2,5-furanyl | N | N | C |
| 198. | | H | H | Cl | 4-pyimidylethyl | isobutyl | 2,5-furanyl | N | N | C |
| 199. | | H | H | Cl | 5-pyrimidylethyl | isobutyl | 2,5-furanyl | N | N | C |
| 200. | | F | H | Cl | H | isobutyl | 2,5-furanyl | N | N | C |
| 201. | | Me | Me | Cl | H | isobutyl | 2,5-furanyl | N | N | C |
| 202. | | Et | Me | Cl | H | isobutyl | 2,5-furanyl | N | N | C |
| 203. | | n-Pr | F | Cl | H | isobutyl | 2,5-furanyl | N | N | C |
| 204. | | i-Pr | F | Cl | H | isobutyl | 2,5-furanyl | N | N | C |
| 205. | | NH2 | F | Cl | H | isobutyl | 2,5-furanyl | N | N | C |
| 206. | | OH | F | Cl | H | isobutyl | 2,5-furanyl | N | N | C |
| 207. | | Cyclopentyl | H | Cl | H | isobutyl | 2,5-furanyl | N | N | C |
| 206. | | Phenyl | H | Cl | H | isobutyl | 2,5-furanyl | N | N | C |

TABLE 1-continued

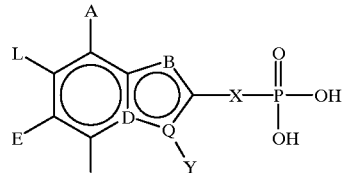

| Table Compound # | Synthetic Example No. | A | L | E | J² | Y³ | X¹ | D | B | Q |
|---|---|---|---|---|---|---|---|---|---|---|
| 209. | | acetyl | H | Cl | H | isobutyl | 2,5-furanyl | N | N | C |
| 210. | | carboxy | H | Cl | H | isobutyl | 2,5-furanyl | N | N | C |
| 211. | | carboxyamido | H | Cl | H | isobutyl | 2,5-furanyl | N | N | C |
| 212. | | SH | H | Cl | H | isobutyl | 2,5-furanyl | N | N | C |
| 213. | | NHNH2 | H | Cl | H | isobutyl | 2,5-furanyl | N | N | C |
| 214. | | NHOH | H | Cl | H | isobutyl | 2,5-furanyl | N | N | C |
| 215. | | NH2 | F | Cl | Et | isobutyl | 2,5-furanyl | N | N | C |
| 216. | | Et | F | H | Et | isobutyl | 2,5-furanyl | N | N | C |
| 217. | | n-Pr | F | H | Et | isobutyl | 2,5-furanyl | N | N | C |
| 218. | | OH | F | H | Et | isobutyl | 2,5-furanyl | N | N | C |
| 219. | | NHNH2 | F | H | Et | isobutyl | 2,5-furanyl | N | N | C |
| 220. | | NHOH | F | H | n-Pr | isobutyl | 2,5-furanyl | N | N | C |
| 221. | | Carboxy | F | H | Et | isobutyl | 2,5-furanyl | N | N | C |
| 222. | | acetyl | F | H | Et | isobutyl | 2,5-furanyl | N | N | C |
| 223. | | F | F | H | Et | isobutyl | 2,5-furanyl | N | N | C |
| 224. | | H | F | Cl | H | isobutyl | 2,5-furanyl | N | N | C |
| 225. | | NH2 | Cl | Cl | H | isobutyl | 2,5-furanyl | N | N | C |
| 226. | | NH2 | OH | Cl | Et | isobutyl | 2,5-furanyl | N | N | C |
| 227. | | H | OMe | Cl | H | isobutyl | 2,5-furanyl | N | N | C |
| 228. | | H | NO2 | Cl | H | isobutyl | 2,5-turanyl | N | N | C |
| 229. | | H | Et | Cl | H | isobutyl | 2,5-furanyl | N | N | C |
| 230. | | H | CN | Cl | H | isobutyl | 2,5-furanyl | N | N | C |
| 231. | | NH2 | F | Cl | Et | isobutyl | 2,5-furanyl | N | N | C |
| 232. | | NH2 | Cl | F | n-Pr | ethoxy-1-butyl | 2,5-furanyl | N | N | C |
| 233. | | NH2 | F | F | Et | Cyclohexyl | 2,5-furanyl | N | N | C |
| 234. | | NH2 | F | Cl | Et | Cyclopentyl | 2,5-furanyl | N | N | C |
| 235. | | NH2 | OH | Cl | n-Bu | phenyl | 2,5-furanyl | N | N | C |
| 236. | | NH2 | F | H | cyclopentyl | phenyl | 2,5-furanyl | N | N | C |
| 237. | | NH2 | F | F | Et | phenetnyl | 2,5-furanyl | N | N | C |
| 238. | | NH2 | F | H | Et | 4-carboxamido-1-butyl | 2,5-furanyl | N | N | C |
| 239. | | NH2 | F | H | Et | 4-carboxy-1-butyl | 2,5-furanyl | N | N | C |
| 240. | | H | H | Cl | H | m-OHPh | 2,5-furanyl | N | N | C |
| 241. | | H | H | Cl | H | m-CO2HPh | 2,5-furanyl | N | N | C |
| 242. | | H | H | Cl | H | p-CO2HPh | 2,5-furanyl | N | N | C |
| 243. | | H | H | Cl | H | m-CONH2Ph | 2,5-furanyl | N | N | C |
| 244. | | H | H | Cl | H | p-CO2HPh | 2,5-furanyl | N | N | C |
| 245. | | H | H | Cl | H | m-ClPh | 2,5-furanyl | N | N | C |
| 246. | | H | H | Cl | H | p-ClPh | 2,5-furanyl | N | N | C |
| 247. | | H | H | Cl | H | COPh | 2,5-furanyl | N | N | C |
| 248. | | H | H | Cl | H | SO2Bu | 2,5-furanyl | N | N | C |
| 249. | | Me | F | Cl | H | isobutyl | CH2CH2CH(OH) | N | N | C |
| 250. | | NH2 | F | H | H | isobutyl | CH2CH2CH(OH) | N | N | C |
| 251. | | H | F | H | H | isobutyl | CH2CH2CH(OH) | N | N | C |
| 252. | | Me | F | Cl | H | isobutyl | CH2CH2CH(SO3H) | N | N | C |
| 253. | | NH2 | F | H | H | isobutyl | CH2CH2CH(SO3H) | N | N | C |
| 254. | | H | F | H | H | isobutyl | CH2CH2CH(SO3H) | N | N | C |
| 255. | | Me | F | Cl | H | isobutyl | CH2CH2CF2 | N | N | C |
| 256. | | NH2 | F | H | H | isobutyl | CH2CH2CF2 | N | N | C |
| 257. | | H | F | H | H | isobutyl | CH2CH2CF2 | N | N | C |
| 258. | | Me | H | H | H | isobutyl | CH2CH2CH(OH) | N | N | C |
| 259. | | NH2 | H | H | H | isobutyl | CH2CH2CH(OH) | N | N | C |
| 260. | | H | H | H | H | isobutyl | CH2CH2CH(OH) | N | N | C |
| 261. | | Me | H | H | H | isobutyl | CH2CH2CH(SO3H) | N | N | C |
| 262. | | NH2 | H | H | H | isobutyl | CH2CH2CH(SO3H) | N | N | C |
| 263. | | H | H | H | H | isobutyl | CH2CH2CH(SO3H) | N | N | C |
| 264. | | Me | H | H | H | isobutyl | CH2CH2CF2 | N | N | C |
| 265. | | NH2 | H | H | H | isobutyl | CH2CH2CF2 | N | N | C |
| 266. | | H | H | H | H | isobutyl | CH2CH2CF2 | N | N | C |
| 267. | | Me | H | H | H | isobutyl | CH2OCH2 | N | N | C |
| 268. | | NH2 | H | H | H | isobutyl | CH2OCH2 | N | N | C |
| 269. | | H | H | H | H | isobutyl | CH2OCH2 | N | N | C |
| 270. | | Me | H | H | H | isobutyl | CH2OCH2 | C | NH | C |
| 271. | | NH2 | H | H | H | isobutyl | CH2OCH2 | C | NH | C |
| 272. | | H | H | H | H | isobutyl | CH2OCH2 | C | NH | C |

TABLE 1-continued

| Table Compound # | Synthetic Example No. | A | L | E | J² | Y³ | X¹ | D | B | Q |
|---|---|---|---|---|---|---|---|---|---|---|
| 273. | | Me | H | Cl | H | isobutyl | CH2OCH2 | C | NH | C |
| 274. | | NH2 | H | Cl | H | isobutyl | CH2OCH2 | C | NH | C |
| 275. | | H | H | Cl | H | isobutyl | CH2OCH2 | C | NH | C |
| 276. | 10.1 | H | H | Cl | H | isobutyl | 2,5-furanyl | C | NH | C |
| 277. | 11.5 | NH2 | H | H | H | phenyl | CH2OCH2 | N | N | C |
| 278. | 11.1 | H | H | H | H | Br | CH2OCH2 | N | N | C |
| 279. | 11.2 | H | H | H | H | H | CH2OCH2 | N | N | C |
| 280. | 11.3 | H | H | H | H | phenyl | CH2OCH2 | N | N | C |
| 281. | 13.1 | NH2 | H | H | H | H | CONHCH2 | N | N | C |
| 282. | 12.1 | H | H | H | H | H | CONHCH2 | N | N | C |
| 283. | 14.1 | H | H | H | H | H | 2,5-furanyl | N | N | C |
| 284. | 14.2 | H | H | Cl | H | H | 2,5-furanyl | N | N | C |
| 285. | 14.3 | Cl | H | CF3 | H | H | 2,5-furanyl | N | N | C |
| 286. | 14.4 | Me | H | H | H | isobutyl | 2,5-furanyl | N | N | C |
| 287. | | Me | Cl | H | Et | neopentyl | 2,5-furanyl | N | N | C |
| 288. | | H | NH2 | Cl | H | isobutyl | 2,5-furanyl | N | N | C |
| 289. | | CF3 | H | H | H | isobutyl | 2,5-furanyl | N | N | C |
| 290. | | H | CONH2 | H | H | isobutyl | 2,5-furanyl | N | N | C |
| 291. | | Me | Cl | H | Et | neopentyl | CH2CH2CO | N | N | C |
| 292. | | H | NH2 | Cl | H | isobutyl | CH2CH2CO | N | N | C |
| 203. | | NH2 | H | H | H | isobutyl | CH2CH2CO | N | N | C |
| 294. | | H | CONH2 | H | H | isobutyl | CH2CH2CO | N | N | C |

[1]In the table for X where structures are depicted, the line on the left side is part of the indole ring, an atom or the left side is attached to the indole ring, and the line on the right side is attached directly to the P of the phosphonate.
[2]In the Table for J where structures are depicted, the line on the left side is a direct attachment to the indole ring.
[3]In the Table where Y is a cyclic group with J or X, the structure depicts which position on the indole ring the group is attached to J corresponds to C-4, Y to C-3, and X to C-2.

More preferred are the following compounds from Table 1 and salts and prodrugs thereof:
2, 11, 12, 15, 17, 18, 29, 46, 50, 60, 61, 62, 65, 66, 71, 75, 78, 82, 85, 86, 93, 100, 103, 108, 109, 110, 111, 112, 115, 116, 117, 118, 119, 120, 121, 122, 124, 130, 132, 133, 134, 135, 143, 149, 150, 154, 155, 156, 157, 158, 174, 180, 200, 201, 205, 211, 215, 225, 229, 234, 238, 249, 250, 252, 253, 255, 256, 258, 259, 261, 262, 264, 265, 267, 268, 269, 270, 272, 273, 275, 276, 286, 287, 288, 290, 291, 292, 293, and 294.

Most preferred are the following compounds and salts and prodrugs thereof:
4-Amino-7-ethyl-5-fluoro-1-isobutyl-2-(2-(5-phosphono)furanyl)indole;
5-Chloro-6-fluoro-3,4-diisobutyl-2-(2-(5-phosphono)furanyl)indole;
5-Chloro-3-isobutyl-6,7-methyl-2-(2-(5-phosphono)furanyl)indole;
6-Chloro-1-isobutyl-7-thiomorpholinyl-2-(2-(5-phosphono)furanyl)indole;
7-Amino-5-chloro-6-fluoro-3-isobutyl-2-(2-(5-phosphono)furanyl)indole;
7-Amino-5-chloro-4-ethyl-6-fluoro-3-isobutyl-2-(2-(5-phosphone)furanyl)indole;
7-Amino-4-ethyl-6-hydroxy-5-chloro-3-isobutyl-2-(2-(5-phosphone)furanyl)indole;
4-Amino-7-ethyl-5-fluoro-1-isobutyl-6-methyl-2-(2-(5-phosphone)furanyl)indole;
4-Amino-5-fluoro-1-isobutyl-6-thiomethyl-2-(2-(5-phosphone)furanyl)indole;
7-Amino-3-cyclohexylethyl-4-ethyl-5,6-difluoro-2-(2-(5-phosphone)furanyl)indole;
7-Amino,6-fluoro-3,4-tetramethylene-2-(2-(5-phosphono)furanyl)indole;
7-Amino-3-(4-carboxyamidobutyl)-4-ethyl-6-fluoro-2-(2-(5-phosphono)furanyl)indole;
7-Amino-6-fluoro-3-isobutyl-2-(1-(3-hydroxy-3-phosphono)propyl)indole;
7-Amino-6-fluoro-3-isobutyl-2-(1-(3-phosphono-3-sulfuryl)propyl)indole;
7-Amino-6-fluoro-3-isobutyl-2-(1-(3-phosphono-3,3-difluoro)propyl)indole;
4-Amino-5-fluoro-1-isobutyl-2-(phosphonomethyleneaminocarbonyl)indole;
7-Methyl-5-chloro-3-isobutyl-2-(2-(5-phosphono)furanyl)indole;
9-Aza-7-methyl-3-isobutyl-2-(2-(5-phosphono)furanyl)indole;
9-Aza-7-amino-6-fluoro-3-isobutyl-2-(2-(5-phosphono)furanyl)indole;
9-Aza-7-amino-5-chloro-3-isobutyl-2-(2-(5-phosphono)furanyl)indole;
9-Aza-7-methyl-3-isobutyl-2-(1-(3-phosphono-3,3-difluoro)propyl)indole;
9-Aza-7-methyl-3-isobutyl-2-(1-(3-phosphono-3-hydroxy)propyl)indole;
9-Aza-7-methyl-3-isobutyl-2-(1-(3-phosphono-3-sulfuryl)propyl)indole;
9-Aza-7-methyl-3-isobutyl-2-(phosphonomethoxymethyl)indole;
9-Aza-7-amino-6-fluoro-3-isobutyl-2-(phosphonomethoxymethyl)indole;
9-Aza-7-amino-5-chloro-3-isobutyl-2-(phosphonomethoxymethyl)indole;

Synthesis of Preferred Compounds of Formula I

Synthesis of compounds encompassed by present invention typically includes some or all of the following steps: (1) preparation of the phosphonate prodrug; (2) deprotection of the phosphonate diester; (3) ring substitution of the indole heterocycle;

(4) modification of 2-substituent to introduce X group; (5) synthesis of the phosphonate substituted indole by ring closure; (6) synthesis of the linker (X group) phosphonate diester; and (7) synthesis of 2-nitro or 2-amino alkylbenzene derivatives.

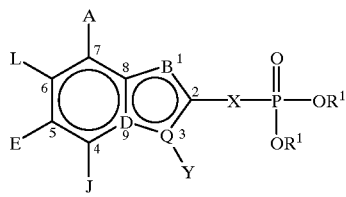

(1) Preparation of Phosphonate Prodrugs

Prodrug esters can be introduced at different stages of the synthesis. Most often these prodrugs are made from compounds of formula 1 where $R^1$ is hydrogen because of their lability. Advantageously, these prodrug esters can be introduced at an earlier stage, provided, they can withstand the reaction conditions of the subsequent steps.

Phosphonate esters can be prepared via reactions between the corresponding dichlorophosphonate and alcohols (Alexander et al. *Collect. Czech. Chem. Commun.*, 1994, 59: 1853). For example, the reaction of dichlorophosphonates with phenols or benzyl alcohols in the presence of bases (such as pyridine, triethylamine, etc) yields compounds of formula 1 where $R^1$ is aryl (Khamnei et al. *J. Med. Chem.*, 1996, 39: 4109; Serafinowska et al. *J. Med. Chem.*, 1995, 38:1372; De Lombaert et al. *J. Med. Chem.*, 1994, 37: 498) or benzyl groups (Mitchell et al. *J. Chem. Soc. Perkin Trans. 1*, 1992, 38: 2345). The disulfide-containing prodrug (Puech et al. *Antiviral Res.*, 1993, 22: 155) can also be prepared from the dichlorophosphonate and 2-hydroxyethyl disulfide under standard conditions.

Dichlorophosphonates can be generated from phosphonic acids under standard conditions, such as treatment with thionyl chloride (Starrett et al. *J. Med. Chem.*, 1994, 1857), oxalyl chloride (Stowell et al. *Tetrahedron Lett.*, 1990, 31: 3261), and phosphorus pentachloride (Quast et al. *Synthesis*, 1974, 490). Alternatively, dichlorophosphonates can be generated from disilyl phosphonate esters (Bhongle et al. *Synth. Commun.*, 1987, 17: 1071) and dialkyl phosphonate esters (Still et al. *Tetrahedron Lett.*, 1983, 24: 4405; Patois et al. *Bull. Soc. Chim. Fr.*, 1993, 130: 485).

Compounds of formula 1 where $R^1$ is hydrogen can also be alkylated with electrophiles (such as halides, sulfonates etc.) under substitution reaction conditions to give phosphonate esters. For example, compounds of formula 1 where $R^1$ is an acyloxymethyl group can be synthesized using acyloxyalkyl halides where the acyloxy group is for example, acetate, propionate, isobutyrate, pivalate, and benzoate, under standard conditions (Dickson et al. *J. Med. Chem.*, 1996, 39: 661; Iyer et al. *Tetrahedron Lett.*, 1989, 30: 7141; Srivastva et al. *Bioorg. Chem.*, 1984, 12: 118). Direct electrophilic alkylation of compounds of formula 1 where $R^1$ is H can also produce other prodrugs, such as compounds of formula 1 where $R^1$ is 3-phthalidyl, 2-oxo-4,5-didehydro-1,3-dioxolanemethyl, and 2-oxotetrahydrofuran-5-yl groups (Biller et al. U.S. Pat. No. 5,157,027; Serafinowska et al. *J. Med. Chem.*, 1995, 38: 1372; Starrett et al. *J. Med. Chem.*, 1994, 37: 1857; Martin et al. *J. Pharm. Sci.*, 1987, 76: 180; Alexander et al. *J. Med. Chem.*, 1996, 39: 480).

Other reagents are also useful in the preparation of phosphonate esters from phosphonic acids, such as N,N-dicyclohexyl-alkoxycarboxamidines (Elhaddadi et al. *Phosphorus Sulfur*, 1990, 54: 143; Hoffmann *Synthesis*, 1988, 62), and N,N-dimethylformamide dialkyl acetals (Alexander et al. *Collect. Czech. Chem. Commun.*, 1994, 59: 1853). Mitsunobu reactions (Mitsunobu, *Synthesis*, 1981, 1) can be used to couple phosphonic acids with alcohols to prepare phosphonate esters (Campbell, *J. Org. Chem.*, 1992, 52: 6331). Other acid coupling reaction conditions can also be used for the preparation of phosphonate esters, such as carbodiimide coupling reactions (Casara et al. *Bioorg. Med. Chem. Lett.*, 1992, 2, 145; Ohashi et al. *Tetrahedron Lett.*, 1988, 29, 1189), and benzotriazolyloxytris(dimethylamino) phosphonium salt coupling reactions (Campagne et al. *Tetrahedron Lett.*, 1993, 34: 6743).

$R^1$ can also be introduced at an early stage of synthesis, when feasible. For example, compounds of formula 1 where $R^1$ is phenyl can be prepared by phosphorylation of 2-furanylpurines via strong base treatment (e.g. LDA) followed by chlorodiphenylphosphonate, as shown in the following scheme. Alternatively, such compounds can be prepared by cyclization of 5-diphenylphosphono-2-furaldehyde as described in section 5.

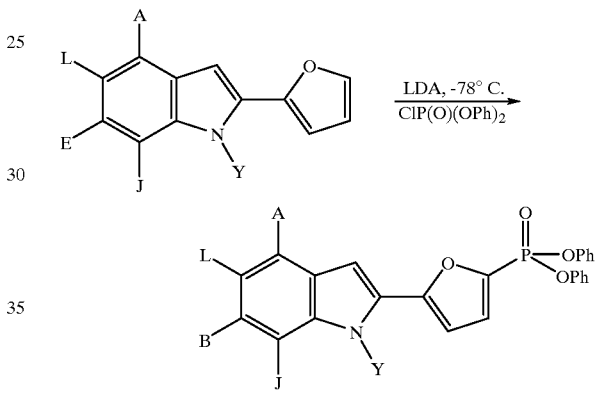

It is envisioned that compounds of formula 1 can be mixed phosphonate esters by combining the above described prodrugs (e.g. phenyl benzyl phosphonate esters, phenyl acyloxyalkyl phosphonate esters, etc.). For example, the chemically combined phenyl-benzyl prodrugs are reported by Meier et al. *Bioorg. Med. Chem. Lett.*, 1997, 7:99.

The cyclic phosphonate esters (such as cyclic 1,3-propane phosphonate diesters) of formula 1 can be prepared using the dichlorophosphonate coupling methods described earlier with various diols. Synthesis of 1,3-propanediols will be described in section (8).

(2) Deprotection of Phosphonate Esters

Compounds of formula 1 where $R^1$ is hydrogen may be prepared from phosphonate esters using known phosphate and phosphonate ester cleavage conditions. For example, alkyl phosphonate esters are generally cleaved through reaction with silyl halides followed by hydrolysis of the intermediate silyl phosphonate esters. Acid scavengers such as hexamethyldisilazane, and 2,6-lutidine are used in these reactions where substrates are acid sensitive. Various silyl halides can be used for this transformation, such as chlorotrimethylsilane (Rabinowitz, R., *J. Org. Chem.*, 1963, 28: 2975), bromotrimethylsilane (McKenna, C. E., et al *Tetrahedron Lett.*, 1977, 155), and iodotrimethylsilane (Blackburn, G. M., et al, *J. Chem. Soc., Chem. Commun.*, 1978, 870). Phosphonate esters can also be cleaved under strongly acidic conditions, such as hydrogen halides in acetic acid or water (Moffatt, J. G., et al U.S. Pat. No. 3,524,846, 1970). Phosphonate esters can also be converted to dichlorophosphonates with halogenating agents (such as phosphorus pentachloride, and thionyl chloride, Pelchowicz, Z., et al *J. Chem. Soc.,* 1961, 238) and subsequent hydrolysis to give phosphonic acids. Reductive reactions are useful in cleaving aryl and benzyl phosphonate esters. For example, phenyl phosphonate esters can be cleaved under hydrogenolysis conditions (Lejczak, B., et al, *Synthesis,* 1982, 412) or dissolving metal reduction conditions (Shafer, S. J., et al, *J. Am. Chem. Soc.,* 1977, 99: 5118); benzyl phosphonate esters can also be cleaved similarly (Elliott, R. L., et al, *J. Med. Chem.,* 1985, 28: 1208; Baddiley, J., et al, *Nature,* 1953, 171: 76). Electrochemical (Shono, T., et al, *J. Org. Chem.,* 1979, 44: 4508) and pyrolytic (Gupta, A., et al, *Synth. Commun.,* 1980, 10: 299) conditions have also been used to cleave various phosphonate esters.

3) Ring Substitution of Indole Heterocycles a) Introduction of the Y Group on the Heterocycle Introduction of the Y group on the pyrrole ring of the heterocycle is selectively achieved either at the carbon or on the nitrogen depending on the reaction conditions employed. This selective substitution of the Y group also defines regiochemistry of the A, L, E, J substituents on the benzene ring. Substitution at carbon (C-3) of the indole base can be achieved using palladium mediated chemistry (Heck, R. F., *Palladium Reagents in Organic Syntheses,* Academic Press, New York, 1985). In general, these reactions entail coupling C-3-iodo or -bromo indoles with boronic acids (*Pure & Appl. Chem.* 1991, 63: 419) and stannanes (Stille, J. K., et al, *J. Am. Chem. Soc.,* 1984, 106: 4630) in the presence of a palladium catalyst. Terminal acetylenes also react in the presence of copper (I) chloride and a palladium catalyst in a modified Stephens-Castro reaction (Sonogoshira, K., et al, *Tetrahedron Lett.,* 1975, 4467; Sakamoto, T. et al, *Synthesis,* 1983, 312). These alkynyl or alkenyl groups can be further transformed to alkenyl or alkyl substitution in a hydrogenation reaction by selection of a specific catalyst (Hutchins in Patai, *The Chemistry of Functional groups,* Wiley, New York, 1983, 571; Lindlar, H., et al, *Org. Synth. Coll. vol. V,* 1973, 880). Precursors for these coupling reactions can be made by halogenation at the C-3 position of indole using reagents such as N-halosuccinimide (Mistry, A. G., et al, *Tetrahedron Lett.,* 1986, 27: 1051) or pyridinium bromide perbromide (Erickson, K. L., et al, *Synth. Commun.,* 1981, 11: 253).

Introduction of a Y group at the N-1 position of the indole in compounds of formula 1 can be obtained by base-promoted alkylation with halides or sulfonates. Suitable bases include cesium carbonate or sodium hydride in an aprotic solvent (Guida, W. C., et al, *J. Org. Chem.,* 1981, 46: 3172; Kikugawa, Y., *Synthesis,* 1981, 124). Palladium catalysed N-alkylation of aryl iodides is also an applicable method to introduce Y groups (Wolfe, J. P., et al, *J. Org. Chem.,* 1996, 61: 1133). Alternatively, Mitsunobu reaction conditions can be used for N-1 substitution of the heterocycle (Mitsunobu, O., *Synthesis,* 1981, 1) using a variety of alcohols.

b) Substitution of the Benzene Ring of the Heterocycle

Substituents A, L, E and J in formula 1 can be introduced through reactions with indole or indole precursors. For example, substituents can be introduced on the heterocycle by substitution reactions (Hegedus, L. S., *Angew. Chem., Int. Ed. Engl.,* 1988, 27: 113) and further converted to required functional groups at this stage. Functional groups on the benzene ring are transformed after addition of the linker phosphonate and before the deprotection of the phosphonate diester.

Amino groups can be incorporated from nitro groups introduced through nitration reaction of the heterocycle (Masuda, T., et al, *Heterocycles,* 1987, 26, 1475). Nitration reactions of indoles result in a mixture of 4- and 6-regio isomers. Selectivity is obtained based on the other substituents on the benzene ring. The reduction of the nitro functional group is accomplished utilizing methods such as catalytic hydrogenation or chemical reduction (e.g., Sn/HCl). Alternatively, selective nitro group reduction is obtained by an aqueous sodium dithionate reaction. These conditions avoid hydrogenation of double bonds or reductive elimination of halogens (*Org. Syn. Coll. vol* 3, 1955, 69). Amines can be used to introduce other groups by diazotization reactions (Wulfman, in Patai *The Chemistry of Diazonium and Diazo Groups,* Wiley, New York, 1978, 286–297). Amine groups are also expected to facilitate other substitution reactions. Halogenation reaction of the heterocycle results in A, L, E, J substitution with 4- and 6-amino indole isomers. Bromo or iodo substituents can be further transformed into various substituents by transition metal chemistry (Heck, R. F., *Palladium Reagents in Organic Syntheses,* Academic Press, New York, 1985). The metallation strategy devised by Mayer et al. (*J. Org. Chem.,* 1986, 51: 5106) can be used to substitute different groups (e.g., $CO_2R$, COR, SMe, alkyl, aryl) at the 5-position.

(4) Modification of 2-substituent to Introduce X Group with Phosphonate

2-Substituted indole heterocycles can be converted to intermediates useful for the synthesis of compounds of formula 1. For example, compounds of formula 1 where X is methyleneaminocarbonyl may be obtained through a two-step procedure: indole-2-carboxylic esters are hydrolyzed using standard basic conditions (e.g. NaOH, $K_2CO_3$), and the resulting carboxylic acids are coupled to form amide linkages (Klausner, et al, *Synthesis,* 1972, 453; Bodansky, *The Practice of Peptide Synthesis,* Springer, New York, 1984) with amino substituted phosphonates utilizing known coupling agents such as Pyr-BOP (*Tetrahedron Lett.,* 1991, 32: 6387). Substituted indole-2-carboxylic esters can be prepared, e.g., by Reissert indole synthesis (Rosenmond, P., et al, *Chem. Ber.,* 1966, 99: 2504). The reaction involves condensation of 2-nitrotoluene with ethyl acetoacetate in presence of a mild base followed by a reductive cyclization.

Compounds of formula 1, where X is carboxypropyl or sulfonopropyl can be prepared from the reaction of 2-(2-iodoethyl)indole and corrosponding phosphonomethylcarboxylate or phosphonomethylsulfonate (Carretero et al., *Tetrahedron,* 1987, 43, 5125) in presence of base (eg. NaH) in polar aprotic solvents (eg. DMF). Substituted 2-(2-iodoethyl) indoles are prepared using known indole chemistry (e.g. Fischer indole synthesis). For the preparation of (x-phosphosulfonic acids, see Magnin, D. R. et al. *J. Med. Chem.* 1996, 39, 657.

Following well-reported literature procedures, other modifications of the 2-substituent of indoles can be used to synthesized various compounds of formula 1. For example, compounds of formula 1 where X is carbonylalkyl can be prepared from 2-carboxyalkylindoles via conversion of 2-carboxyalkylindoles to their corresponding acid chlorides, followed by Arbuzov reaction (*Chem. Rev.* 1984, 84: 577) with an alkyl phosphite to give 2-(2-dialkylphosphonocarbonylethyl)indoles. These α-ketophosphonates can be converted to the α-hydroxyphosphonates and (α,α-dihalophosphonates (Smyth, et al. *Tett. Lett.,* 1992, 33: 4137). For another way to synthesize these α,α-dihalophosphonates, see Martin et al. *Tett. Lett.,* 1992, 33, 1839.

3-Substituted indoles can be brominated selectively at the 2-position (Mistry, A. G., et al, *Tetrahedron Lett.,* 1986, 27: 1051). These intermediates are useful in the preparation of compounds where X is alkyl, aryl, alkylamino, arylamino, alkylthio, and arylthio. For example, the bromo can be replaced by such groups through a nucleophilic substitution reaction. Alternatively, phosphonate containing aromatic boronic acids, alkenyl stannanes or alkynyl X groups can be introduced in palladium mediated chemistry (Heck, R. F.,

*Palladium Reagents in Organic Syntheses,* Academic Press, New York, 1985). In an alternate metallation route, N-substituted or protected indoles undergo lithiation reaction at the 2-position which is useful in reactions with various electrophiles (*Synthesis,* 1991, 1079; *Heterocycles,* 1992, 33:173). Compounds of Formula 1 containing alkoxyalkyl as the X group can be synthesized from indole-2-carbinol intermediates obtained from the metallation reaction by quenching with an aldehyde (e.g. formaldehyde). The phosphonate groups are introduced by O-alkylation of hydroxyl with dialkoxy phosphonomethyl halide.

Compounds of formula 1 where X and Y substituents are fused to give annulated indoles can be made by two general methods. Alicyclic fused compounds can be made by Diels-Alder reaction of propargyl phosphonate with 3-vinyl indole derivatives (Pindur, U., *Heterocycles,* 1988, 27, 1253). Heterocyclic annulated indoles are synthesized from indole-2-methylene amines by Heck type reactions (*Tetrahedron Lett.,* 1996, 37: 2659) and also by ring closure reaction of tryptamine derivatives with aldehydes (Peng, S. Q. et al, *Liebigs. Ann. Chem.,* 1993, 2: 141; Pellegrini, C., et al, *Tetrahedron-Asymmetty,* 1994, 5: 1979). Phosphonate ester on the annulated heterocycle can be substituted by dialkoxyphosphonomethyl triflate (*Tetrahedron lett.,* 1986, 27: 1477).

(5) Synthesis of Phosphonate Substituted Indoles by Ring Closure

In another synthetic route, compounds of formula 1 are assembled by a ring closure reaction (Sundberg, R. J., *Indoles;* Academic press: San Diego, 1996).

One of such synthetic sequences involve the use of a phosphonate substituted aryl aldehyde. This aldehyde is condensed with a 2-nitrobenzyl ylide, which is generated in situ by treating 2-nitrobenzyltriphenyl phosphonium chloride with a base, e.g., potassium t-butoxide. The Wittig salt is made under usual conditions by reaction of 2-nitrobenzyl halide with triphenylphosphine (Murphy, P. B., et al, *Chem. Soc. Rev.* 1988, 17: 1; Maryanoff, B. E., et al, *Chem. Rev.* 1989, 89: 863).

conditions. This key step involves reduction of the nitro group and consequent addition of nitrene into the styryl double bond resulting in a substituted indole heterocycle as in formula 1 (Gelmi, M. L., et al, *J. Chem. Soc. Perkin I,* 1993, 969). 2-Vinylnitrobenzenes can also be prepared using other known methods, such as transition metal catalyzed coupling reactions between 2-halonitrobenzene and vinyl tin reagents. The above sequence can be used in the synthesis of compounds of formula 1, where X is an aryl group. Various phosphonate substituted aryl aldehydes can be prepared and used in this condensation.

These types of reductive cyclizations can also be achieved in the presence of a catalytic amount of $PdCl_2$—$SnCl_2$ under carbon monoxide atmosphere (Akazome, M., et al, *Chem. Lett.* 1992, 769). Another transition metal catalyzed synthetic approach by Larock, R. C., et. al, (*J. Am. Chem. Soc.,* 1991, 113: 6689) is also suitable to obtain compounds of formula 1 by a ring closure reaction.

Another ring closure method useful for indole synthesis is the palladium catalyzed cyclization reaction between 2-haloaniline and an alkyne, an alkene or a ketone (*J. Org. Chem.,* 1997, 62(9), 2676; 62(19), 6464, 6507). More importantly, this approach has been adopted for combinatorial synthesis of indoles on solid-phase which can be applied to the synthesis of indole FBPase inhibitors (*Tetrahedron Lett.,* 1997, 38(13), 2307).

Compounds of formula 1 are also prepared from o-toluidine trisubstituted amide cyclization, known as the Madelung indole synthesis (Brown, R. K., Indoles, Wiley: New York, 1972, Part 1; Houlihan, W. J., et al, *J. Org. Chem.,* 1981, 46: 4511). The amide is cyclized under modified Madelung reaction conditions in the presence of potassium ethoxide. The cyclization precursor is prepared by N-alkylation of amide followed by treatment with a nonnucleophilic base such as LDA and quenching the heteroaryl anion with chlorodialkylphosphonate. The starting amide is an addition product of substituted o-toluidine and acid chloride.

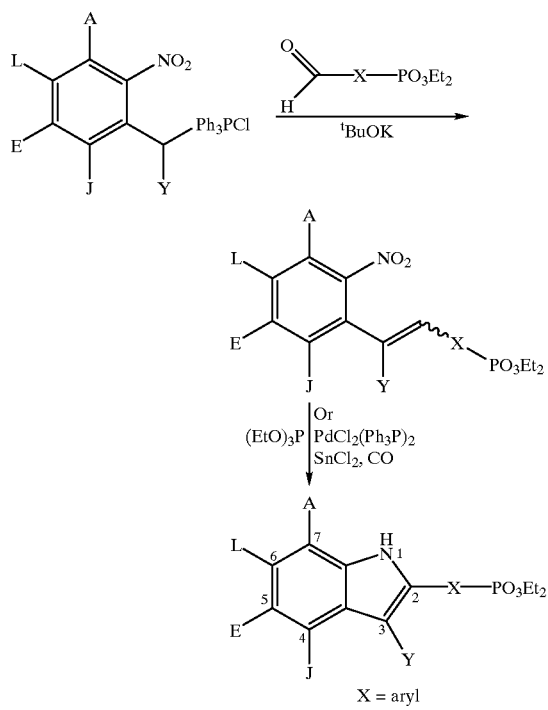

The diastereomeric mixture obtained from the condensation is then treated with triethylphosphite under refluxing

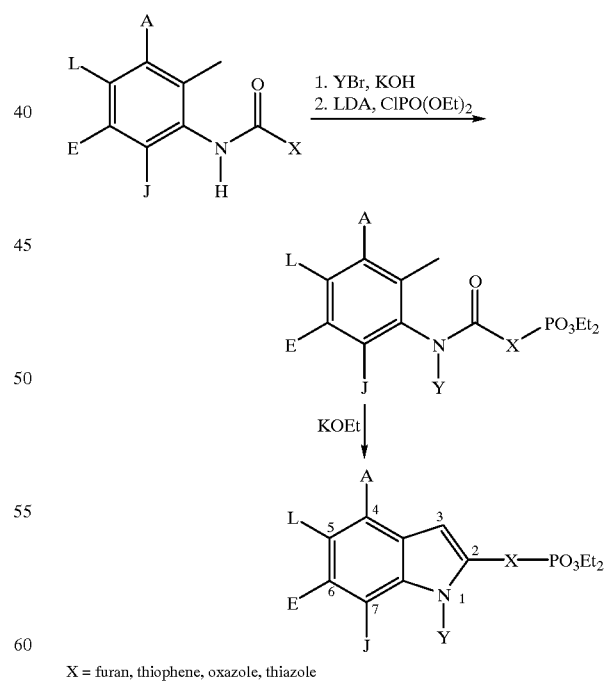

X = furan, thiophene, oxazole, thiazole

2-Acylaminobenzylidenephosphoranes also lead to indoles by an intramolecular Wittig reaction with the amide carbonyl group (Le Corre, M., et al, *Tetrahedron,* 1985, 41: 5313; Capuano, L., et al, *Chem. Ber.,* 1986, 119: 2069).

Alternatively, compounds of formula 1 can be obtained from silylated 2-amino benzylic bromide by treating o-toluidines with 2 equivalents of lithiating agent (e.g. n-BuLi) and TMSCI followed by bromination. Mixed organometallic intermediates are then prepared by reactions with Zn and a soluble copper salt CuCN.2LiCl. This reactive intermediate undergoes cyclization with an acyl chloride to give highly substituted compounds (Chen, H. G., et al, *Tetrahedron Lett.* 1989, 36: 4795; Bartoli, G., et al, *J. Chem. Soc. Chem. Commun.*, 1988, 807).

formation. Lewis acid catalyzed [3.3]-sigmatropic rearrangement of the hydrazone followed by cyclization of the enamine results in substituted indoles (Robinson, *The Fischer Indole Synthesis;* Wiley: New York, 1983). Zinc chloride is the most frequently used reagent among many known conditions, however, various metal halides or acids (eg. acetic acid, sulfuric acid) also promote the reaction (*Synthesis,* 1980, 2222). Mild acids are used in synthesis of C-2 and C-3 fused indoles known (Shimuzu, I., et al, *Chem. Pharm. Bull.,* 1971, 19: 2561).

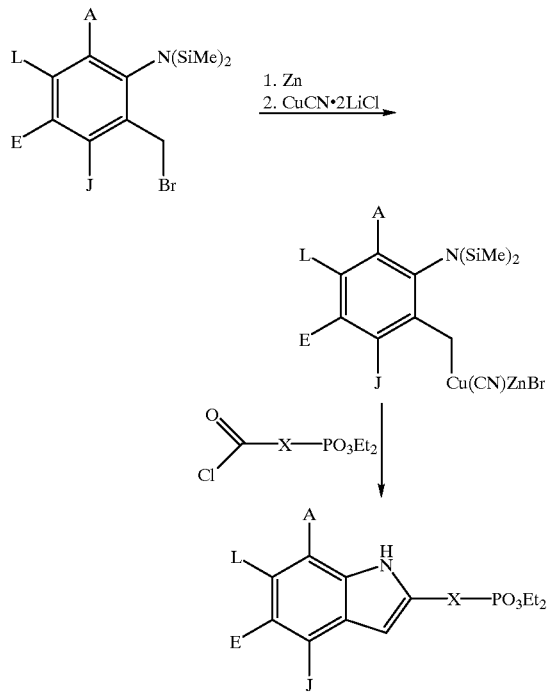

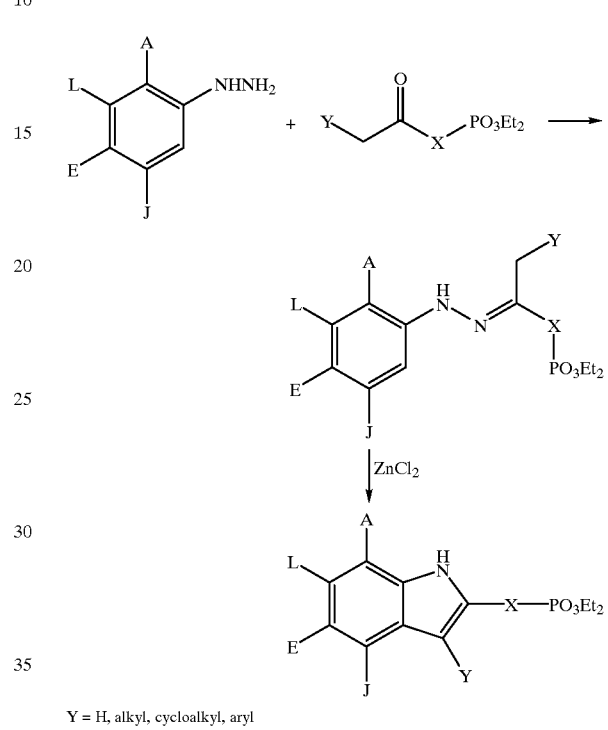

Alternatively, C-2 and C-3 substituted heterocycles of formula 1 can be made by condensation of a carboxylic acid ester with an organo dilithium intermediate of N-trimethylsilyl toluidine. Inverse addition of this organodilithium intermediate to a solution of aryl or alkyl ethyl ester results in a substituted indole heterocycle. (Smith, A, B., et al, *Tetrahedron Lett.* 1985, 26: 3757; Li, J. P., et al, *Synthesis,* 1988, 73).

Phosphonate substituted 9-azaindoles can also be synthesized via ring closure reactions (*Heterocycles,* 1997, 45(5), 897; *Synthesis,* 1996, 927). One method useful for 9-azaindole synthesis is the cyclization reaction between 2-aminopyridine and α-haloketones (e.g. α-bromoketone, α-chloroketone) and ketone derivatives as shown below (*J. Heterocycl. Chem.,* 1989, 26, 1875).

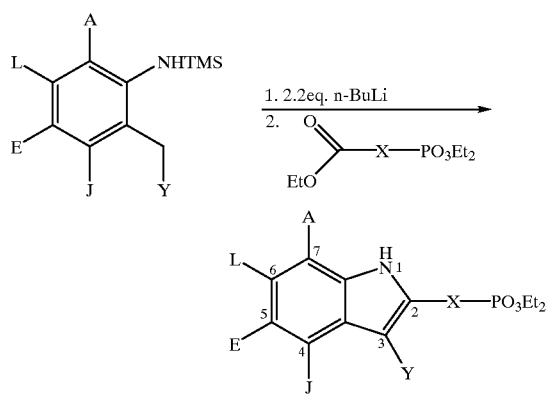

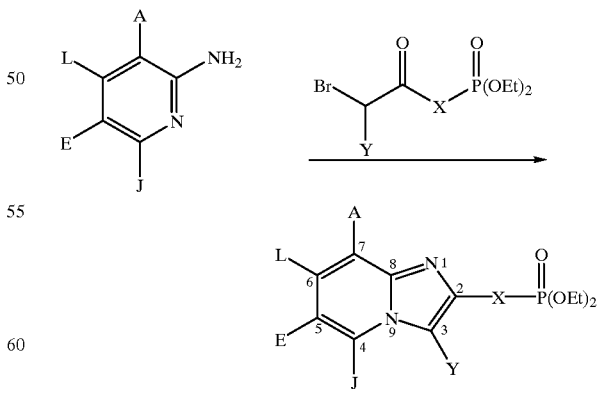

In another classical method known as the Fischer indole synthesis, compounds of formula 1 can be synthesized from aryl hydrazines with an aldehyde or ketone via hydrazone It is advantageous to have a phosphonate ester present in the α-bromoketone segment, however the phosphonate can also be introduced into the existing 9-azaindole. For example, 2-phosphonomethylaminocarbonyl-9-azaindole can be prepared from 2-ethoxycarbonyl-9-azaindole (available via cyclization reaction between 2-aminopyridine and ethyl bromopyruvate) as described in section 4 (Modification of 2-substituent to Introduce X Group with Phosphonate). 2-Phosphonomethoxymethyl-9-azaindole can also be synthesized from 2-ethoxycarbonyl-9-azaindole by the following sequence: reduction of 2-ethoxycarbonyl group to the 2-hydroxymethyl group, followed by alkylation with dialkylphosphonomethyl halide (preferably iodide) as described in section 4, supra.

(6) Synthesis of Linker (X group) Phosphonate Diester

Coupling of aromatic or aliphatic aldehydes, ketones, and carboxylic acid derivatives with attached phosphonate esters are particularly well-suited for compounds of formula 1 as described in the above section.

Aryl functionalized phosphonate linkers can be prepared by lithiation of an aromatic ring using methods well described in the iterature (Gschwend, *Org. React.* 1979, 26: 1; Durst, *Comprehensive Carbanion Chemistry,* Vol. 5, Elsevier, New York, 1984), followed by addition of phosphorylating agents (e.g. $ClPO_3R_2$). Phosphonate esters are also introduced by Arbuzov-Michaelis reaction of primary halides (Brill, T. B., *Chem Rev.,* 1984, 84: 577). Aryl halides undergo $Ni^{2+}$ catalyzed reaction with trialkylphosphites to give aryl phosphonate containing compounds (Balthazar, T. M., et al, *J. Org. Chem.,* 1980, 45: 5425). Aromatic triflates are known to result in phosphonates with $ClPO_3R_2$ in the presence of a palladium catalyst (Petrakis, K. S., et al, *J. Am. Chem. Soc.,* 1987, 109: 2831; Lu, X., et al, *Synthesis,* 1987, 726). In another method, aryl phosphonate esters are prepared from aryl phosphates under anionic rearrangement conditions (Melvin, L. S., *Tetrahedron Lett.,* 1981, 22, 3375; Casteel, D. A., et al, *Synthesis,* 1991, 691). The phosphate substituted linkers can also be converted to compounds of Formula 1. N-Alkoxy aryl salts with alkali metal derivatives of dialkyl phosphonate provide a general synthetic method for heteroaryl-2-phosphonate linkers (Redmore, D., *J. Org. Chem.,* 1970, 35, 4114).

In the linker phosphonate synthesis, aldehyde, ketone, or carboxylic acid functionalities can also be introduced after the phosphonate ester is formed. A lithiation reaction can be used to incorporate the aldehyde or ketone functionalities, although other methods known to generate aromatic aldehydes or ketones can be envisioned as well (e.g. Vilsmeier-Hack reaction, Reimar-Teimann reaction etc.; Pizey, *Synthetic Reagents,* 1974, 1: 1; Wynberg, H., et al, *Org. React.* 1982, 28: 1; palladium catalyzed coupling reaction of acid halides and organotin compounds). For example, for the lithiation reaction, the lithiated aromatic ring can be treated with reagents that directly generate the aldehyde (e.g. DMF, HCOOR, etc.)(Einchorn, J., et al, *Tetrahedron Lett.,* 1986, 27: 1791), or the ketone (e.g. Weinreb's amide, RCOOR'). The lithiated aromatic ring can also be treated with reagents that lead to a group that is subsequently transformed into the aldehyde or ketone group using known chemistry (synthesis of aldehyde and ketone from alcohol, ester, cyano, alkene, etc.). It is also envisioned that the sequence of these reactions can be reversed, i.e. the aldehyde and ketone moieties can be incorporated first, followed by the phosphorylation reaction. The order of the reaction will depend on reaction conditions and protecting groups. Prior to the phosphorylation it is also envisioned that it may be advantageous to protect the aldehyde or ketone using well-known methods (acetal, aminal, hydrazone, ketal, etc.), and then the aldehyde or ketone is unmasked after phosphorylation. (*Protective Groups in Organic Synthesis,* Greene, T. W., 1991, Wiley, New York).

(7) Synthesis of 2-nitro or 2-amino Alkyl Benzene Derivatives

Building blocks for substituted benzene nuclei are obtained by nitration of alkyl benzenes. These compounds can be further transformed to 2-amino alkyl benzenes. 2-Amino alkyl benzenes can also be obtained from alkylation of aniline derivatives. A variety of substitutions on these groups can be made following known chemistry (March, J., *Advanced Organic Chemistry,* J. Wiley, New York, 1992, 501–568). N-Acyl and N-alkyl precursors can be obtained by methods mentioned earlier.

(8) Synthesis of the 1,3-Propane Diols Used in the Preparation of Certain Prodrugs The discussion of this step includes various synthetic methods for the preparation of the following types of propane-1,3-diols: i) 1-substituted; ii) 2-substituted; and iii) 1,2- or 1,3-annulated. Different groups on the prodrug part of the molecule i.e., on the propane diol moiety can be introduced or modified either during the synthesis of the diols or after the synthesis of the prodrugs.

i) 1-Substituted 1,3-Propane Diols

Propane-1,3-diols can be synthesized by several well known methods in the literature. Aryl Grignard additions to 1-hydroxypropan-3-al gives 1-aryl-substituted propane-1,3-diols (path a). This method will enable conversion of various substituted aryl halides to 1-arylsubstituted-1,3-propane diols (Coppi, et. al., *J. Org. Chem.,* 1988, 53, 911). Aryl halides can also be used to synthesize 1-substituted propanediols by Heck coupling of 1,3-diox-4-ene followed by reduction and hydrolysis (Sakamoto, et. al., *Tetrahedron Lett.,* 1992, 33, 6845). A variety of aromatic aldehydes can be converted to 1-substituted-1,3-propane diols by vinyl Grignard addition followed by hydroboration (path b). Substituted aromatic aldehydes are also useful for lithium-t-butylacetate addition followed by ester reduction (path e) (Turner., *J. Org. Chem.,* 1990, 55 4744). In another method, commercially available cinnamyl alcohols can be converted to epoxy alcohols under catalytic asymmetric epoxidation conditions. These epoxy alcohols are reduced by Red-Al to result in enantiomerically pure propane-1,3-diols (path c). Alternatively, enantiomerically pure 1,3-diols can be obtained by chiral borane reduction of hydroxyethyl aryl ketone derivatives (Ramachandran, et. al., *Tetrahedron Lett.,* 1997, 38 761). Pyridyl, quinoline, and isoquinoline propan-3-ol derivatives can be oxygenated to 1-substituted propan-1,3-diols by N-oxide formation followed by rearrangement under acetic anhydride conditions (path d) (Yamamoto, et. al., *Tetrahedron* 1981, 37, 1871).

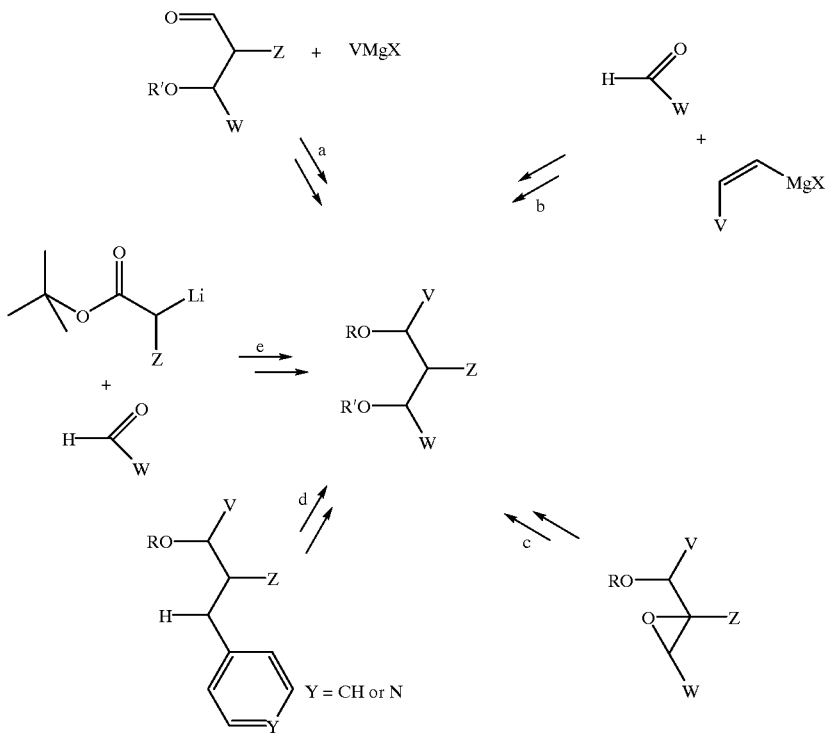

ii) 2-Substituted 1,3-Propane Diols:

Various 2-substituted propane-1,3-diols can be made from commercially available 2-(hydroxymethyl)-1,3-propane diol. Triethyl methanetricarboxylate can be converted to the triol by complete reduction (path a) or diol-monocarboxylic acid derivatives can be obtained by partial hydrolysis and diester reduction (Larock, *Comprehensive Organic Transformations*, VCH, New York, 1989). Nitrotriol is also known to give the triol by reductive elimination (path b) (Latour, et. al., *Synthesis*, 1987, 8, 742). The triol can be derivatized as a mono acetate or carbonate by treatment with alkanoyl chloride, or alkylchloroformate, respectively (path d) (Greene and Wuts, *Protective Groups in Organic Synthesis*, John Wiley, New York, 1990). Aryl substitution effected by oxidation to the aldehyde followed by aryl Grignard additions (path c) and the aldehyde can also be converted to substituted amines by reductive amination reactions (path e).

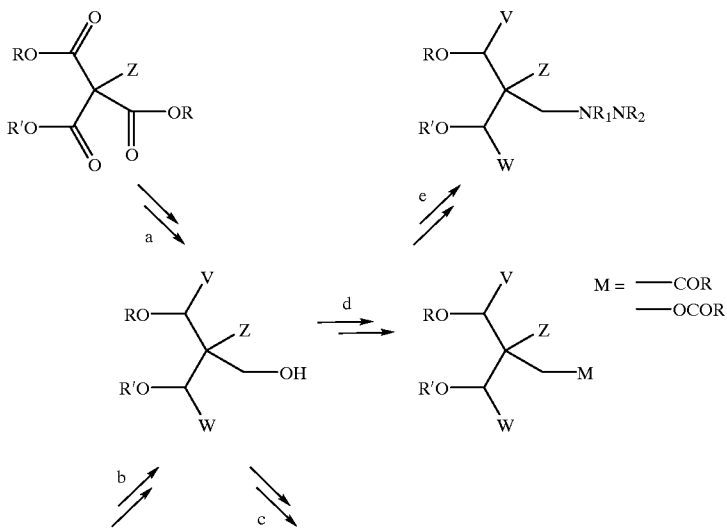

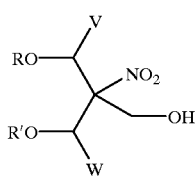 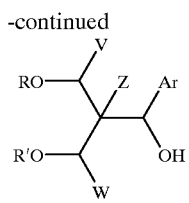

iii) Annulated 1,3-Propane Diols:

Prodrugs of formula 1 where V-Z or V-W are fused by three carbons are made from cyclohexane diol derivatives. Commercially available cis, cis-1,3,5-cyclohexane triol can be used for prodrug formation. This cyclohexanetriol can also be modified as described in the case of 2-substituted propan-1,3-diols to give various analogues. These modifications can either be made before or after formation of prodrugs. Various 1,3-cyclohexane diols can be made by Diels-Alder methodology using pyrone as the diene (Posner, et. al., *Tetrahedron Lett.,* 1991, 32, 5295). Cyclohexyl diol derivatives are also made by nitrile oxide olefin-additions (Curran, et. al., *J. Am. Chem. Soc.,* 1985, 107, 6023). Alternatively, cyclohexyl precursors can be made from quinic acid (Rao, et. al., *Tetrahedron Lett.,* 1991, 32, 547.)

Formulations

Compounds of the invention are administered orally in a total daily dose of about 0.1 mg/kg/dose to about 100 mg/kg/dose, preferably from about 0.3 mg/kg/dose to about 30 mg/kg/dose. The most preferred dose range is from 0.5 to 10 mg/kg (approximately 1 to 20 nmoles/kg/dose). The use of time-release preparations to control the rate of release of the active ingredient may be preferred. The dose may be administered in as many divided doses as is convenient. When other methods are used (e.g. intravenous administration), compounds are administered to the affected tissue at a rate from 0.3 to 300 nmol/kg/min, preferably from 3 to 100 nmoles/kg/min. Such rates are easily maintained when these compounds are intravenously administered as discussed below.

For the purposes of this invention, the compounds may be administered by a variety of means including orally, parenterally, by inhalation spray, topically, or rectally in formulations containing pharmaceutically acceptable carriers, adjuvants and vehicles. The term parenteral as used here includes subcutaneous, intravenous, intramuscular, and intraarterial injections with a variety of infusion techniques. Intraarterial and intravenous injection as used herein includes administration through catheters. Oral administration is generally preferred.

Pharmaceutical compositions containing the active ingredient may be in any form suitable for the intended method of administration. When used for oral use for example, tablets, troches, lozenges, aqueous or oil suspensions, dispersible powders or granules, emulsions, hard or soft capsules, syrups or elixirs may be prepared. Compositions intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients may be, for example, inert diluents, such as calcium or sodium carbonate, lactose, calcium or sodium phosphate; granulating and disintegrating agents, such as maize starch, or alginic acid; binding agents, such as starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

Formulations for oral use may be also presented as hard gelatin capsules where the active ingredient is mixed with an inert solid diluent, for example calcium phosphate or kaolin, or as soft gelatin capsules wherein the active ingredient is mixed with water or an oil medium, such as peanut oil, liquid paraffin or olive oil.

Aqueous suspensions of the invention contain the active materials in admixture with excipients suitable for the manufacture of aqueous suspensions. Such excipients include a suspending agent, such as sodium carboxymethylcellulose, methylcellulose, hydroxypropyl methylcelluose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxybenzoate, one or more coloring agents, one or more flavoring agents and one or more sweetening agents, such as sucrose or saccharin.

Oil suspensions may be formulated by suspending the active ingredient in a vegetable oil, such as arachis oil, olive oil, sesame oil or coconut oil, or in a mineral oil such as liquid paraffin. The oral suspensions may contain a thickening agent, such as beeswax, hard paraffin or cetyl alcohol. Sweetening agents, such as those set forth above, and flavoring agents may be added to provide a palatable oral preparation. These compositions may be preserved by the addition of an antioxidant such as ascorbic acid.

Dispersible powders and granules of the invention suitable for preparation of an aqueous suspension by the addition of water provide the active ingredient in admixture with a dispersing or wetting agent, a suspending agent, and one or more preservatives. Suitable dispersing or wetting agents and suspending agents are exemplified by those disclosed above. Additional excipients, for example sweetening, flavoring and coloring agents, may also be present.

The pharmaceutical compositions of the invention may also be in the form of oil-in-water emulsions. The oily phase may be a vegetable oil, such as olive oil or arachis oil, a mineral oil, such as liquid paraffin, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan monooleate, and condensation products of these partial esters with ethylene oxide, such as polyoxyethylene sorbitan monooleate. The emulsion may also contain sweetening and flavoring agents.

Syrups and elixirs may be formulated with sweetening agents, such as glycerol, sorbitol or sucrose. Such formulations may also contain a demulcent, a preservative, a flavoring or a coloring agent.

The pharmaceutical compositions of the invention may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, such as a solution in 1,3-butane-diol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

The amount of active ingredient that may be combined with the carrier material to produce a single dosage form will vary depending upon the host treated and the particular mode of administration. For example, a time-release formulation intended for oral administration to humans may contain 20 to 2000 $\mu$mol (approximately 10 to 1000 mg) of active material compounded with an appropriate and convenient amount of carrier material which may vary from about 5 to about 95% of the total compositions.

It is preferred that the pharmaceutical composition be prepared which provides easily measurable amounts for administration. For example, an aqueous solution intended for intravenous infusion should contain from about 0.05 to about 50 $\mu$mol (approximately 0.025 to 25 mg) of the active ingredient per milliliter of solution in order that infusion of a suitable volume at a rate of about 30 mL/hr can occur.

As noted above, formulations of the present invention suitable for oral administration may be presented as discrete units such as capsules, cachets or tablets each containing a predetermined amount of the active ingredient; as a powder or granules; as a solution or a suspension in an aqueous or non-aqueous liquid; or as an oil-in-water liquid emulsion or a water-in-oil liquid emulsion. The active ingredient may also be administered as a bolus, electuary or paste.

A tablet may be made by compression or molding, optionally with one or more accessory ingredients. Compressed tablets may be prepared by compressing in a suitable machine the active ingredient in a free flowing form such as a powder or granules, optionally mixed with a binder (e.g., povidone, gelatin, hydroxypropylmethyl cellulose), lubricant, inert diluent, preservative, disintegrant (e.g., sodium starch glycolate, cross-linked povidone, cross-linked sodium carboxymethyl cellulose) surface active or dispersing agent. Molded tablets may be made by molding in a suitable machine a mixture of the powdered compound moistened with an inert liquid diluent. The tablets may optionally be coated or scored and may be formulated so as to provide slow or controlled release of the active ingredient therein using, for example, hydroxypropyl methylcellulose in varying proportions to provide the desired release profile. Tablets may optionally be provided with an enteric coating, to provide release in parts of the gut other than the stomach. This is particularly advantageous with the compounds of formula 1 when such compounds are susceptible to acid hydrolysis.

Formulations suitable for topical administration in the mouth include lozenges comprising the active ingredient in a flavored base, usually sucrose and acacia or tragacanth; pastilles comprising the active ingredient in an inert base such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

Formulations suitable for vaginal administration may be presented as pessaries, tampons, creams, gels, pastes, foams or spray formulations containing in addition to the active ingredient such carriers as are known in the art to be appropriate.

Formulations suitable for parenteral administration include aqueous and non-aqueous isotonic sterile injection solutions which may contain antioxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose sealed containers, for example, ampoules and vials, and may be stored in a freeze-dried (lyophilized) condition requiring only the addition of the sterile liquid carrier, for example water for injections, immediately prior to use. Injection solutions and suspensions may be prepared from sterile powders, granules and tablets of the kind previously described.

Preferred unit dosage formulations are those containing a daily dose or unit, daily sub-dose, or an appropriate fraction thereof, of a fructose 1,6-bisphosphatase inhibitor compound.

It will be understood, however, that the specific dose level for any particular patient will depend on a variety of factors including the activity of the specific compound employed; the age, body weight, general health, sex and diet of the individual being treated; the time and route of administration; the rate of excretion; other drugs which have previously been administered; and the severity of the particular disease undergoing therapy, as is well understood by those skilled in the art.

Utility

FBPase inhibitors at the AMP site may be used to treat diabetes mellitus, lower blood glucose levels, and inhibit gluconeogenesis.

FBPase inhibitors at the AMP site may also be used to treat excess glycogen storage diseases. Excessive hepatic glycogen stores are found in patients with some glycogen storage diseases. Since the indirect pathway contributes significantly to glycogen synthesis (Shulman, G. I. *Phys. Rev.* 1992, 72:1019–1035, inhibition of the indirect pathway (gluconeogenesis flux) is expected to decrease glycogen overproduction.

FBPase inhibitors at the AMP site may also be used to treat or prevent diseases associated with increased insulin levels. Increased insulin levels are associated with an increased risk of cardiovascular complications and atherosclerosis (Folsom, et al., *Stroke,* 1994, 25, 66–73; Howard, G. et al., *Circulation* 1996, 93, 1809–1817). FBPase inhibitors are expected to decrease postprandial glucose levels by enhancing hepatic glucose uptake. This effect is postulated to occur in individuals that are non-diabetic (or pre-diabetic, i.e. without elevated HGO or fasting blood glucose levels). Increased hepatic glucose uptake will decrease insulin secretion and thereby decrease the risk of diseases or complications that arise from elevated insulin levels.

The compounds of this invention and their preparation can be understood further by the examples which illustrate some of the processes by which these compounds are prepared. These examples should not however be construed as specifically limiting the invention and variations of the invention, now known or later developed, are considered to fall within the scope of the present invention as hereinafter claimed.

EXAMPLES

Example 1

Preparation of 2-(phosphonomethylaminocarbonyl) indoles

Step A. To a solution of 3.0 g (12.8 mmol) ethyl-7-nitroindole-2-carboxylate in 10 mL of methanol was added 10 mL of 1 N sodium hydroxide and the reaction mixture was heated at 90° C. for 90 minutes. The solution was acidified with 3N hydrochloric acid and the solid formed was filtered and washed with water. The solid 1.9 g (9.2 mmol, 72.1%) was dried to give a light yellow powder.

Step B. To a solution of 7.5 g (36.4 mmol) 7-nitroindole-2-carboxylic acid, 20 mL methylene chloride, 6.5 mL diisopropylethyl amine and 5.8 mL (40.0 mmol) diethyl (aminomethyl)phosphonate was added 18.9 g (36.4 mmol) PyBOP. The reaction contents were stirred at room temperature for four hours, filtered and eluted through a pad of silica with ethyl acetate. The filtrate was evaporated under reduced pressure and was resuspended in a minimum amount of ethylacetate. The resulting solid was filtered and dried to give 10.1 g (28.4 mmol, 78%) of a light yellow powder.

Step C. To a solution of 0.53 g (1.49 mmol) 2-(diethylphosphonomethylaminocarbonyl)-7-nitroindole in 7 mL acetonitrile was added 2 mL of bromotrimethylsilane at 0° C. The reaction mixture was allowed to stir at room temperature overnight. The solvent and excess bromotrimethylsilane were removed under reduced pressure and 10 mL of a 1/1 mixture of acetone/water was added and stirred for 24 hours at room temperature. A precipitate formed and the solid was filtered and dried to give 0.45 g (1.47 mmol, 99%) of 2-(phosphonomethylaminocarbonyl)-7-nitroindole.

Step D. To a solution of 2-(phosphonomethylaminocarbonyl)-7-nitroindole (1.49 mmol) in 10 mL of 50 mmolar sodium bicarbonate was added 0.25 mg 10% Pd/C under hydrogen atmosphere. The solution was stirred at room temperature for 30 minutes. The contents were filtered over Celite and the filtrate was evaporated under reduced pressure to give 0.3 g (1.1 mmol, 75%) of 7-amino-2-(phosphonomethylaminocarbonyl)indoles.

The following compounds were prepared in this manner:

1.1: 7-Amino-2-(phosphonomethylaminocarbonyl)indole. mp >250° C.; Anal. cald. for $C_{10}H_{12}N_3O_4P+1H_2O$: C: 41.82; H: 4.91; N: 14.63. Found: C: 41.87; H: 4.41; N: 14.09.

1.2: 2-(Phosphonomethylaminocarbonyl)indole. mp 142° C.; Anal. cald. for $C_{10}H_{11}N_2O_4P+1.35H_2O$: C: 42.97; H: 5.05; N: 9.55. Found: C: 42.95; H: 4.48; N: 9.55.

1.3: Disodium 5-methoxy-2-(phosphonomethylaminocarbonyl)indole. mp 279° C.; Anal. cald. for $C_{11}H_{11}N_2O_5PNa_2+2.5H_2O+2HOAc$: C: 36.52; H: 4.90; N: 5.68. Found: C: 36.72; H: 4.86; N: 5.65.

1.4: Sodium 1-methyl-2-(phosphonomethylaminocarbonyl) indole. mp 165° C.; Anal. cald. for $C_{11}H_{12}N_2O_4PNa+0.2H_2O+0.6HOAc+0.1CH_3CN$: C: 44.1 1; H: 4.39; N: 9.35. Found: C: 44.45; H: 4.49; N: 8.97.

Example 2

Preparation of 2-phosphonomethylamido-3-phenyl-7-aminoindole

Steps A and B were the same as in Example 1.

Step C. To a solution of 35 mL of methanol, sodium hydroxide (19.2 mmol) in 2 mL of water, 2-[diethyl(carboxymethyl)phosphonate]-7-nitroindole (11.2 mmol) was added a 5 mL 1/1 methanol/water solution of potassium iodide (20.5 mmol ) and iodine (22.8 mmol). The mixture was stirred for 30 min and the volume was reduced under reduced pressure. The resultant solid was filtered, washed with water and acetonitrile to yield 2-diethyl phosphonomethylaminocarbonyl-3-iodo-7-nitroindole (11 mmol, 98%) as a light yellow powder.

Step D. To a solution of 2-diethyl phosphonomethylaminocarbonyl-3-iodo-7-nitroindole (0.42 mmol) and 3 mL diglyme was added 1 mL saturated sodium carbonate solution, and 26 mg (0.23 mmol) tetrakis(triphenylphosphine) palladium. To this solution was further added a solution of phenylboronic acid (2.3 mmol) in 1 mL ethanol. The reaction was heated to 120° C. and refluxed overnight. The solvent was removed under reduced pressure and the solid obtained was chromatographed ($SiO_2$, 33% ethyl acetate/hexane, 100% ethyl acetate, gradient elution) to give 2-diethylphosphonomethylaminocarbonyl-3-phenyl-7-nitroindole (0.36 mmol).

Steps E. 2-Diethylphosphonomethylaminocarbonyl-3-phenyl-7-nitroindole was subjected to procedures of Step C and D in Example 1 to give 7-amino-3-phenyl-2-(phosphonomethylaminocarbonyl)indole (2.1). mp >250° C.; Anal. Cald. for $C_{16}H_{16}N_3O_4P+1.25H_2O$: C: 52.28; H; 5.0; N: 11.43. Found: C: 52.56; H: 4.85; N: 10.84.

Example 3

Preparation of 2-phosphonomethylamido-3-phenethyl-7-aminoindole

Steps A and B were the same as in Example 1 and Step C was the same as in Example 2.

Step D. To a solution of 1.0 g (2.1 mmol) of 2-diethylphosphonomethylamido-3-iodo-7-nitroindole in 70 mL of acetonitrile and 20 mL of triethylamine was added 1.0 mL (11 mmol) phenylacetylene, followed by 25 mg (0.13 mmol) of CuI and 20 mg (0.028 mmol) of bis(triphenylphosphine)dichloropalladium. The reaction was heated to 60° C. for 15 min and the solvents were removed under reduced pressure. The resultant solid was chromatographed on silica with 50% ethyl acetate/hexane to pure ethyl acetate yielding 0.74 g (1.27 mmol, 61%) of 2-diethylphosphonomethylaminocarbonyl-3-phenylacetylido-7-nitroindole.

Steps E. 2-Diethylphosphonomethylaminocarbonyl-3-phenylacetylido-7-nitroindole was subjected to procedures of Step C and D in Example 1 to give 7-amino-3-(2-phenethyl)-2-(phosphonomethylaminocarbonyl)indole (3.1). mp >250° C.; Anal. Cald. for $C_{18}H_{20}N_3O_4P+1.5H_2O$: C: 54.00; H: 5.79; N; 10.5. Found: C: 54.55; H: 5.52; N: 9.47.

Example 4

Preparation of 5-diethylphosphono-2-furaldehyde

Step A. A solution of 2-furaldehyde diethyl acetal (1 mmol) in THF was treated with n-BuLi (1 mmol) at −78° C. After 1 h, diethyl chlorophosphate (1.2 mmol) was added and stirred for 40 min. Extraction and evaporation gave a brown oil.

Step B. The resulting brown oil was treated with 80% acetic acid and heated at 90° C. for 4 h. Extraction and chromatography gave the titled compound as a clear oil.

Alternatively this aldehyde can be prepared from furan as described below.

Step C. A solution of furan (1 mmol) in diethyl ether was treated with tetramethylethylenediamine (1 mmol) and n-BuLi (2 mmol) at −78° C. The solution was stirred for 0.5 h at −78° C. and diethyl chlorophosphate was added and stirred for another 1 h. Extraction and distillation gave 2-diethylfuranphosphonate as clear oil.

Step D. A solution of 2-diethylfuranphosphonate (1 mmol) in tetrahydrofuran was treated with LDA (1.12 mmol) at −78° C. for 20 min. To the reaction was then added methyl formate (1.5 mmol) and stirred for 1 h. Extraction and chromatography gave the title compound as a clear, yellow oil.

Experimental procedures for a third approach are as follows:

Step E. To a solution of 168 g (1.75 mol) 2-furaldehyde in 500 mL toluene was added 215 mL (1.75 mol) of N,N'-dimethylethylenen diamine. The solution was refluxed using a Dean Stark trap to remove $H_2O$. After 2 h of reflux, the solvent was removed under reduced pressure. The resulting dark mixture was vacuum distilled (3 mm Hg) and the fraction at 59–61° C. was collected to yield 247.8 g (85%) of a clear, colorless oil.

Step F. A solution of 33.25 g (0.2 mol) furan-2-(N,N'-dimethylimidazolidine) and 30.2 mL (0.2 mol) tetramethylethylenediamine in 125 mL THF was cooled in a dry ice/IPA bath. A solution of 112 mL n-BuLi in hexane(0.28 mol, 2.5 M) was added dropwise, maintaining temperature between −50 and −40° C. during addition. The reaction was allowed to warm to 0° C. over 30 minutes and was maintained at 0° C. for 45 min. The reaction was then cooled in a dry ice/IPA bath to −55° C. This cooled solution was transferred to a solution of 34.7 mL (0.24 mol) diethylchlorophosphate in 125 mL THF cooled in a dry ice/IPA bath over 45 min maintaining the reaction temperature between −50 and −38° C. The reaction was stirred at room temperature overnight. The reaction mixture was evaporated under reduced pressure. Ethyl acetate (500 mL) and $H_2O$ (50 mL) were added to the residue and the layers separated. The $H_2O$ layer was washed with ethyl acetate. The ethyl acetate layers were combined, dried over magnesium sulfate and evaporated under reduced pressure to yield 59.6 g (98%) of a brown oil.

Step G. To a solution of 59.6 g 5-diethylphosphonofuran-2-(N,N'-dimethylimidazolidine) in 30 mL $H_2O$ was added 11.5 mL of conc. $H_2SO_4$ dropwise until pH=1. The aqueous reaction mixture was extracted with ethyl acetate. The ethyl acetate layer was washed with saturated sodium bicarbonate, dried over magnesium sulfate and evaporated to a brown oil. The brown oil was added to a silica column and was eluted with hexane/ethyl acetate. Product fractions were pooled and evaporated under reduced pressure to yield a dark yellow oil, 28.2 g (62%).

Example 5

Preparation of 2-(5-phosphono)furanylindole

Step A. To a solution of 2-nitrobenzyl chloride (10 mmol) in toluene (50 mL) was added triphenylphosphine (11 mmol). The resulting mixture was refluxed for 24 h. The reaction was cooled to 0° C. and precipitated product was filtered, washed with toluene (100 mL) and dried overnight in vacuo to give pure phosphonium salt (2.73 g, 63%).

Step B. 1 M Potassium t-butoxide in THF (1.5 mmol) was added to a dispersion of phosphonium salt (1.8 mmol) in THF (10 mL) at 0° C. The reaction developed a deep orange ylide color and was allowed to stir for 15 min at 0° C. Aldehyde (1.5 mmol) was added in THF (3 mL) to the reaction and stirred at room temperature for an additional 30 min. The reaction was diluted with methylene chloride (100 mL), washed with water (2×25 mL), brine and dried (anhydrous $Na_2SO_4$). The solvent was evaporated and the crude mixture was chromatographed with 25% ethyl acetate-methylene chloride to give pure coupled product (400 mg, 60%).

Step C. To the nitro-olefin (1.70 mmol) was added triethyl phosphite (10 mL) and the reaction was refluxed for 2 h. The reaction was concentrated under vacuum at 50° C., and was azeotroped with toluene. The crude product was chromatographed with 25% ethyl acetate-methylene chloride to give 2-(2-(5-diethylphosphono)furanyl)indole (250 mg, 45%).

Step D. 2-(2-(5-Diethylphosphono)furanyl)indole was subjected to Step C in Example 1 to give 2-(2-(5-phosphono)furanyl)indole (5.1). mp 118–121° C.; Anal. cald. for $C_{12}H_{10}NPO_4+1H_2O$: C: 51.26; H: 4.30; N: 4.98. Found: C: 50.77; H: 4.08; N: 4.87.

Example 6

Preparation of 1-Isobutyl-2-(2-(5-phosphono)furanyl)indole

Steps A, B and C were the same as in Example 5. Step D. To a solution of 2-(2-diethylphosphono-5-furanyl)indole (0.62 mmol) and 2-bromomethylpropane (1 mmol) in DMF (5 mL), was added cesium carbonate (1 mmol) at 25° C. The solution was heated to 85° C. and stirred overnight. Evaporation and chromatography ($SiO_2$, 50% ethyl acetate/hexane) gave 1-isobutyl-2-(2-(5-phosphono)furanyl)indole (6.1, 170 mg) as a light yellow solid. mp 122–126° C.; Anal. cald. for $C_{16}H_{18}NPO_4+0.35H_2O$: C: 59.02; H: 5.79; N: 4.30. Found: C: 59.17; H: 5.82; N: 4.09.

Example 7

Preparation of 3-bromo-2-(2-(5-phosphono)furanyl)indole

Steps A, B and C were the same as in Example 5.

Step D. To a solution of 2-(2-(5-diethylphosphono)furanyl)indole (0.62 mmol) in DMF(6 mL) was added N-bromosuccinimide (0.7 mmol) at 0° C. The reaction was stirred for 1 h at 0° C. and was concentrated under vacuum. The crude product was chromatographed ($SiO_2$, 25% ethyl acetate-methylene chloride) to give 3-bromo-2-(2-(5-diethylphosphono)furanyl)indole (205 mg).

Step E. 3-Bromo-2-(2-(5-diethylphosphono)furanyl) indole was subjected to Step C in Example 1 to give 2-(2-(5-phosphono)furanyl)-3-bromoindole (7.1). mp >220° C.; Anal. cald. for $C_{12}H_9NPO_4Br+0.5H_2O$: C: 41.05; H: 2.87; N: 3.99. Found: C: 41.20; H: 2.78; N: 3.96.

Step F. 3-Bromo-2-(2-(5-diethylphosphono)furanyl) indole was sujected to Step D in Example 2 and Step C in Example 1 to give 3-phenyl-2-(2-(5-phosphono)furanyl) indole (7.2). mp 178–182° C.; Anal. cald. for $C_{18}H_{14}NPO_4+0.75H_2O+0.2HBr$: C: 58.59; H: 4.29; N: 3.80. Found: C: 58.19; H: 4.10; N: 3.72.

Example 8

Preparation of 3-Chloro-2-(2-(5-phosphono)furanyl) indole

Steps A, B and C were the same as in Example 5.

Step D. To a solution of 2-(2-(5-diehylphosphono) furanyl)indole (0.61 mmol) in MeOH (5 mL) was added silica gel (1 g) followed by N-chlorosuccinimide (94 mg, 0.7 mmol) at 0° C. The reaction was stirred for 1 h at 0° C. and was filtered. The filtrate was evaporated and the residue was purified by chromatography ($SiO_2$, 25% ethyl acetate-methylene chloride) to give 3-chloro-2-(2-(5-diehylphosphono)furanyl)indole.

Step E. To a solution of 3-chloro-2-(2-(5-diehylphosphono)furanyl)indole (0.28 mmol) in 5 mL of dry methylene chloride was added (2.8 mmol) bromotrimethyl silane at 0° C. The reaction mixture was allowed to stir at room temperature overnight. The solvent and excess bromotrimethylsilane were removed under reduced pressure and 5 mL of a 1/1 mixture of acetone/water was added and stirred for 12 h at room temperature. The resulting yellow solid was collected through filtration to give 3-chloro-2-(2-(5-phosphono)furanyl)indole (8.1, 50 mg). mp >220° C.; Anal. cald. for $C_{12}H_9NPO_4Cl+2H_2O+0.35HBr$: C: 39.82; H: 3.72; N: 3.87. Found: C: 39.96; H: 3.42; N: 3.60.

Example 9

Preparation of $N^1$-substituted-4-amino-(2-(5-phosphono)furanyl)indoles

Step A. A solution of 2-methyl-3-nitroaniline (1 mmol) in anhydrous diethyl ether was treated with 2-furoyl chloride (1.1 mmol) and pyridine (3.0 mmol) at 25° C. for 12 h. Extraction and chromatography afforded N-(2-furoyl)-2-methyl-3-nitroaniline as a white solid. TLC: Rf =0.41, 50% EtOAc-hexane.

Step B. The N-(2-furoyl)-2-methyl-3-nitroaniline (1 mmol) in DMSO was treated with potassium hydroxide (2.0 mmol) and 1-bromo-2-methylpropane (1.1 mmol) at 25° C. for 12 hr. Extraction and chromatography afforded N-(2-furoyl)-N-isobutyl-2-methyl-3-nitroaniline as a yellow syrup. TLC: Rf=0.40, 30% EtOAc-hexane.

Step C. The N-(2-furoyl)-N-isobutyl-2-methyl-3-nitroaniline (1 mmol) in THF was treated with lithium diisopropylamide (2.5 mmol) at −78° C. for 1 h. Then diethyl chlorophosphate (2.5 mmol) was added to the reaction. After 1 h. the reaction was quenched with saturated ammonium chloride. Extraction and chromatography gave N-(2-(5-diethylphosphono)furoyl)-N-isobutyl-2-methyl-3-nitroaniline as a reddish oil. TLC: Rf=0.15, 50% EtOAc-hexane.

Step D. A solution of N-(2-(5-diethylphosphono)furoyl)-N-isobutyl-2-methyl-3-nitroaniline (1 mmol) in DMF was treated with diethyl oxalate (1.5 mmol) and potassium ethoxide (1.5 mmol) at 120° C. for 1 hr. Extraction and chromatography afforded $N^1$-isobutyl-4-nitro-2-(2-(5-diethylphosphono)-furanyl)indole as a yellow solid. TLC: Rf=0.18, 50% EtOAc-hexane.

Step E. The $N^1$-isobutyl-4-nitro-2-(2-(5-diethylphosphono)furanyl)indole (1 mmol) in methanol was treated with palladium on carbon (10%) at 25° C. under 1 atomsphere of hydrogen for 1 h. The reaction mixture was filtered and the filtrate was evaporated under vacuum. The residue was purified through chromatography to give $N^1$-isobutyl-4-amino-2-(2-(5-diethylphosphono)furanyl)- indole as a dark brown oil. TLC: Rf=0.19, 50% EtOAc-hexane, double elution.

Step F. $N^1$-isobutyl-4-amino-2-(2-(5-diethylphosphono) furanyl)indole (1 mmol) in acetonitrile was treated with bromotrimethylsilane (10 mmol). After 12 h, the reaction was evaporated under vacuum and the residue was treated with a mixture of water and acetone. The solid was collected through filtration to give $N^1$-isobutyl-4-amino-2-(2-(5-phosphone)furanyl)indole as a white solid (9.1). mp 201–203° C.; Anal. cald. for $C_{16}H_{19}N_2O_4P+0.13CH_2Cl_2$: C: 56.10; H: 5.62; N: 8.11. Found: C: 56.47; H: 5.73; N: 7.73.

Example 10

Preparation of 5-chloro-3-isobutyl-2-(2-(5-phosphono)furanyl)indole

Step A. A mixture of 4-chlorophenylhydrazine hydrochloride (1.5 mmol), diethyl 2-(5-(4-methylvaleryl)) furanphosphonate (1 mmol, prepared as in Example 27), and two drops of concentrated sulfuric acid in glacial acetic acid was heated at reflux for 4 h. The cooled reaction mixture was evaporated to dryness, and the residue was subjected to extraction and chromatography to give 5-chloro-3-isobutyl-2-(2-(5-diethylphosphono)furanyl)indole as a yellow sticky solid. TLC: Rf=0.30, 50% EtOAc-hexane.

Step B. 5-Chloro-3-isobutyl-2-(2-(5-diethylphosphono) furanyl)indole was subjected to Step C of Example 1 to give 5-chloro-3-isobutyl-2-(2-(5-phosphono)furanyl)indole (10.1) as a dark green solid. mp 135–139° C.; Anal. cald. for $C_{16}H_{17}NO_4PCl+0.75H_2O$: C: 52.33; H: 5.08; N: 3.83. Found: C: 51.96; H: 4.93; N: 3.81.

Example 11

Preparation of 2-phosphonomethoxymethyl-9-azaindoles

Step A. A solution of 2-aminopyridine (1 mmol) and chloroacetone (1.25 mmol) in n-butanol was heated at reflux for 16 h. The cooled reaction mixture was evaporated to dryness, and the residue was subjected to extraction and chromatography to give 9-aza-2-methylindole as a light red oil. TLC: Rf=0.2, 65% EtOAc-hexane.

Step B. A mixture of 9-aza-2-methylindole and NBS (2.5 mmol) in carbontetrachloride was heated at reflux while being irradiated by a 250 W lamp. After 1 h the cooled reaction mixture was evaporated to dryness, and the residue was subjected to extraction and chromatography to give 9-aza-3-bromo-2-bromomethylindole as a off white solid. TLC: Rf=0.5, 50% EtOAc-hexane.

Step C. A solution of diethyl hydroxymethylphosphonate (1.7 mmol) in DMF was treated with sodium hydride (2 mmol) at 0° C. for 10 min. A solution of 9-aza-3-bromo-2-bromomethylindole (1 mmol) in DMF was added to the reaction mixture, and the resulting mixture was stirred at 25° C. for 16 h. Extraction and chromatography gave 9-aza-3-bromo-2-diethylphosphono-methoxymethylindole (TLC: Rf=0.3, 10% MeOH-EtOAc), and 9-aza-2-diethylphosphonomethoxymethylindole (TLC: Rf=0.2, 10% MeOH-EtOAc).

Step D. 9-Aza-3-bromo-2-diethylphosphonomethoxymethylindole and 9-aza-2-diethylphosphonomethoxymethylindole were subjected to Step C of Example 1 to give 9-aza-3-bromo-2-phosphonomethoxymethylindole (11.1, a brown hygroscopic solid. Anal. cald. for $C_9H_{10}N_2O_4PBr+1.75H_2O+0.5 HBr$: C: 27.50; H: 3.59; N: 7.13. Found: C: 27.64; H: 3.22;

N: 6.81), and 9-aza-2-phosphonomethoxymethylindole (11.2, a yellow hygroscopic solid. Anal. calcd. for $C_9H_{11}N_2O_4PBr+0.5H_2O+0.65HBr$: C: 35.59; H: 4.20; N: 9.22. Found: C: 35.46; H: 3.97; N: 8.95).

Step E. A solution of 9-aza-3-bromo-2-diethylphosphonomethoxymethyl-indole (1 mmol), tetrakis (triphenylphosphine) palladium (0.2 mmol), phenylboronic acid (6 mmol), and sodium bicarbonate (5 mmol) was stirred at 85° C. for 3 h. Extraction and chromatography gave 9-aza-3-phenyl-2-diethylphosphonomethoxymethylindole. TLC: Rf =0.5, 33% EtOAc-hexane.

Step F. 9-aza-3-phenyl-2-diethylphosphonomethoxymethylindole was subjected to Step C of Example 1 to give 9-aza-3-phenyl-2-phosphono-methoxymethylindole (11.3) as a yellow solid. mp >250° C.; Anal. calcd. for $C_{15}H_{15}N_2O_4P+0.5H_2O+0.75HBr$: C: 46.44; H: 4.35; N: 7.22. Found: C: 46.05; H: 4.41; N: 7.34.

Step G. A solution of 9-aza-3-bromo-2-diethylphosphonomethoxymethyl-indole (1 mmol) and 10% palladium on carbon (10% wt/wt) in methanol was stirred at 25° C. for 1 h. Filtration, evaporation and chromatography gave 9-aza-5,6,7,8-tetrahydro-2-diethylphosphonomethoxymethylindole as a yellow oil.

Step H. 9-aza-5,6,7,8-tetrahydro-2-diethylphosphonomethoxymethyl-indole was subjected to Step C of Example 1 to give 9-aza-5,6,7,8-tetrahydro-2-phosphonomethoxymethylindole (11.4) as a light sticky solid. Anal. calcd. for $C_9H_{15}N_2O_4P+1.16HBr$: C: 31.79; H: 4.79; N: 8.24. Found: C: 31.95; H: 4.66; N: 7.85.

Step I. 7-Nitro-9-aza-2-methylindole, prepared from 2-Amino-3-nitropyridine and chloroacetone according to Step A of example 12, was subjected to Step B, C, and E of example 11, Step C of example 13, and Step C of example 1 to give 7-amino-9aza-3-phenyl-2-phosphonomethoxymethyl-indole (11.5). mp >250° C.; Anal. calcd. for $C_{15}H_{16}N_3O_4P+1MeOH+0.1HBr$: C: 51.46; H: 5.43; N: 11.25. Found: C: 51.42; H: 5.04; N: 11.06.

Example 12

Preparation of 9-aza-2-(phosphonomethylaminocarbonyl)indoles

Step A. A solution of 2-aminopyridine (1 mmol) and bromopyruvate (1.2 mmol) in n-butanol was heated at reflux for 16 h. The cooled reaction mixture was evaporated to dryness, and the residue was subjected to extraction and chromatography to give ethyl 9-aza-2-indolecarboxylate as a light yellow solid. TLC: Rf=0.30, 100% EtOAc.

Step B. A solution of ethyl 9-aza-2-indolecarboxylate (1 mmol) in $THF:EtOH:H_2O$ (3:2:1) was treated with sodium hydroxide (1.2 mmol) at 25° C. for 1 h. The reaction mixture was evaporated to dryness and the residue was dissolved in DMF and treated with EDCI (1.3 mmol), HOBt (1.5 mmol), and diethyl aminomethylphosphonate (1.5 mmol) at 25° C. for 24 h. Extraction and chromatography gave 9-aza-2-(diethylphosphonomethylaminocarbonyl)indole as a clear film.

Step C. 9-aza-2-(diethylphosphonomethylaminocarbonyl)indole was subjected to Step C of Example 1 to give 9-aza-2-phosphonomethylaminocarbonylindole (12.1) as a white solid. mp >250° C. Anal. calcd. for $C_9H_{10}N_3O_4P+1H_2O$: C: 39.57; H: 4.43; N: 15.38. Found: C: 39.13; H: 4.03; N: 15.17.

Step D. 9-aza-2-(diethylphosphonomethylaminocarbonyl)indole was subjected to Step G of Example 11 to give 9-aza-5,6,7,8-tetrahydro-2-diethylphosphonomethylaminocarbonylindole (as an oil) which was subjected to Step C of Example 1 to give 9-aza-5,6,7,8-tetrahydro-2-phosphonomethylaminocarbonylindole (12.2) as a hygroscopic solid. Anal. calcd. for $C_9H_{14}N_3O_4P+0.3H_2O+1.1HBr$: C: 30.57; H: 4.48; N: 11.88. Found: C: 30.96; H: 4.77; N: 11.46.

Example 13

Preparation of 7-amino-9-aza-2-phosphonomethylaminocarbonylindole

Step A. 2-Amino-3-nitropyridine was subjected to Step A of example 12 to give ethyl 7-nitro-9-aza-2-indolecarboxylate as a yellow solid. mp 198–199° C. Anal. calcd. for $C_{10}H_9N_3O_4$: C: 51.07; H: 3.86; N: 17.87. Found: C: 51.25; H: 3.93; N: 17.94.

Step B. 7-Nitro-9-aza-2-indolecarboxylate was subjected to Steps B of Example 12 to give 7-nitro-9-aza-2-diethylphosphonomethylaminocarbonyl-indole as a yellow sticky solid.

Step C. A solution of 7-nitro-9-aza-2-diethylphosphonomethylaminocarbonylindole (1 mmol) and 10% palladium on carbon (10% wt/wt) in methanol was stirred at 0° C. under 1 atmosphere of hydrogen for 10 min. Filtration, evaporation and chromatography gave 7-amino-9-aza-2-diethylphosphonomethylaminocarbonylindole as a sticky solid.

Step D. 7-Amino-9-aza-2-diethylphosphonomethylaminocarbonylindole was subjected to Step C of Example 1 to give 7-amino-9-aza-2-phosphonomethylaminocarbonylindole (13.1) as a solid. mp >250° C. Anal. calcd. for $C_9H_{11}N_4O_4P+0.5$ MeOH+ 0.125HBr: C: 38.51; H: 4.46; N: 18.91. Found: C: 38.56; H: 4.13; N: 18.60.

Example 14

Preparation of 9-aza-2-(2-(5-phosphono)furanyl) indoles

Step A. 2-Bromoacetylfuran (1.3 mmol) and 2-aminopyridine (1 mmol) was subjected to Step A of Example 12 to give 9-aza-2-(2-furanyl)indole as a brown solid.

Step B. A solution of 9-aza-2-(2-furanyl)indole (1 mmol) and N,N,N',N'-tetramethylethylenediamine (1.1 mmol) in THF was treated with nBuLi (1.1 mmol) at −78° C. for 1 h. Diethyl chlorophosphate (2 mmol) was added to the reaction mixture and the resulting mixture was stirred at −78° C. for another 2 h. Extraction and chromatography gave 9-aza-2-(2-(5-diethylphosphono)furanyl)-indole as a brown solid.

Alternatively 9-aza-2-(2-(5-diethylphosphono)furanyl) indoles can also be prepared from 2-aminopyridines and diethyl 5-bromoacetyl-2-furanphosphonate following procedures of Step A of Example 1.

Step C. 9-aza-2-(2-(5-diethylphosphono)furanyl)indole was subjected to Step C of Example 1 to give 9-aza-2-(2-(5-phosphono)furanyl)indole as a gray solid (14.1). mp >250° C. Anal. calcd. for $C_{11}H_9N_2O_4P+0.5H_2O$: C: 48.36; H: 3.69; N: 10.25. Found: C: 48.34; H: 3.55; N: 9.99.

The following compounds were prepared according to the above described procedures:

14.2: 9-Aza-5-chloro-2-(2-(5-phosphono)furanyl)indole. mp 215–217° C. Anal. calcd. for $C_{11}H_8N_2O_4PCl+1.25 H_2O$: C: 41.14; H: 3.30; N: 8.72. Found: C: 41.47; H: 3.40; N: 8.38.

14.3: 9-Aza-5-trifluoromethyl-7-chloro-2-(2-(5-phosphono) furanyl)indole. mp 185–190° C. Anal. cald. for $C_{12}H_7N_2O_4PF_3Cl+0.7H_2O+0.1CH_2Cl_2$: C: 37.48; H: 2.24; N: 7.23. Found: C: 37.62; H: 2.61; N: 7.02.

14.4: 9-Aza-3-isobutyl-7-methyl-2-(2-(5-phosphono) furanyl)indole was also prepared in this manner starting from 2-amino-3-methylpyridine and diethyl 2-(5-(2-bromo-4-methyl-1-oxo-1-pentyl)furanphosphonate (prepared in Example 28). mp 225–227° C. Anal. cald. for $C_{16}H_{19}N_2O_4P+1HBr$: C: 46.28; H: 4.85; N: 6.75. Found: C: 46.23; H: 4.89; N: 6.57.

Example 15

Preparation of 2-(2-(5-diphenylphosphono)furanyl) indoles

A suspension of 2-(2-furanyl)indole (1 mmol) in THF at −78° C. is treated with LDA (2.3 mmol) for 1 h. A solution of diphenyl chlorophosphate in THF is added and the reaction is stirred at −78° C. for another hour. The reaction is warmed to 0° C. and quenched with aqueous saturated sodium bicarbonate. Extraction and chromatography gives 2-(2-(5-diphenylphosphono)furanyl)indoles.

Alternatively, 2-(2-(5-diphenylphosphono)furanyl) indoles are also prepared from 2-(2-(5-phosphono)furanyl) indole and phenol as described in Example 18.

Example 16

Preparation of Acyloxymethylphosphonate Diesters

A solution of 2-(2-(5-phosphono)furanyl)indole (1 mmol) in acetonitrile and N,N,N-diisopropylethylamine (5 mmol) is treated with acyloxymethyl iodide (4 mmol) at 0° C. for 24 h. Extraction and chromatography gives 2-(2-(5-diacyloxymethylphosphono)furanyl)indole.

2-(2-(5-bis(3-phthalidyl)phosphono)furanyl)indole is also synthesized following this procedure using 3-bromophthalide as the alkylating reagent.

Example 17

Preparation of Hydroxyethyldisulfidylethylphosphonate Diester

A suspension of 2-(2-(5-phosphono)furanyl)indole (1 mmol) in thionyl chloride (5 mL) is refluxed for 4 h. The cooled reaction mixture is evaporated to dryness and the resulting yellow residue is added to a solution of 2-hydroxyethyl disulfide (4 mmol) and pyridine (2.5 mmol) in methylene chloride. After stirring at 25° C. for 4 h. the reaction is subjected to extraction and chromatography to give 2-(2-(5-bis(6'-hydroxy-3',4'-disulfide)hexylphosphono) furanyl)indole and 2-(2-(5-(3',4'-disulfidehexane-1,6-yl) phosphono)furanyl)indole.

Example 18

Preparation of Benzyl Phosphonate Diesters

A suspension of 2-(2-(5-phosphono)furanyl)indole (1 mmol) in thionyl chloride (5 mL) is refluxed for 4 h. The cooled reaction mixture is evaporated to dryness and the resulting yellow residue is added to a solution of the corresponding benzyl alcohol (4 mmol), and pyridine (2.5 mmol) in methylene chloride. After stirring at 25° C. for 4 h the reaction is extracted and chromatographed to give 2-(2-(5-dibenzylphosphono)furanyl)indoles.

2-(2-(5-bis(3-phthalidylethyl)phosphono)furanyl)indoles are also prepared according to the above described procedures using 2-(3-phthalidyl)ethanol which was prepared in Example 24).

Example 19

Preparation of (5-substituted 2-oxo-1 3-dioxolen-4-yl)methyl Phosphonate Diesters A solution of 2-(2-(5-phosphono)furanyl)indole (1 mmol) in DMF and sodium hydride (4 mmol) is treated with 5-methyl-4-bromomethyl-2-oxo-1,3-dioxolene (4 mmol, prepared according to *Chem. Pharm. Bull.* 1984, 32(6), 2241) at 25° C. for 24 h. Extraction and chromatography gives 2-(2-(5-bis(5-methyl-2-oxo-1,3-dioxolen-4-yl)methyl phosphono)furanyl)indole.

Alternatively, 2-(2-(5-bis(5-methyl-2-oxo-1,3-dioxolen-4-yl)methyl phosphono)furanyl)indole is prepared from 2-(2-(5-phosphono)furanyl)indole and 5-methyl-4-hydroxymethyl-2-oxo-1,3-dioxolene (prepared from 4,5-dimethyl-2-oxo-1,3-dioxolene as described in Example 26) as described in Example 18.

Example 20

Preparation of Alkyloxycarbonyloxyalkyl Phosphonate Esters

A solution of 2-(2-(5-phosphono)furanyl)indole (1 mmol) in 5 mL of anhydrous DMF is treated with N,N'-dicyclohexyl-4-morpholinecarboxamidine (5 mmol), and isopropyloxycarbonyloxymethyl iodide (5 mmol) which is prepared from the commercially available chloromethyl chloroformate according to the reported procedure, Nishimura, et al. *J. Antibiotics,* 1987, 40(1), 81–90. The reaction mixture is stirred for 24 h at room temperature and the solvent is removed under reduced pressure. The resulting syrup is chromatographed on to yield 2-(2-(5-diialkyloxycarbonyloxymethylphosphono)furanyl)adenine.

Other alkyloxycarbonyloxymethyl, aryloxycarbonyloxymethyl, alkyl- and arylthiocarbonyloxymethyl phosphonate esters can also be prepared following the above described procedures.

Example 21

Preparation of 1-substituted-1,3-propanediol cyclic esters of purine phosphonates Step A (*J. Org. Chem.* 1957, 22, 589) To a solution of 2-pyridine propanol (72.9 mmol) in acetic acid (75 mL) was added 30% hydrogen peroxide slowly. The reaction mixture was heated to 80° C. for 16 h. The reaction was concentrated under vacuum and the residue was dissolved in acetic anhydride (100 mL) and heated at 110° C. overnight. Acetic anhydride was evaporated upon completion of reaction. Chromatography of the mixture by eluting with methanol-methylene chloride (1:9) resulted in 10.5 g of pure 2-(1-(1, 3-diacetoxy)propyl)pyridine.

Step B. To a solution of 2-(1-(1,3-diacetoxy)propyl) pyridine (21.1 mmol) in methanol-water (3:1, 40 mL) was added potassium carbonate (105.5 mmol). After stirring for 3 h at room temperature, the reaction mixture was concentrated. The residue was chromatographed by eluting with methanol-methylene chloride (1:9) to give 2-(1-(1,3-dihydroxy)propyl)pyridine as a solid.

Step C. A suspension of 2-(2-(5-phosphono)furanyl) indole (1 mmol) in 5 mL of thionyl chloride is heated at reflux temperature for 4 h. The reaction mixture is cooled and evaporated to dryness. To the resulting residue is added a solution of 2-(1-(1,3-dihydroxy)propyl)pyridine (1 mmol) and pyridine (2.5 mmol) in 3 mL of methylene chloride. After stirring at 25° C. for 4 h the reaction is subjected to work up and chromatography to give 2-(2-(5-(1-(2-pyridyl)propan-1,3-yl)phosphono)furanyl)indole.

Following the above described procedures, other cyclic esters are also prepared, such as 2-(2-(5-(1-(4-pyridyl)propan-1,3-yl)phosphono)furanyl)indole, 2-(2-(5-(1-(3-pyridyl)propan-1,3-yl)phosphono)furanyl)indole, and 2-(2-(5-(1-phenylpropan-1,3-yl)phosphono)furanyl)indole.

Example 22

Preparation of 2-substituted-1,3-propanediol cyclic esters of indole phosphonates Step A. To a solution of 2-(hydroxymethyl)-1,3-propanediol (1 g, 9.4 mmol) in pyridine (7.5 mL) at 0° C. was added acetic anhydride (0.89 mL, 9.4 mmol) slowly. The resulting solution was warmed to room temperature and stirred for 16 h. The reaction was concentrated under reduced pressure and chromatographed by eluting with methanol-dichloromethane (1:9) to give 510 mg of pure 2-acetoxymethyl-1,3-propanediol.

Step B. 2-Acetoxymethyl-1,3-propanediol was coupled to 2-(2-(5-phosphono)furanyl)indole following Step C of Example 21 to give 2-(2-(5-(2-(acetoxymethyl)propan-1,3-yl)phosphono)furanyl)indole.

Following the above described procedures, other cyclic esters are also prepared, such as 2-(2-(5-(2-(methoxycarbonyloxymethyl)-propan-1,3-yl)phosphono)furanyl)indole, 2-(2-(5-(2-(hydroxymethyl)-propan-1,3-yl)phosphono)furanyl)indole, 2-(2-(5-(2,2-dihydroxymethylpropan-1,3-yl)phosphono)furanyl)indole. 2-(2-(5-(2-(methoxycarbonyloxymethyl)propan-1,3-yl)phosphono)furanyl)indole is prepared by coupling of 2-(2-(5-phosphono)-furanyl)indole with 2-(methoxycarbonyloxymethyl)-1,3-propanediol which was prepared as follows:

To a solution of 2-(hydroxymethyl)-1,3-propanediol (1 g, 9.4 mmol) in dichloromethane (20 mL) and pyridine (7.5 mL) at 0° C. was added methyl chloroformate (0.79 mL, 9.4 mmol) slowly. The resulting solution was warmed to room temperature and stirred for 16 h. The reaction was concentrated under reduced pressure and chromatographed by eluting with methanol-dichloromethane (1:4) to give 650 mg of pure carbonate.

Example 23

Preparation of 2-(2-(5-(5-hydroxyl-1,3-cyclohexyl)phosphono)furanyl)indoles

A suspension of 2-(2-(5-phosphono)furanyl)indole (1 mmol) in 5 mL of thionyl chloride is heated at reflux temperature for 4 h. The reaction mixture is cooled and evaporated to dryness. To the resulting residue is added a solution of cis,cis-1,3,5-cyclohexanetriol (1 mmol) and pyridine (2.5 mmol) in 3 mL of methylene chloride. After stirring at 25° C. for 24 h the reaction is subjected to work up and chromatography to give 2-(2-(5-(5-hydroxyl-1,3-cyclohexyl)-phosphono)furanyl)indole.

Example 24

Preparation of 3-(2-hydroxyethyl)phthalide

A solution of phthalide-3-acetic acid (1 mmol) in THF was treated with borane dimethylsulfide (1.5 mmol) at 0° C. for 1 h, and 25° C. for 24 h. Extraction and chromatography gave 2-(3-phthalidyl)ethanol as a light yellow oil. TLC: Rf=0.25, 50 % EtOAc-hexane.

Example 25

Preparation of Indole Phosphonate Amine Salts

A mixture of 2-(2-(5-phosphono)furanyl)indole (1 mmol) and tris(hydroxymethyl)-aminomethane (1.05 mmol) in methanol is stirred at 25° C. for 24 h. Evaporation give 2-(2-(5-phosphono)furanyl)indole tris(hydroxymethyl) aminomethane salt.

Example 26

Preparation of 5-methyl-4-hydroxymethyl-2-oxo-1,3-dioxolene

A mixture of 4,5-dimethyl-2-oxo-1,3-dioxolene (1 mmol) and selenium dioxide (2.5 mmol) in dioxane was heated at reflux for 1 h. Evaporation, extraction and chromatography gave 5-methyl-4-hydroxymethyl-2-oxo-1,3-dioxolene as a yellow oil. TLC: Rf=0.5, 5% MeOH-dichloromethane.

Example 27

Preparation of diethyl 2-(5-(4-methylvaleryl)) furanphosphonate

Step A. A solution of 2-tributylstannylfuran (1 mmol), 4-methylvaleroyl chloride (1.1 mmol), and $PdCl_2(PPh_3)_2$ (0.05 mmol) in THF was stirred at 25° C. for 24 h. Extraction and chromatography gave 2-(4-methylvaleryl)furan.

Step B. A solution of 2-(4-methylvaleryl)furan (1 mmol) and N,N-dimethylhydrazine (1.5 mmol) in EtOH was heated at reflux for 24 h. Evaporation and distilation gave 2-(4-methylvaleryl)furan dimethylhydrazone as a brown oil.

Step C. A solution of 2-(4-methylvaleryl)furan dimethylhydrazone (1 mmol) in THF was cooled to −78° C. and treated with LDA (1.2 mmol) dropwise. After 1 h, diethyl chlorophosphate (1.2 mmol) was added, and the resulting mixture was stirred at −78° C for 1 h. The reaction was quenched with brine, and subjected to extraction and chromatography to give diethyl 2-(5-(4-methylvaleryl))furanphosphonate dimethylhydrazone.

Step D. A solution of diethyl 2-(5-(4-methylvaleryl))furanphosphonate dimethylhydrazone (1 mmol) in THF-pH=7 phosphate buffer (1:1) was treated with $CuCl_2$ (1.5 mmol) at 25° C. for 24 h. Extraction and chromatography gave diethyl 2-(5-(4-methylvaleryl))furanphosphonate as a brown oil.

Example 28

Preparation of 2-(5-(2-bromo-4-methylvaleryl))furanphosphonate

Step A. A mixture of diethyl 2-(5-(4-methylvaleryl))furanphosphonate (1 mmol, prepared as described in Example 27) and $CuBr_2$ (4 mmol) in $EtOAc-CHCl_3$ was stirred at 25° C. for 24 h. The reaction was quenched with satured ammonium chloride. Extraction and chromatography gave 2-(5-(2-bromo-4-methylvaleryl))furanphosphonate as a yellow oil.

Examples of use of the method of the invention includes the following. It will be understood that these examples are exemplary and that the method of the invention is not limited solely to these examples.

For the purposes of clarity and brevity, chemical compounds are referred to as synthetic example numbers in the biological examples below.

Besides the following Examples, assays that may be useful for identifying compounds which inhibit gluconeogenesis include the following animal models of Diabetes:

i. Animals with pancreatic b-cells destroyed by specific chemical cytotoxins such as Alloxan or Streptozotocin (e.g. the Streptozotocin-treated mouse, -rat, dog, and -monkey). Kodama, H., Fujita, M., Yamaguchi, I., *Japanese Journal of Pharmacology* 1994, 66, 331–336 (mouse); Youn, J. H., Kim, J. K., Buchanan, T. A., *Diabetes* 1994, 43, 564–571 (rat); Le Marchand, Y., Loten, E. G., Assimacopoulos-Jannet, F., et al., *Diabetes* 1978, 27, 1182–88 (dog); and Pitkin, R. M., Reynolds, W. A., *Diabetes* 1970, 19, 70–85 (monkey).

ii. Mutant mice such as the C57BL/Ks db/db, C57BL/Ks ob/ob, and C57BU6J ob/ob strains from Jackson Laboratory, Bar Harbor, and others such as Yellow Obese, T-KK, and New Zealand Obese. Coleman, D. L., Hummel, K. P., *Diabetologia* 1967, 3, 238–248 (C57BL/Ks db/db); Coleman, D. L., *Diabetologia* 1978, 14, 141–148 (C57BL/6J ob/ob); Wolff, G. L., Pitot, H. C., *Genetics* 1973, 73, 109–123 (Yellow Obese); Dulin, W. E., Wyse, B. M., *Diabetologia* 1970, 6, 317–323 (T-KK); and Bielschowsky, M., Bielschowsky, F. *Proceedings of the University of Otago Medical School,* 1953, 31, 29–31 (New Zealand Obese).

iii. Mutant rats such as the Zucker fa/fa Rat rendered diabetic with Streptozotocin or Dexamethasone, the Zucker Diabetic Fatty Rat, and the Wistar Kyoto Fatty Rat. Stolz, K. J., Martin, R. J. *Journal of Nutrition* 1982, 112, 997–1002 (Streptozotocin); Ogawa, A., Johnson, J. H., Ohnbeda, M., McAllister, C. T., Inman, L., Alam, T., Unger, R. H., *The Journal of Clinical Investigation* 1992, 90, 497–504 (Dexamethasane); Clark, J. B., Palmer, C. J., Shaw, W. N., *Proceedings of the Society for Experimental Biology and Medicine* 1983, 173, 68–75 (Zucker Diabetic Fatty Rat); and Idida, H., Shino, A., Matsuo, T., et al., *Diabetes* 1981, 30, 1045–1050 (Wistar Kyoto Fatty Rat).

iv. Animals with spontaneous diabetes such as the Chinese Hamster, the Guinea Pig, the New Zealand White Rabbit, and non-human primates such as the Rhesus monkey and Squirrel monkey. Gerritsen, G. C., Connel, M. A., Blanks, M. C., *Proceedings of the Nutrition Society* 1981, 40, 237 245 (Chinese Hamster); Lang, C. M., Munger, B. L., *Diabetes* 1976, 25, 434–443 (Guinea Pig); Conaway, H. H., Brown, C. J., Sanders, L. L. eta I., *Journal of Heredity* 1980, 71, 179–186 (New Zealand White Rabbit); Hansen, B. C., Bodkin, M. L., *Diabetologia* 1986, 29, 713–719 (Rhesus monkey); and Davidson, I. W., Lang, C. M., Blackwell, W. L., *Diabetes* 1967, 16, 395–401 (Squirrel monkey).

v. Animals with nutritionally induced diabetes such as the Sand Rat, the Spiny Mouse, the Mongolian Gerbil, and the Cohen Sucrose-Induced Diabetic Rat. Schmidt-Nielsen, K., Hainess, H. B., Hackel, D. B., *Science* 1964, 143, 689–690 (Sand Rat); Gonet, A. E., Stauffacher, W., Pictet, R., et al., *Diabetologia* 1965,1, 162–171 (Spiny Mouse); Boquist, L., *Diabetologia* 1972, 8, 274–282 (Mongolian Gerbil); and Cohen, A. M., Teitebaum, A., Saliternik, R., *Metabolism* 1972, 21, 235–240 (Cohen Sucrose-Induced Diabetic Rat).

vi. Any other animal with one of the following or a combination of the following characteristics resulting from a genetic predisposition, genetic engineering, selective breeding, or chemical or nutritional induction: impaired glucose tolerance, insulin resistance, hyperglycemia, obesity, accelerated gluconeogenesis, increased hepatic glucose output.

Example A

Inhibition of Human Liver FBPase

*E. coli* strain BL21 transformed with a human liver FBPase-encoding plasmid was obtained from Dr. M. R. El-Maghrabi at the State University of New York at Stony Brook. hlFBPase was typically purified from 10 liters of *E. coli* culture as described (M. Gidh-Jain et al., *The Journal of Biological Chemistry* 1994, 269, 27732–27738). Enzymatic activity was measured spectrophotometrically in reactions that coupled the formation of product (fructose 6-phosphate) to the reduction of dimethylthiazoldiphenyltetrazolium bromide (MTT) via NADP and phenazine methosulfate (PMS), using phosphoglucose isomerase and glucose 6-phosphate dehydrogenase as the coupling enzymes. Reaction mixtures (200 µL) were made up in 96-well microtitre plates, and consisted of 50 mM Tris-HCl, pH 7.4,100 mM KCl, 5 mM EGTA, 2 mM MgCl$_2$, 0.2 mM NADP, 1 mg/mL BSA, 1 mM MTT, 0.6 mM PMS, 1 unit/mL phosphoglucose isomerase, 2 units/mL glucose 6-phosphate dehydrogenase, and 0.150 mM substrate (fructose 1,6-bisphosphate). Inhibitor concentrations were varied from 0.01 µM to 10 µM. Reactions were started by the addition of 0.002 units of pure hlFBPase and were monitored for 7 minutes at 590 nm in a Molecular Devices Plate Reader (37° C.).

Figure 2:
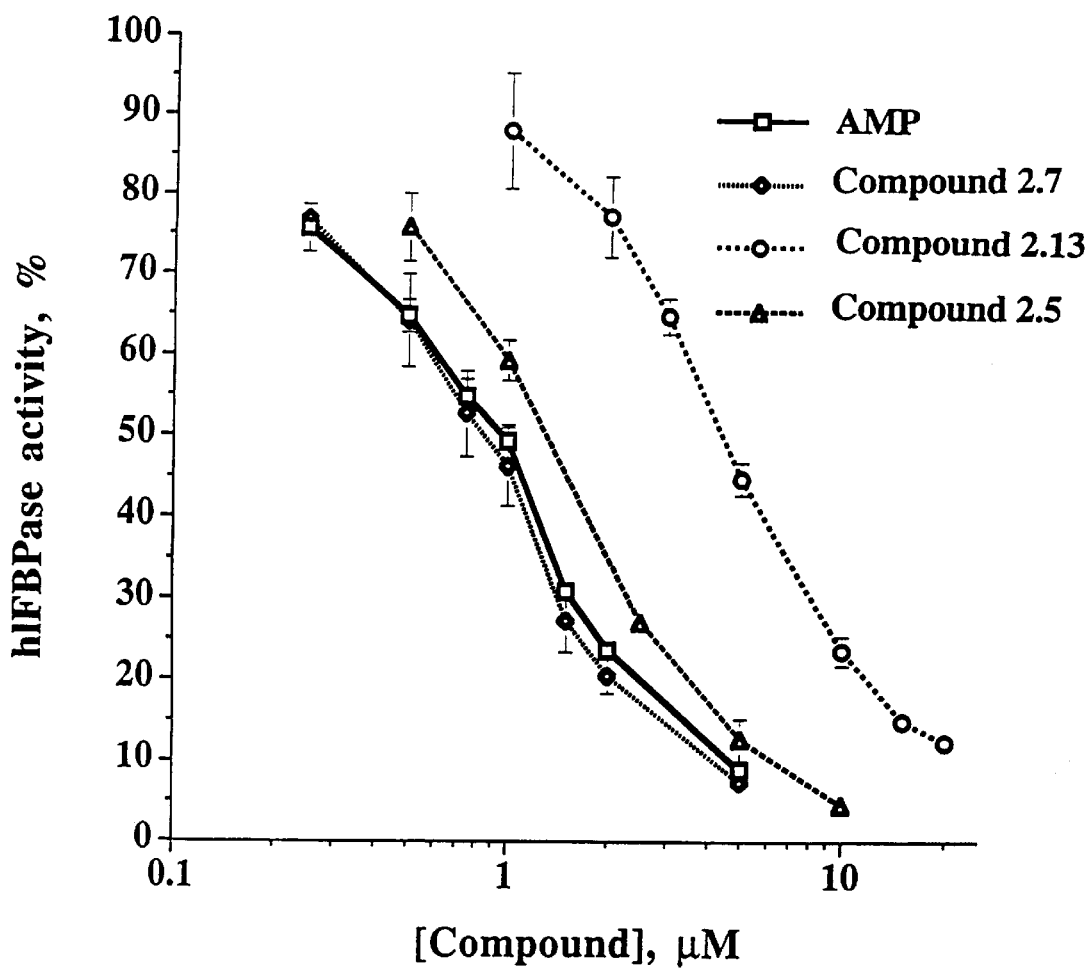
FIG. 2 depicts the dose dependent inhibition of hlFBPase by AMP and compounds 3.1, 2.1, and 1.1.

FIG. 2 shows the dose-dependent inhibition of hlFBPase by adenosine monophosphate (AMP), compounds 3.1, 2.1, and 1.1.

Table 2 provides IC$_{50}$ values of representative compounds according to the invention. The concentration of adenosine monophosphate (AMP) required to inhibit half of the hlFBPase activity under the above reaction conditions was 1.0 µM.

TABLE 2

| Example Compound Number | HL FBPase IC$_{50}$ (µM) | Mouse FBPase IC$_{50}$ (µM) | Rat Liver FBPase IC$_{50}$ (µM) |
| --- | --- | --- | --- |
| 3.1 | 30.0 | — | — |
| 1.1 | 10.0 | — | — |
| 5.1 | 8.8 | >20 | >20 |
| 1.3 | 60.6 | — | — |
| 9.1 | 32.5 | — | — |
| 6.1 | 10.7 | >20 | >20 |
| 7.1 | 8.67 | >20 | >20 |
| 7.2 | 8.5 | >20 | >20 |
| 10.1 | 2.5 | — | — |
| 11.3 | 10 | — | — |
| 12.1 | 90 | — | — |
| 14.4 | 1.6 | >30 | >25 |
| 11.5 | 10 | — | 90 |
| 14.2 | 4.5 | — | — |

Inhibitors of FBPase may also be identified by assaying rat and mouse liver FBPase.

In vitro Inhibition of Rat Liver and Mouse Liver FBPase.

*E. coli* strain BL21 transformed with a rat liver FBPase-encoding plasmid is obtained from Dr. M. R. El-Maghrabi at the State University of New York at Stony Brook, and purified as described (El-Maghrabi, M. R., and Pilkis, S. J. *Biochem. Biophys. Res. Commun.* 1991, 176, 137–144). Mouse liver FBPase is obtained by homogenizing freshly isolated mouse liver in 100 mM Tris-HCl buffer, pH 7.4, containing 1 mM EGTA, and 10% glycerol. The homogenate is clarified by centrifugation, and the 45–75% ammonium sulfate fraction prepared. This fraction is redissolved in the homogenization buffer and desalted on a PD-10 gel filtration column (Biorad) eluted with same. This partially purified fraction is used for enzyme assays. Both rat liver and mouse liver FBPase are assayed as described for human liver FBPase. Generally, as reflected by the higher $IC_{50}$ values, the rat and mouse liver enzymes are less sensitive to inhibition by the compounds tested than the human liver enzyme.

Example B

AMP Site Binding

To determine whether compounds bind to the allosteric AMP binding site of hlFBPase, the enzyme is incubated with radiolabeled AMP in the presence of a range of test compound concentrations. The reaction mixtures consist of 25 mM $^3$H-AMP (54 mCi/mmol) and 0–1000 mM test compound in 25 mM Tris-HCl, pH 7.4, 100 mM KCl and 1 mM $MgCl_2$. 1.45 mg of homogeneous FBPase (±1 nmole) is added last. After a 1 minute incubation, AMP bound to FBPase is separated from unbound AMP by means of a centrifugal ultrafiltration unit ("Ultrafree-MC", Millipore) used according to the instructions of the manufacturer. The radioactivity in aliquots (100 µL) of the upper compartment of the unit (the retentate, which contains enzyme and label) and the lower compartment (the filtrate, which contains unbound label) are quantified using a Beckman liquid scintillation counter. The amount of AMP bound to the enzyme is estimated by comparing the counts in the filtrate (the unbound label) to the total counts in the retentate.

Example C

AMP Site/Enzyme Selectivity

To determine the selectivity of compounds towards FBPase, effects of FBPase inhibitors on 5 key AMP binding enzymes were measured using the assays described below:
Adenosine Kinase: Human adenosine kinase was purified from an E. coli expression system as described by Spychala et al. (Spychala, J., Datta, N. S., Takabayashi, K., Datta, M., Fox, I. H., Gribbin, T., and Mitchell, B. S. Proc. Natl. Acad. Sci. USA 1996, 93, 1232–1237). Activity was measured essentially as described by Yamada et al. (Yamada, Y., Goto, H., Ogasawara, N. Biochim. Biophys. Acta 1988, 660, 36–43.) with a few minor modifications. Assay mixtures contained 50 mM TRIS-maleate buffer, pH 7.0, 0.1% BSA, 1 mM ATP 1 mM $MgCl_2$, 1.0 µM [U-$^{14}$C] adenosine (400–600 mCi/mmol) and varying duplicate concentrations of inhibitor. $^{14}$C-AMP was separated from unreacted $^{14}$C-adenosine by absorption to anion exchange paper (Whatman) and quantified by scintillation counting.
Adenosine Monophosphate Deaminase: Porcine heart AMPDA was purified essentially as described by Smiley et a. (Smiley, K. L., Jr, Berry, A. J., and Suelter, C. H. J. Biol. Chem. 1967, 242, 2502–2506) through the phosphocellulose step. Inhibition of AMPDA activity was determined at 37° C. in a 0.1 mL assay mixture containing inhibitor, ~0.005U AMPDA, 0.1% bovine serum albumin, 10 mM ATP, 250 mM KCl, and 50 mM MOPS at pH 6.5. The concentration of the substrate AMP was varied from 0.125–10.0 mM. Catalysis was initiated by the addition of enzyme to the otherwise complete reaction mixture, and terminated after 5 minutes by injection into an HPLC system. Activities were determined from the amount of IMP formed during 5 minutes. IMP was separated from AMP by HPLC using a Beckman Ultrasil-SAX anion exchange column (4.6 mm×25 cm) with an isocratic buffer system (12.5 mM potassium phosphate, 30 mM KCl, pH 3.5) and detected spectrophotometrically by absorbance at 254 nm.
Phosphofructokinase: Enzyme (rabbit liver) was purchased from Sigma. Activity was measured at 30° C. in reactions in which the formation of fructose 1,6-bisphosphate was coupled to the oxidation of NADH via the action of aldolase, triosephosphate isomerase, and α-glycerophosphate dehydrogenase. Reaction mixtures (200 µL) were made up in 96-well microtitre plates and were read at 340 nm in a Molecular Devices Microplate Reader. The mixtures consisted of 200 mM Tris-HCl pH 7.0, 2 mM DTT, 2 mM MgCl2, 0.2 mM NADH, 0.2 mM ATP, 0.5 mM Fructose 6-phosphate, 1 unit aldolase/mL, 3 units/mL triosephosphate isomerase, and 4 units/mL α-glycerophosphate dehydrogenase. Test compound concentrations ranged from 1 to 500 µM. Reactions were started by the addition of 0.0025 units of phosphofructokinase and were monitored for 15 minutes. Glycogen Phosphorylase: Enzyme (rabbit muscle) was purchased from Sigma. Activity was measured at 37° C. in reactions in which the formation of glucose 1-phosphate was coupled to the reduction of NADP via phosphoglucomutase and glucose 6-phosphate dehydrogenase. Assays were performed on 96-well microtitre plates and were read at 340 nm on a Molecular Devices Microplate Reader. Reaction mixtures consisted of 20 mM imidazole, pH 7.4, 20 mM $MgCl_2$, 150 mM potassium acetate, 5 mM potassium phosphate, 1 mM DTT, 1 mg/mL BSA, 0.1 mM NADP, 1 unit/mL phosphoglucomutase, 1 unit/mL glucose 6-phosphate dehydrogenase, 0.5% glycogen. Test compound concentrations ranged from 1 to 500 µM. Reactions were started by the addition of 17 µg enzyme and were monitored for 20 minutes. Adenylate Kinase: Enzyme (rabbit muscle) was purchased from Sigma. Activity was measured at 37° C. in reaction mixtures (100 µL) containing 100 mM Hepes, pH 7.4, 45 mM $MgCl_2$, 1 mM EGTA, 100 mM KCl, 2 mg/mL BSA, 1 mM AMP and 2 mM ATP. Reactions were started by addition of 4.4 ng enzyme and terminated after 5 minutes by addition of 17 µL perchloric acid. Precipitated protein was removed by centrifugation and the supernatant neutralized by addition of 33 µL 3 M KOH/3 M $KH_2CO_3$. The neutralized solution was clarified by centrifugation and filtration and analyzed for ADP content (enzyme activity) by HPLC using a YMC ODS AQ column (25×4.6 cm). A gradient was run from 0.1 M $KH_2PO_4$, pH 6, 8 mM tetrabutyl ammonium hydrogen sulfate to 75% acetonitrile. Absorbance was monitored at 254 nM.

Example D

Inhibition of Gluconeogenesis in Rat Hepatocytes

Hepatocytes were prepared from overnight fasted Sprague-Dawley rats (250–300 g) according to the procedure of Berry and Friend (Berry, M. N., Friend, D. S., J. Cell. Biol. 1969, 43, 506–520) as modified by Groen (Groen, A. K., Sips, H. J., Vervoorn, R. C., Tager, J. M., Eur. J Biochem. 1982, 122, 87–93). Hepatocytes (75 mg wet weight/mL) were incubated in 1 mL Krebs-bicarbonate buffer containing 10 mM Lactate, 1 mM pyruvate, 1 mg/mL BSA, and test compound concentrations from 1 to 500 µM. Incubations were carried out in a 95% oxygen, 5% carbon dioxide atmosphere in closed, 50-mL Falcon tubes submerged in a rapidly shaking water bath (37° C.). After 1 hour, an aliquot (0.25 mL) was removed, transferred to an Eppendorf tube and centrifuged. 50 µL of supernatant was then assayed for glucose content using a Sigma Glucose Oxidase kit as per the manufacturer's instructions.

Compounds 3.1, 5.1, 1.3, 9.1, 6.1, and 7.1 at 500 µM inhibited glucose production from lactate/pyruvate in isolated rat hepatocytes by 41.5%, 39.6%, 3.4%, 57.0%, 64.4%, and 45.4%, respectively. Compound 11.5 at 250 µM inhibited glucose production from lactate/pyruvate in isolated rat hepatocyte by 50%.

Figure 3:
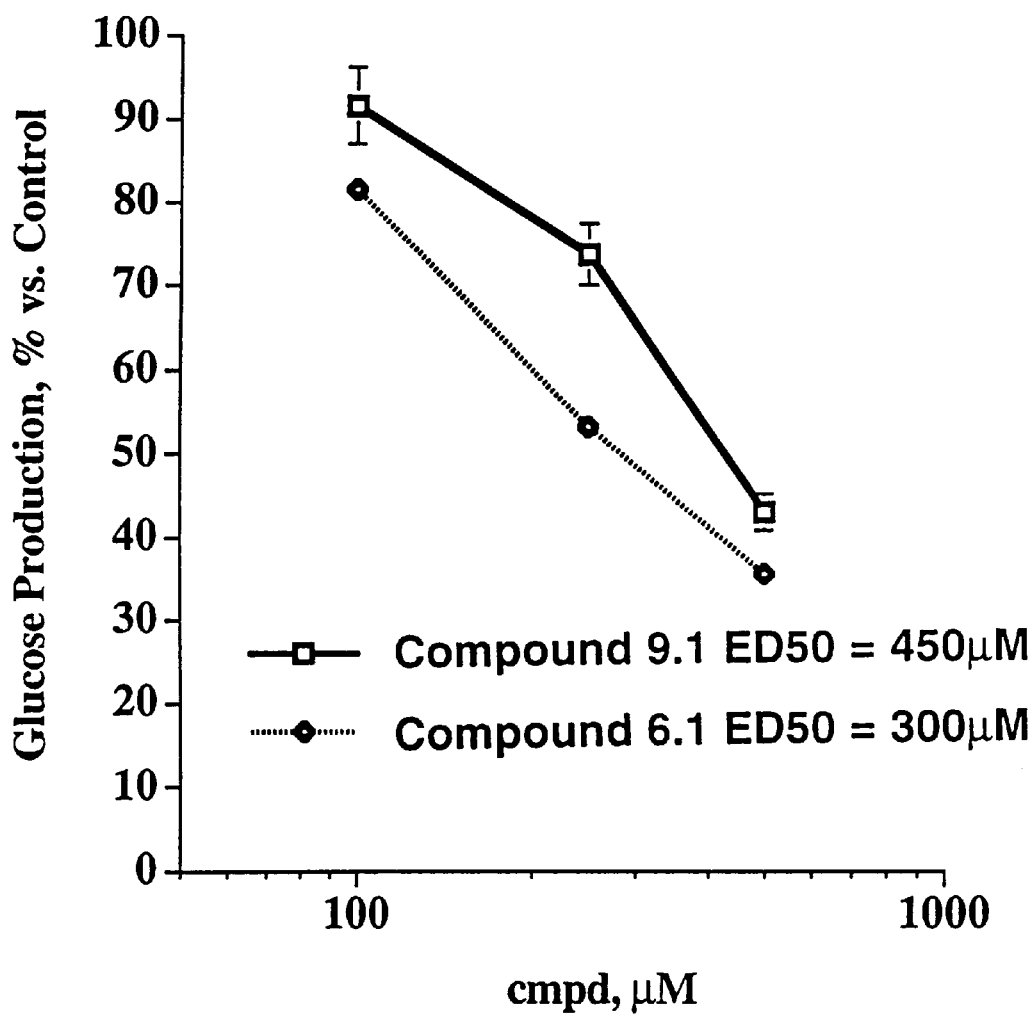
FIG. 3 depicts the dose dependent inhibition of glucose production in rat hepatocytes by compounds 9.1 and 6.1.

The ED$_{50}$ for compounds 9.1 and 6.1 are shown in FIG. 3, which demonstrates that these compounds inhibit glucose production in a dose dependent manner.

FBPase from rat liver is less sensitive to AMP than that from human liver. IC$_{50}$ values are correspondingly higher in rat hepatocytes than would be expected in human hepatocytes.

Example E

Blood Glucose Lowering in Fasted Rats

Sprague Dawley rats (250–300 g) are fasted for 18 hours and then dosed intraperitoneally with 20 mg/kg of test compound. The vehicle used for drug administration was 50 mM sodium bicarbonate. Blood samples are obtained from the tail vein of conscious animals just prior to injection and one hour post injection. Blood glucose is measured using a HemoCue Inc. glucose analyzer according to the instructions of the manufacturer.

Example F

Effect of FBPase Inhibitors on Gluconeogenesis from Lactate/pyruvate in Rat Hepatocytes: Glucose Production Inhibition and Fructose 1,6-bisphosphate Accumulation Isolated rat hepatocytes are prepared as described in Example D and incubated under the identical conditions described. Reactions are terminated by removing an aliquot (250 μL) of cell suspension and spinning it through a layer of oil (0.8 mL silicone/mineral oil, 4/1) into a 10% perchloric acid layer (100 μL). After removal of the oil layer, the acidic cell extract layer is neutralized by addition of ⅓rd volume of 3 M KOH/3 M KH$_2$CO$_3$. After thorough mixing and centrifugation, the supernatant is analyzed for glucose content as described in Example D, and also for fructose 1,6-bisphosphate. Fructose 1,6-bisphosphate is assayed spectrophotometrically by coupling its enzymatic conversion to glycerol 3-phosphate to the oxidation of NADH, which is monitored at 340 nm. Reaction mixtures (1 mL) consisted of 200 mM Tris-HCl, pH 7.4, 0.3 mM NADH, 2 units/mL glycerol 3-phosphate dehydrogenase, 2 units/mL triosephosphate isomerase, and 50–100 μL cell extract. After a 30 minute preincubation at 37° C., 1 unit/mL of aldolase is added and the change in absorbance measured until a stable value is obtained. Two moles of NADH are oxidized in this reaction per mole of fructose 1,6-bisphosphate present in the cell extract.

An inhibition of glucose production from lactate/pyruvate in rat hepatocytes and the accumulation of fructose 1,6 bisphosphate (the substrate of FBPase) is consistent with the inhibition of FBPase.

Example G

Analysis of Drug Levels and Liver Fructose-1,6-bisphosphate Accumulation in Rats Sprague-Dawley rats (250–300 g) are fasted for 18 hours and then dosed intraperitoneally either with saline (n=3) or 20 mgs/kg of FBPase inhibitor (n=4). The vehicle used for drug administration was 10 mM bicarbonate. One hour post injection rats are anesthetized with halothane and a liver biopsy (approx. 1 g) is taken as well as a blood sample (2 mL) from the posterior vena cava. A heparin flushed syringe and needle is used for blood collection. The liver sample is immediately homogenized in ice-cold 10% perchloric acid (3 mL), centrifuged, and the supernatant neutralized with ⅓rd volume of 3 M KOH/3 M KH$_2$CO$_3$. Following centrifugation and filtration, 50 μL of the neutralized extract was analyzed for FBPase inhibitor content by HPLC. A reverse phase YMC ODS AQ column (250×4.6 cm) is used and eluted with a gradient from 10 mM sodium phosphate pH 5.5 to 75% acetonitrile. Absorbance is monitored at 310 nm. The concentration of fructose-1,6-bisphosphate in liver is also quantified using the method described in Example F. Blood glucose is measured in the blood sample as described in Example D. Plasma is then quickly prepared by centrifugation and extracted by addition of methanol to 60% (v/v). The methanolic extract is clarified by centrifugation and filtration and then analyzed by HPLC as described above.

An elevation of fructose-1,6-bisphosphate levels in the livers from the drug-treated group is, consistent with the inhibition of glucose production at the level of FBPase in the gluconeogenic pathway.

Example H

Blood Glucose Lowering in Zucker Diabetic Fatty Rats

Zucker Diabetic Fatty rats purchased at 7 weeks of age are used at age 16 weeks in the 24-hour fasted state. The rats are purchased from Genetics Models Inc. and fed the recommended Purina 5008 diet (6.5% fat). Their fasting hyperglycemia at 24 hours generally ranges from 150 mg/dLto 310 mg/dLblood glucose.

FBPase inhibitor is administered at a dose of 50 mg/kg by intraperitoneal injection (n=6). The stock solution is made up at 25 mg/mL in deionized water and adjusted to neutrality by dropwise addition of 5 N NaOH. 5 control animals are dosed with saline. Blood glucose is measured at the time of dosing and 2 hours post dose as described in Example D.

Example I

Inhibition of Gluconeogenesis in Zucker Diabetic Fatty Rats

Three 20-week old Zucker Diabetic Fatty rats are dosed with FBPase inhibitor and three with saline as described in Example H. Fifteen minutes post-injection, the animals are anesthetized with sodium pentobarbitol (30 mgs, i.p.) and $^{14}$C-bicarbonate (20 μCi /100 g of body weight) is administered via the tail vein. Blood samples (0.6 mL) is obtained by cardiac puncture 10 and 20 minutes post tracer injection. Blood (0.5 mL) is diluted into 6 mL deionized water and protein precipitated by addition of 1 mL zinc sulfate (0.3 N ) and 1 mL barium hydroxide (0.3 N ). The mixture is centrifuged (20 minutes, 1000×g) and 5 mL of the resulting supernatant is then combined with 1 g of a mixed bed ion exchange resin (1 part AG 50W-X8, 100–200 mesh, hydrogen form and 2 parts of AG 1-X8, 100–200 mesh, acetate form) to separate $^{14}$C-bicarbonate from $^{14}$C-glucose. The slurry is shaken at room temperature for four hours and then allowed to settle. An aliquot of the supernatant (0.5 mL) was then counted in 5 mL scintillation cocktail.

A reduction in the incorporation of $^{14}$C-bicarbonate into glucose inidcates gluconeogenesis is inhibited by the drug.

Example J

Blood Glucose Lowering in Streptozotocin-treated Rats

Diabetes is induced in male Sprague-Dawley rats (250–300 g) by intraperitoneal injection of 55 mg/kg streptozotocin (Sigma Chemical Co.). Six days later, 24 animals are selected with fed blood glucose values (8 am) between 350 and 600 mg/dL and divided into two statistically equivalent groups. Blood glucose is measured in blood obtained from a tail vein nick by means of a HemoCue Inc. (Mission Viejo, Calif.) glucose analyzer. One group of 12 will subsequently receive inhibitor (100 mg/kg intraperitoneally) and the other 12 ("controls") an equivalent volume of saline. Food is removed from the animals. Blood glucose is measured in each animal four hours after dosing, and a second dose of drug or saline is then administered. Four hours later, a final blood glucose measurement is made.

Example K

Estimation of the Oral Bioavailability of Prodrugs of Phosphonic Acids

Prodrugs were dissolved in 10% ethanol/90% polyethylene glycol (mw 400) and administered by oral gavage at doses of approximately 20 or 40 mg/kg parent compound equivalents to 6-hour fasted, Sprague Dawley rats (220–240 g). The rats were subsequently placed in metabolic cages and urine was collected for 24 hours. The quantity of parent compound excreted into urine was determined by HPLC analysis. An ODS column eluted with a gradient from potassium phosphate buffer, pH 5.5 to acetonitrile was employed for these measurements. Detection was at 310–325 nm. The percentage oral bioavailability was estimated by comparison of the recovery in urine of the parent compound generated from the prodrug, to that recovered in urine 24 hours after intravenous administration of unsubstituted parent compound at approximately 10 mg/kg. Parent compounds were typically dissolved in dimethyl sulfoxide, and administered via the tail vein in animals that were briefly anesthetized with halothane.

Example M

Glucose Lowering Following Oral Administration of FBPase Inhibitors

FBPase inhibitor is administered by oral gavage at doses of 30, 100 and 250 mg/kg to 18-hour fasted, Sprague Dawley rats (250–300g; n=4–5/group). The compound is prepared in deionized water, adjusted to neutrality with sodium hydroxide, and brought into solution by sonication prior to administration. Blood glucose is measured immediately prior to dosing, and at 1 hour intervals thereafter. Blood samples are obtained from the tail vein, and measurments made by means of a Hemocue glucose analyzer (Hemocue Inc, Mission Viejo, Calif.) used according to the manufacturer's instructions.

We claim:

1. A compound of formula 1:

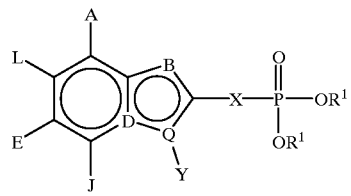

wherein:

B is selected from the group consisting of —NH—, and —CH=;

D is

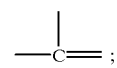

Q is selected from the group consisting of —C= and —N— with the proviso that when B is —NH— then Q is —C= and D is

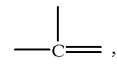

and when B is —CH= then Q is —N— and D is

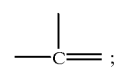

A, E, and L are selected from the group consisting of —NR$^8_2$, —NO$_2$, —H, —OR$^7$, —SR$^7$, —C(O)NR$^4_2$, halo, —COR$^{11}$, —SO$_2$R$^3$, guanidine, amidine, —NHSO$_2$R$^5$, —SO$_2$R$^4_2$, —CN, sulfoxide, perhaloacyl, perhaloalkyl, perhaloalkoxy, C1–C5 alkyl, C2–C5 alkenyl, C2–C5 alkynyl, and lower alicyclic, or together A and L form a cyclic group, or together L and E form a cyclic group, or together E and J form a cyclic group including aryl, cyclic alkyl, and heterocyclic;

J is selected from the group consisting of —NR$^8_2$, —NO$_2$, —H, —OR$^7$, —SR$^7$, —C(O)NR$^4_2$, halo, —C(O)R$^{11}$, —CN, sulfonyl, sulfoxide, perhaloalkyl, hydroxyalkyl, perhaloalkoxy, alkyl, haloalkyl, aminoalkyl, alkenyl, alkynyl, alicyclic, aryl, and aralkyl, or together with Y forms a cyclic group including aryl, cyclic alkyl and heterocyclic alkyl;

X is selected from the group consisting of alkylamino, alkyl(hydroxy), alkyl(carboxyl), alkyl(phosphonate), alkyl, alkenyl, alkynyl, alkyl(sulfonate), aryl, heteroaryl, carbonylalkyl, 1,1-dihaloalkyl, aminocarbonylamino, alkylaminoalkyl, alkoxyalkyl, alkylthioalkyl, alkylthio, alkylaminocarbonyl, alkylcarbonylamino, alicyclic, aralkyl, and alkylaryl, all optionally substituted by one to four substituents, independently selected from the group consisting of lower alkyl, lower aryl, lower aralkyl, lower alicyclic, hydroxy, lower alkoxy, lower aryloxy, perhaloalkoxy, aralkoxy, heteroaryl, heteroaryloxy, heteroarylalkyl, heteroaralkoxy, azido, amino, guanidino, haloen, lower alkylthio, oxa, ketone, carboxy esters, carboxyl, carboxamido, nitro, acyloxy, alkylamino, aminoalkyl, alkylaminoaryl, alkylaryl, alkylaminoalkyl, alkoxyaryl, arylamino, aralkylamino, phosphonate, sulfonate, carboxamidoalkylaryl, carboxamidoaryl, hydroxyalkyl, haloalkyl, alkylaminoalkylcarboxy, aminocarboxamidoalkyl, cyano, lower alkoxyalkyl, and lower perhaloalkyl; or together with Y forms a cyclic group including aryl, cyclic alkyl, and heterocyclic;

Y is selected from the group consisting of —H, alkyl, alkenyl, alkynyl, aryl, alicyclic, aralkyl, aryloxyalkyl, alkoxyalkyl, —C(O)R$^3$, —S(O)$_2$R$^3$, —C(O)—OR$^3$, —CONHR$^3$, —NR$^2_2$, —OR$^3$, all except H are optionally substituted; or together with X forms a cyclic group including aryl, cyclic alkyl, and heterocyclic;

R$^1$ is independently selected from the group consisting of —H, alkyl, aryl, alicyclic where the cyclic moiety contains a carbonate or thiocarbonate, —C(R²)₂-aryl, alkylaryl, —C(R²)₂OC(O)NR²₂, —NR²—C(O)—R³, —C(R²)₂—OC(O)R³, C(R²)₂—O—C(O)OR³, —C(R²)₂OC(O)SR³, alkyl-S—C(O)R³, alkyl-S—S-alkylhydroxy, and alkyl-S—S—S-alkylhydroxy, or together R¹ and R¹ are -alkyl-S—S-alkyl to form a cyclic group, or together R¹ and R¹ are

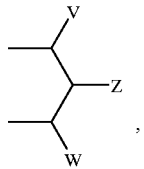

wherein

V and W are independently selected from the group consisting of hydrogen, aryl, substituted aryl, heteroaryl, substituted heteroaryl, 1-alkenyl, 1-alkynyl, and —R⁹; or together V and Z are connected to form a cyclic group containing 3–5 atoms, optionally 1 heteroatom, substituted with hydroxy, acyloxy, alkoxycarboxy, or aryloxycarboxy attached to a carbon atom that is three atoms from an oxygen attached to the phosphorus; or together V and W are connected to form a cyclic group containing 3 carbon atoms substituted with hydroxy, acyloxy, alkoxycarboxy, alkylthiocarboxy, hydroxymethyl, and aryloxycarboxy attached to a carbon atom that is three atoms from an oxygen attached to the phosphorus;

Z is selected from the group consisting of —CH₂OH, —CH₂OCOR³, —CH₂OC(O)SR³, —CH₂OCO₂R³, —SR³, —S(O)R³, —CH₂N₃, —CH₂NR²₂, —CH₂Ar, —CH(Ar)OH, —CH(CH=CR²R²)OH, —CH(C≡—CR²)OH, and —R²;

with the provisos that:

a) V, Z, W are not all —H; and b) when Z is —R², then at least one of V and W is not —H or —R⁹;

R² is selected from the group consisting of R³ and —H;

R³ is selected from the group consisting of alkyl, aryl, alicyclic, and aralkyl;

R⁴ is independently selected from the group consisting of —H, lower alkyl, lower alicyclic, lower aralkyl, and lower aryl;

R⁵ is selected from the group consisting of lower alkyl, lower aryl, lower aralkyl, and lower alicyclic;

R⁶ is independently selected from the group consisting of —H, and lower alkyl;

R⁷ is independently selected from the group consisting of —H, lower alkyl, lower alicyclic, lower aralkyl, lower aryl, and —C(O)R¹⁰;

R⁸ is independently selected from the group consisting of —H, lower alkyl, lower aralkyl, lower aryl, lower alicyclic, —C(O)R¹⁰, or together said R⁸ groups form a bidentate alkyl;

R⁹ is selected from the group consisting of alkyl, aralkyl, and alicyclic;

R¹⁰ is selected from the group consisting of —H, lower alkyl, —NH₂, lower aryl, and lower perhaloalkyl;

R¹¹ is selected from the group consisting of alkyl, aryl, —OH, —NH₂ and —OR³; and pharmaceutically acceptable prodrugs and salts thereof; with the provisos that:

a) R¹ is not lower alkyl of 1–4 carbon atoms;

b) X is not alkylamine and alkylaminoalkyl substituted with phosphonic esters or acids;

c) A, L, E, J, Y, and X together may only form 0–2 cyclic groups; and d) X is not aryl and alkylaryl linked 1,4 through a 6-membered aromatic ring.

2. The compounds of claim 1 wherein X is not substituted with a phosphonic acid or ester.

3. The compounds of claim 1 wherein when X is alkyl and alkene, then A is —N(R⁸)₂, and Y is not —H.

4. The compounds of claim 1 wherein A, L, and E are independently selected from the group consisting of —H, —NR⁸₂, —NO₂, hydroxy, halogen, —OR⁷, alkylaminocarbonyl, —SR⁷, lower perhaloalkyl, and C1–C5 alkyl, or together E and J together form a cyclic group.

5. The compounds of claim 4 wherein A, L and E are independently selected from the group consisting of —NR⁸₂, —H, hydroxy, halogen, lower alkoxy, lower perhaloalkyl, and lower alkyl.

6. The compounds of claim 1 wherein A is selected from the group consisting of —NR⁸₂, —H, halogen, lower perhaloalkyl, and lower alkyl.

7. The compounds of claim 1 wherein L and E are independently selected from the group consisting of -H, lower alkoxy, lower alkyl, and halogen.

8. The compounds of claim 1 wherein J is selected from the group consisting of —H, halogen, lower alkyl, lower hydroxyalkyl, —NR⁸₂, lower R⁸₂N-alkyl, lower haloalkyl, lower perhaloalkyl, lower alkenyl, lower alkynyl, lower aryl, heterocyclic, and alicyclic, or together with Y forms a cyclic group.

9. The compounds of claim 8 wherein J is selected from the group consisting of —H, halogen, lower alkyl, lower hydroxyalkyl, —NR⁸₂, lower R⁸₂N-alkyl, lower haloalkyl, lower alkenyl, alicyclic, and aryl.

10. The compounds of claim 1 wherein Y is selected from the group consisting of —H, aralkyl, aryl, alicyclic, and alkyl, all except —H may be optionally substituted.

11. The compounds of claim 10 wherein Y is selected from the group consisting of alicyclic and lower alkyl.

12. The compounds of claim 1 wherein X is selected from the group consisting of alkyl, alkynyl, alkoxyalkyl, alkylthio, aryl, heteroaryl, alkylaminocarbonyl, alkylcarbonylamino, 1,1-dihaloalkyl, carbonylalkyl, alkyl(OH), and alkyl(sulfonate).

13. The compounds of claim 12 wherein X is selected from the group consisting of heteroaryl, alkylaminocarbonyl, 1,1-dihaloalkyl, alkyl(sulfonate), and alkoxyalkyl.

14. The compounds of claim 13 wherein X is selected from the group consisting of heteroaryl, alkylaminocarbonyl, and alkoxyalkyl.

15. The compounds of claim 14 wherein X is selected from the group consisting of methylaminocarbonyl, methoxymethyl and furanyl.

16. The compounds of claim 1 wherein X is not C2–C3 alkylaminocarbonyl.

17. The compounds of claim 1 wherein each R¹ is independently selected from the group consisting of —H, alkyl, aryl, alicyclic where the cyclic moiety contains a carbonate or thiocarbonate, optionally substituted phenyl, optionally substituted benzyl, optionally substituted alkylaryl, —C(R²)₂OC(O)R³, C(R²)₂—O—C(O)OR³, —C(R²)₂—OC(O)SR³, -alkyl-S—C(O)R³, alkyl-S—S- alkylhydroxyl, and -alkyl-S—S—S-alkylhydroxy, or together R¹ and R¹ are alkyl-S—S-alkyl to form a cyclic group, or R¹ and R¹ together are

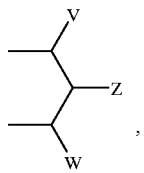

wherein

V and W are independently selected from the group consisting of hydrogen, aryl, substituted aryl, heteroaryl, substituted heteroaryl, 1-alkenyl, 1-alkynyl, and —R⁹; or together V and Z are connected to form a cyclic group containing 3–5 atoms, optionally 1 heteroatom, substituted with hydroxy, acyloxy, alkoxycarboxy, or aryloxycarboxy attached to a carbon atom that is three atoms from an oxygen attached to the phosphorus; or together V and W are connected to form a cyclic group containing 3 carbon atoms substituted with hydroxy, acyloxy, alkoxycarboxy, alkylthiocarboxy, hydroxymethyl, and aryloxycarboxy attached to a carbon atom that is three atoms from an oxygen attached to the phosphorus;

Z is selected from the group consisting of —CH₂OH, —CH₂OCOR³, —CH₂OC(O)SR³, —CH₂OCO₂R³, —SR³, —S(O)R³, —CH₂N₃, —CH₂NR²₂, —CH₂Ar, —CH(Ar)OH, —CH(CH=CR²R²)OH, —CH(C≡CR²)OH, and —R²;

with the provisos that:

a) V, Z, W are not all —H; and b) when Z is —R², then at least one of V and W is not —H or —R⁹;

R² is selected from the group consisting of R³ and —H;

R³ is selected from the group consisting of alkyl, aryl, alicyclic, and aralkyl;

R⁵ is selected from the group consisting of lower alkyl, lower aryl, lower aralkyl, and lower alicyclic; and R⁹ is selected from the group consisting of alkyl, aralkyl, and alicyclic.

18. The compounds of claim 17 wherein each R¹ is independently selected from the group consisting of optionally substituted phenyl, optionally substituted benzyl, —C(R²)₂OC(O)R³, and —H.

19. The compounds of claim 1 wherein R¹ is H.

20. The compounds of claim 17 wherein at least one R¹ is aryl, or C(R²)₂-aryl.

21. The compounds of claim 1 wherein at least one R¹ is —C(R²)₂—OC(O)R³, —C(R²)₂—OC(O)OR³, —C(R²)₂—OC(O)SR³.

22. The compounds of claim 17 wherein at least one R¹ is -alkyl-S—S-alkylhydroxyl, -alkyl-S—C(O)R³, and -alkyl-S—S—S-alkylhydroxy, or together R¹ and R¹ are alkyl-S—S-alkyl to form a cyclic group.

23. The compounds of claim 1 wherein together R¹ and R¹ are

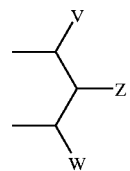

V and W are independently selected from the group consisting of hydrogen, aryl, substituted aryl, heteroaryl, substituted heteroaryl, 1-alkenyl, 1-alkynyl, and —R⁹; or together V and Z are connected to form a cyclic group containing 3–5 atoms, optionally 1 heteroatom, substituted with hydroxy, acyloxy, alkoxycarboxy, or aryloxycarboxy attached to a carbon atom that is three atoms from an oxygen attached to the phosphorus; or together V and W are connected to form a cyclic group containing 3 carbon atoms substituted with hydroxy, acyloxy, alkoxycarboxy, alkylthiocarboxy, hydroxymethyl, and aryloxycarboxy attached to a carbon atom that is three atoms from an oxygen attached to the phosphorus;

Z is selected from the group consisting of —CH₂OH, —CH₂OCOR³, —CH₂OC(O)SR³, —CH₂OCO₂R³, —SR³, —S(O)R³, —CH₂N₃ —CH₂NR²₂, —CH₂Ar, —CH(Ar)OH, —CH(CH=CR²R²)OH, —CH(C≡CR²)OH, and —R²;

with the provisos that:

a) V, Z, W are not all —H; and b) when Z is —R², then at least one of V and W is not —H or —R⁹;

R² is selected from the group consisting of R³ and —H;

R³ is selected from the group consisting of alkyl, aryl, alicyclic, and aralkyl; and R⁹ is selected from the group consisting of alkyl, aralkyl, and alicyclic.

24. The compounds of claim 23 wherein V and W both form a 6-membered carbocyclic ring substituted with 0–4 groups, selected from the group consisting of hydroxy, acyloxy, alkoxycarbonyloxy, and alkoxy; and Z is —R².

25. The compounds of claim 23 wherein V and W are hydrogen; and Z is selected from the group consisting of hydrogen, hydroxyalkyl, acyloxyalkyl, alkyloxyalkyl, and alkoxycarbonyloxy.

26. The compounds of claim 23 wherein V and W are independently selected from the group consisting of hydrogen, optionally substituted aryl, and optionally substituted heteroaryl, with the proviso that at least one of V and W is optionally substituted aryl or optionally substituted heteroaryl.

27. The compounds of claim 1 wherein together R¹ and R¹ are optionally substituted lactones attached at the omega position.

28. The compounds of claim 17 wherein R¹ is alicyclic where the cyclic moiety contains carbonate or thiocarbonate.

29. The compounds of claim 28 wherein together R¹ and R¹ are optionally substituted 2-oxo-1,3-dioxolenes attached through a methylene to the phosphorus.

30. The compounds of claim 1 wherein B is NH, D is

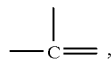

and Q is —C=.

31. The compounds of claim 1 wherein
A, L and E are independently selected from the group consisting of —NR$^8_2$, —H, hydroxy, halogen, lower alkoxy, lower alkyl, and lower perhaloalkyl;
X is selected from the group consisting of aryl, heteroaryl, alkoxyalkyl, alkyl, alkylthio, 1,1-dihaloalkyl, carbonylalkyl, alkyl(hydroxy), alkyl(sulfonate), alkylaminocarbonyl, and alkylcarbonylamino;
and each R$^4$ and R$^7$ is independently selected from the group consisting of —H and lower alkyl.

32. The compounds of claim 31 wherein A, L, and E are independently selected from the group consisting of —H, lower alkyl, halogen, and —NR$^8_2$;
J is selected from the group consisting of —H, halogen, haloalkyl, hydroxyalkyl, —R$^8_2$N-alkyl, lower alkyl, lower aryl, heterocyclic and alicyclic, or together with Y forms a cyclic group; and
X is selected from the group consisting of heteroaryl, alkylaminocarbonyl, 1,1-dihaloalkyl, and alkoxyalkyl.

33. The compounds of claim 32 wherein A is selected from the group consisting of —H, —NH$_2$, —F, and —CH$_3$;
L is selected from the group consisting of —H, —F, —OCH$_3$, and —CH$_3$;
E is selected from the group consisting of —H, and —Cl;
J is selected from the group consisting of —H, halo, C1–C5 hydroxyalkyl, C1–C5 haloalkyl, C1–C5 R$^8_2$N-alkyl C1–C5 alicyclic, and C1–C5 alkyl;
X is —CH$_2$OCH$_2$-, 2,5-furanyl; and
Y is lower alkyl.

34. The compounds of claim 33 wherein B is NH, D is

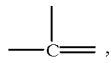

and Q is —C=.

35. The compounds of claim 32 wherein
J is selected from the group consisting of —H, halogen, lower alkyl, lower aryl, heterocyclic, and alicyclic, or together with Y forms a cyclic group; and
X is selected from the group consisting of heteroaryl, alkylaminocarbonyl, and alkoxyalkyl.

36. The compounds of claim 33 where A is —NH$_2$, L is —F, E is —H, J is —H, Y is isobutyl, and X is 2,5-furanyl.

37. The compounds of claim 33 where A is —NH$_2$, L is —F, E is —H, J is —Cl, Y is isobutyl, and X is 2,5-furanyl.

38. The compounds of claim 33 wherein A is —H, L is —H, E is —Cl, J is —H, B is —NH, D is

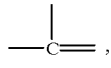

Q is —C=, and Y is isobutyl.

39. The compounds of claim 38 wherein R$^1$ is —CH$_2$OC(O)—C(CH$_3$)$_3$.

40. A method of treating an animal for diabetes mellitus, comprising administering to said animal a therapeutically effective amount of a compound of formula (1):

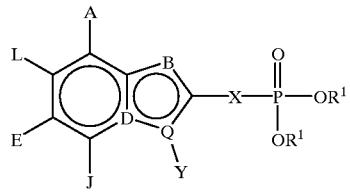

wherein:
B is selected from the group consisting of—NH—, and —CH=;
D is

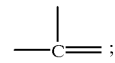

Q is selected from the group consisting of —C= and —N— with the proviso that when B is —NH— then Q is —C= and D is

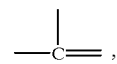

and when B is —CH= then Q is

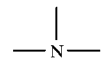

and D is —C=;
A, E, and L are selected from the group consisting of —NR$^8_2$, —NO$_2$, —H, —OR$^7$, —SR$^7$, —C(O)NR$^4_2$, halo, —COR$^{11}$, —SO$_2$R$^3$, guanidine, amidine, —NHSO$_2$R$^5$, —SO$_2$NR$^4_2$, —CN, sulfoxide, perhaloacyl, perhaloalkyl, perhaloalkoxy, C1–C5 alkyl, C2–C5 alkenyl, C2–C5 alkynyl, and lower alicyclic, or together A and L form a cyclic group, or together L and E form a cyclic group, or together E and J form a cyclic group including aryl, cyclic alkyl, and heterocyclic;
J is selected from the group consisting of—NR$^8_2$, —NO$_2$, —H, —OR$^7$, —SR$^7$, —C(O)NR$^4_2$, halo, —C(O)R$^{11}$, —CN, sulfonyl, sulfoxide, perhaloalkyl, hydroxyalkyl, perhaloalkoxy, alkyl, haloalkyl, aminoalkyl, alkenyl, alkynyl, alicyclic, aryl, and aralkyl, or together with Y forms a cyclic group including aryl, cyclic alkyl and heterocyclic alkyl;
X is selected from the group consisting of alkylamino, alkyl(hydroxy), alkyl(carboxyl), alkyl(phosphonate), alkyl, alkenyl, alkynyl, alkyl(sulfonate), aryl, heteroaryl, carbonylalkyl, 1,1-dihaloalkyl, aminocarbonylamino, alkylaminoalkyl, alkoxyalkyl, alkylthioalkyl, alkylthio, alkylaminocarbonyl, alkylcarbonylamino, alicyclic, aralkyl, and alkylaryl, all optionally substituted; or together with Y forms a cyclic group including aryl, cyclic alkyl, and heterocyclic;
Y is selected from the group consisting of —H, alkyl, alkenyl, alkynyl, aryl, alicyclic, aralkyl, aryloxyalkyl, alkoxyalkyl, —C(O)R$^3$, —S(O)$_2$R$^3$, —C(O)—OR$^3$, —CONHR$^3$, —NR$^2_2$, and —OR$^3$, all except H are optionally substituted; or together with X forms a cyclic group including aryl, cyclic alkyl, and heterocyclic;

R' is independently selected from the group consisting of —H, alkyl, aryl, alicyclic where the cyclic moiety contains a carbonate or thiocarbonate, —C(R²)₂-aryl, alkylaryl, —C(R²)₂OC(O)NR²₂, —NR²—C(O)—R³, —C(R²)₂—OC(O)R³, C(R²)₂—O—C(O)OR³, —C(R²)₂OC(O)SR³, alkyl-S—C(O)R³, alkyl-S—S-alkylhydroxy, and alkyl-S—S—S-alkylhydroxy, or together R¹ and R¹ are -alkyl-S—S-alkyl to form a cyclic group, or together R¹ and R¹ are

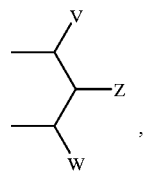

wherein
V and W are independently selected from the group consisting of hydrogen, aryl, substituted aryl, heteroaryl, substituted heteroaryl, 1-alkenyl, 1-alkynyl, and —R⁹; or together V and Z are connected to form a cyclic group containing 3–5 atoms, optionally 1 heteroatom, substituted with hydroxy, acyloxy, alkoxycarboxy, or aryloxycarboxy attached to a carbon atom that is three atoms from an oxygen attached to the phosphorus; or together V and W are connected to form a cyclic group containing 3 carbon atoms substituted with hydroxy, acyloxy, alkoxycarboxy, alkylthiocarboxy, hydroxymethyl, and aryloxycarboxy attached to a carbon atom that is three atoms from an oxygen attached to the phosphorus;

Z is selected from the group consisting of —CH₂OH, —CH₂OCOR³, —CH₂OC(O)SR³, —CH₂OCO₂R³, —SR³, —S(O)R³, —CH₂N₃, —CH₂NR²₂, —CH₂Ar, —CH(Ar)OH, —CH(CH=CR²R²)OH, —CH(C≡CR²)OH, and —R²;

with the provisos that:
a) V, Z, W are not all —H; and
b) when Z is —R², then at least one of V and W is not —H or —R⁹;

R² is selected from the group consisting of R³ and —H;
R³ is selected from the group consisting of alkyl, aryl, alicyclic, and aralkyl;
R⁴ is independently selected from the group consisting of —H, lower alkyl, lower alicyclic, lower aralkyl, and lower aryl;
R⁵ is selected from the group consisting of lower alkyl, lower aryl, lower aralkyl, and lower alicyclic;
R⁶ is independently selected from the group consisting of —H, and lower alkyl;
R⁷ is independently selected from the group consisting of —H, lower alkyl, lower alicyclic, lower aralkyl, lower aryl, and —C(O)R¹⁰;
R⁸ is independently selected from the group consisting of —H, lower alkyl, lower aralkyl, lower aryl, lower alicyclic, —C(O)R¹⁰, or together said R⁸ groups form a bidentate alkyl;
R⁹ is selected from the group consisting of alkyl, aralkyl, and alicyclic;

R¹⁰ is selected from the group consisting of —H, lower alkyl, —NH₂, lower aryl, and lower perhaloalkyl;
R¹¹ is selected from the group consisting of alkyl, aryl, —OH, —NH₂ and —OR³; and
pharmaceutically acceptable prodrugs and salts thereof.

41. A method of lowering blood glucose levels in an animal in need thereof, comprising administering to said animal a pharmaceutically acceptable amount of a compound of formula (1):

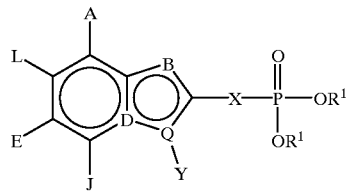

wherein:
B is selected from the group consisting of —NH—, and —CH=;
D is

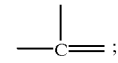

Q is selected from the group consisting of —C= and —N— with the proviso that when B is —NH— then Q is —C= and D is

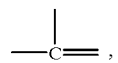

and when B is —CH= then Q is

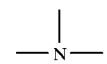

and D is —C=;
A, E, and L are selected from the group consisting of —NR⁸₂, —NO₂, -H, —OR⁷, —SR⁷, —C(O)NR⁴₂, halo, —COR¹¹, —SO₂R³, guanidine, amidine, —NHSO₂R⁵, —SO₂NR⁴₂, —CN, sulfoxide, perhaloacyl, perhaloalkyl, perhaloalkoxy, C1–C5 alkyl, C2–C5 alkenyl, C2–C5 alkynyl, and lower alicyclic, or together A and L form a cyclic group, or together L and E form a cyclic group, or together E and J form a cyclic group including aryl, cyclic alkyl, and heterocyclic;
J is selected from the group consisting of —NR⁸₂, —NO₂, —H, —OR⁷, —SR⁷, —C(O)NR⁴₂, halo, C(O)R¹¹, —CN, sulfonyl, sulfoxide, perhaloalkyl, hydroxyalkyl, perhaloalkoxy, alkyl, haloalkyl, aminoalkyl, alkenyl, alkynyl, alicyclic, aryl, and aralkyl, or together with Y forms a cyclic group including aryl, cyclic alkyl and heterocyclic alkyl;
X is selected from the group consisting of alkylamino, alkyl(hydroxy), alkyl(carboxyl), alkyl(phosphonate), alkyl, alkenyl, alkynyl, alkyl(sulfonate), aryl, heteroaryl, carbonylalkyl, 1,1-dihaloalkyl, aminocarbonylamino, alkylaminoalkyl, alkoxyalkyl, alkylthioalkyl, alkylthio, alkylaminocarbonyl, alkylcarbonylamino, alicyclic, aralkyl, and alkylaryl, all optionally substituted; or together with Y forms a cyclic group including aryl, cyclic alkyl, and heterocyclic;

Y is selected from the group consisting of —H, alkyl, alkenyl, alkynyl, aryl, alicyclic, aralkyl, aryloxyalkyl, alkoxyalkyl, —C(O)R$^3$, —S(O)$_2$R$^3$, —C(O)—OR$^3$, —CONHR$^3$, —NR$^2{}_2$, and —OR$^3$, all except H are optionally substituted; or together with X forms a cyclic group including aryl, cyclic alkyl, and heterocyclic;

R$^1$ is independently selected from the group consisting of —H, alkyl, aryl, alicyclic where the cyclic moiety contains a carbonate or thiocarbonate, —C(R$^2$)$_2$-aryl, alkylaryl, —C(R$^2$)$_2$OC(O)NR$^2{}_2$, —NR$^2$—C(O)—R$^3$, —C(R$^2$)$_2$—OC(O)R$^3$, C(R$^2$)$_2$—O—C(O)OR$^3$, —C(R$^2$)$_2$OC(O)SR$^3$, alkyl-S—C(O)R$^3$, alkyl-S—S-alkylhydroxy, and alkyl-S—S—S-alkylhydroxy, or together R$^1$ and R$^1$ are -alkyl-S—S-alkyl to form a cyclic group, or together R$^1$ and R$^1$ are

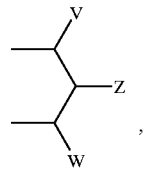

wherein
V and W are independently selected from the group consisting of hydrogen, aryl, substituted aryl, heteroaryl, substituted heteroaryl, 1-alkenyl, 1-alkynyl, and —R$^9$; or together V and Z are connected to form a cyclic group containing 3–5 atoms, optionally 1 heteroatom, substituted with hydroxy, acyloxy, alkoxycarboxy, or aryloxycarboxy attached to a carbon atom that is three atoms from an oxygen attached to the phosphorus; or together V and W are connected to form a cyclic group containing 3 carbon atoms substituted with hydroxy, acyloxy, alkoxycarboxy, alkylthiocarboxy, hydroxymethyl, and aryloxycarboxy attached to a carbon atom that is three atoms from an oxygen attached to the phosphorus;

Z is selected from the group consisting of —CH$_2$OH, —CH$_2$OCOR$^3$, —CH$_2$OC(O)SR$^3$, —CH$_2$OCO$_2$R$^3$, —SR$^3$, —S(O)R$^3$, —CH$_2$N$_3$, —CH$_2$NR$^2{}_2$, —CH$_2$Ar, —CH(Ar)OH, —CH(CH=CR$^2$R$^2$)OH, —CH(C≡CR$^2$)OH, and —R$^2$;

with the provisos that:
a) V, Z, W are not all —H; and
b) when Z is —R$^2$, then at least one of V and W is not —H or —R$^9$;

R$^2$ is selected from the group consisting of R$^3$ and —H;
R$^3$ is selected from the group consisting of alkyl, aryl, alicyclic, and aralkyl;
R$^4$ is independently selected from the group consisting of —H, lower alkyl, lower alicyclic, lower aralkyl, and lower aryl;
R$^5$ is selected from the group consisting of lower alkyl, lower aryl, lower aralkyl, and lower alicyclic;
R is independently selected from the group consisting of —H, and lower alkyl;
R$^7$ is independently selected from the group consisting of —H, lower alkyl, lower alicyclic, lower aralkyl, lower aryl, and —C(O)R$^{10}$;

R$^8$ is independently selected from the group consisting of —H, lower alkyl, lower aralkyl, lower aryl, lower alicyclic, —C(O)R$^{10}$, or together said R$^8$ groups form a bidentate alkyl;

R$^9$ is selected from the group consisting of alkyl, aralkyl, and alicyclic;

R$^{10}$ is selected from the group consisting of —H, lower alkyl, —NH$_2$, lower aryl, and lower perhaloalkyl, R$^{11}$ is selected from the group consisting of alkyl, aryl, —OH, —NH$_2$ and —OR$^3$; and pharmaceutically acceptable prodrugs and salts thereof.

42. A method of inhibiting FBPasc at the AMP site in patients in need thereof, comprising administering to said patients a compound of formula (1):

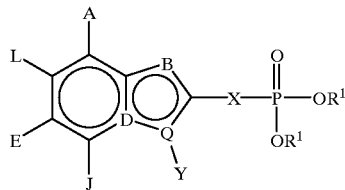

wherein:
B is selected from the group consisting of —NH—, and —CH=;
D is

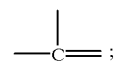

Q is selected from the group consisting of —C= and —N— with the proviso that when B is —NH— then Q is —C= and D is

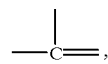

and when B is —CH= then Q is

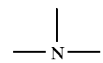

and D is —C=;

A, E, and L are selected from the group consisting of —NR$^8{}_2$, —NO$_2$, —H, —OR$^7$, —SR$^7$, —C(O)NR$^4{}_2$, halo, —COR$^{11}$, —SO$_2$R$^3$, guanidine, amidine, —NHSO$_2$R$^5$, —SO$_2$NR$^4{}_2$, —CN, sulfoxide, perhaloacyl, perhaloalkyl, perhaloalkoxy, C1–C5 alkyl, C2–C5 alkenyl, C2–C5 alkynyl, and lower alicyclic, or together A and L form a cyclic group, or together L and E form a cyclic group, or together E and J form a cyclic group including aryl, cyclic alkyl, and heterocyclic;

J is selected from the group consisting of —NR$^8{}_2$, —NO$_2$, —H, —OR$^7$, —SR$^7$, —C(O)NR$^4{}_2$, halo, —C(O)R$^{11}$, —CN, sulfonyl, sulfoxide, perhaloalkyl, hydroxyalkyl, perhaloalkoxy, alkyl, haloalkyl, aminoalkyl, alkenyl, alkynyl, alicyclic, aryl, and aralkyl, or together with Y forms a cyclic group including aryl, cyclic alkyl and heterocyclic alkyl;

X is selected from the group consisting of alkylamino, alkyl(hydroxy), alkyl(carboxyl), alkyl(phosphonate), alkyl, alkenyl, alkynyl, alkyl(sulfonate), aryl, heteroaryl, carbonylalkyl, 1,1-dihaloalkyl, aminocarbonylamino, alkylaminoalkyl, alkoxyalkyl, alkylthioalkyl, alkylthio, alkylaminocarbonyl, alkylcarbonylamino, alicyclic, aralkyl, and alkylaryl, all optionally substituted; or together with Y forms a cyclic group including aryl, cyclic alkyl, and heterocyclic;

Y is selected from the group consisting of —H, alkyl, alkenyl, alkynyl, aryl, alicyclic, aralkyl, aryloxyalkyl, alkoxyalkyl, —C(O)R$^3$, —S(O)$_2$R$^3$, —C(O)—OR$^3$, —CONHR$^3$, —NR$^2{}_2$, and —OR$^3$, all except H are optionally substituted; or together with X forms a cyclic group including aryl, cyclic alkyl, and heterocyclic;

R$^1$ is independently selected from the group consisting of —H, alkyl, aryl, alicyclic where the cyclic moiety contains a carbonate or thiocarbonate, —C(R$^2$)$_2$-aryl, alkylaryl, —C(R$^2$)$_2$OC(O)NR$^2{}_2$, —NR$^2$—C(O)—R$^3$, —C(R$^2$)$_2$—OC(O)R$^3$, C(R$^2$)$_2$—O—C(O)OR$^3$, —C(R$^2$)$_2$OC(O)SR$^3$, alkyl-S—C(O)R$^3$, alky-S—S-alkylhydroxy, and alkyl-S—S—S-alkylhydroxy, or together R$^1$ and R$^1$ are -alkyl-S—S-alkyl to form a cyclic group, or together R$^1$ and R$^1$ are

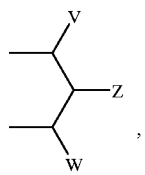

wherein
V and W are independently selected from the group consisting of hydrogen, aryl, substituted aryl, heteroaryl, substituted heteroaryl, 1-alkenyl, 1-alkynyl, and —R$^9$; or together V and Z are connected to form a cyclic group containing 3–5 atoms, optionally 1 heteroatom, substituted with hydroxy, acyloxy, alkoxycarboxy, or aryloxycarboxy attached to a carbon atom that is three atoms from an oxygen attached to the phosphorus; or together V and W are connected to form a cyclic group containing 3 carbon atoms substituted with hydroxy, acyloxy, alkoxycarboxy, alkylthiocarboxy, hydroxymethyl, and aryloxycarboxy attached to a carbon atom that is three atoms from an oxygen attached to the phosphorus;

Z is selected from the group consisting of —CH$_2$OH, —CH$_2$OCOR$^3$, —CH$_2$OC(O)SR$^3$, —CH$_2$OCO$_2$R$^3$, —SR$^3$, —S(O)R$^3$, —CH$_2$N$_3$, —CH$_2$NR$^2{}_2$, —CH$_2$Ar, —CH(Ar)OH, —CH(CH=CR$^2$R$^2$)OH, —CH(C≡CR2)OH, and —R$^2$;

with the provisos that:
a) V, Z, W are not all —H; and
b) when Z is —R$^2$, then at least one of V and W is not —H or —R$^9$;

R$^2$ is selected from the group consisting of R$^3$ and —H;
R$^3$ is selected from the group consisting of alkyl, aryl, alicyclic, and aralkyl;
R$^4$ is independently selected from the group consisting of —H, lower alkyl, lower alicyclic, lower aralkyl, and lower aryl;

R$^5$ is selected from the group consisting of lower alkyl, lower aryl, lower aralkyl, and lower alicyclic;
R$^6$ is independently selected from the group consisting of —H, and lower alkyl;
R$^7$ is independently selected from the group consisting of —H, lower alkyl, lower alicyclic, lower aralkyl, lower aryl, and —C(O)R$^{10}$;
R$^8$ is independently selected from the group consisting of —H, lower alkyl, lower aralkyl, lower aryl, lower alicyclic, —C(O)R$^{10}$, or together said R$^8$ groups form a bidentate alkyl;
R$^9$ is selected from the group consisting of alkyl, aralkyl, and alicyclic;
R is selected from the group consisting of —H, lower alkyl, —NH$_2$, lower aryl, and lower perhaloalkyl;
R$^{11}$ is selected from the group consisting of alkyl, aryl, —OH, —NH$_2$ and —OR$^3$; and
pharmaceutically acceptable prodrugs and salts thereof.

43. A method of inhibiting gluconeogenesis in an animal in need thereof, comprising administering to said animal an FBPase inhibitory amount of a compound of formula (1):

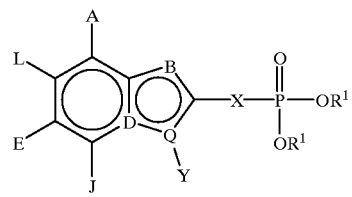

wherein:
B is selected from the group consisting of —NH—, and —CH=;
D is

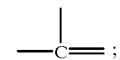

;

Q is selected from the group consisting of —C= and —N— with the proviso that when B is —NH— then Q is —C= and D is

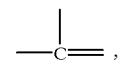

, and when B is —CH= then Q is

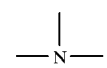

and D is —C=;

A, E, and L are selected from the group consisting of —NR$^8{}_2$, —NO$_2$, —H, —OR$^7$, —SR$^7$, —C(O)NR$^4{}_2$, halo, —COR$^{11}$, —SO$_2$R$^3$, guanidine, amidine, —NHSO$_2$R$^5$, —SO$_2$NR$^4{}_2$, —CN, sulfoxide, perhaloacyl, perhaloalkyl, perhaloalkoxy, C1–C5 alkyl, C2–C5 alkenyl, C2–C5 alkynyl, and lower alicyclic, or together A and L form a cyclic group, or together L and E form a cyclic group, or together E and J form a cyclic group including aryl, cyclic alkyl, and heterocyclic;

J is selected from the group consisting of —NR$^8_2$, —NO$_2$, —H, —OR$^7$, —SR$^7$, —C(O)NR$^4_2$, halo, —C(O)R$^{11}$, —CN, sulfonyl, sulfoxide, perhaloalkyl, hydroxyalkyl, perhaloalkoxy, alkyl, haloalkyl, aminoalkyl, alkenyl, alkynyl, alicyclic, aryl, and aralkyl, or together with Y forms a cyclic group including aryl, cyclic alkyl and heterocyclic alkyl;

X is selected from the group consisting of alkylamino, alkyl(hydroxy), alkyl(carboxyl), alkyl(phosphonate), alkyl, alkenyl, alkynyl, alkyl(sulfonate), aryl, heteroaryl, carbonylalkyl, 1,1-dihaloalkyl, aminocarbonylamino, alkylaminoalkyl, alkoxyalkyl, alkylthioalkyl, alkylthio, alkylaminocarbonyl, alkylcarbonylamino, alicyclic, aralkyl, and alkylaryl, all optionally substituted; or together with Y forms a cyclic group including aryl, cyclic alkyl, and heterocyclic;

Y is selected from the group consisting of —H, alkyl, alkenyl, alkynyl, aryl, alicyclic, aralkyl, aryloxyalkyl, alkoxyalkyl, —C(O)R$^3$, —S(O)$_2$R$^3$, —C(O)—OR$^3$, —CONHR$^3$, —NR$^2_2$, and —OR$^3$, all except H are optionally substituted; or together with X forms a cyclic group including aryl, cyclic alkyl, and heterocyclic;

R$^1$ is independently selected from the group consisting of —H, alkyl, aryl, alicyclic where the cyclic moiety contains a carbonate or thiocarbonate, —C(R$^2$)$_2$-aryl, alkylaryl, —C(R$^2$)$_2$OC(O)NR$^2_2$, —NR$^2$—C(O)—R$^3$, —C(R$^2$)$_2$—OC(O)R$^3$, C(R$^2$)$_2$—O—C(O)OR$^3$, —C(R$^2$)2OC(O)SR$^3$, alkyl-S—C(O)R$^3$, alkyl-S—S—alkylhydroxy, and alkyl-S—S—S-alkylhydroxy, or together R$^1$ and R$^1$ are -alkyl-S—S-alkyl to form a cyclic group, or together R$^1$ and R$^1$ are

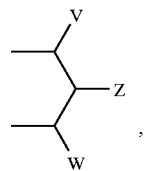

wherein
V and W are independently selected from the group consisting of hydrogen, aryl, substituted aryl, heteroaryl, substituted heteroaryl, 1-alkenyl, 1-alkynyl, and —R$^9$; or together V and Z are connected to form a cyclic group containing 3–5 atoms, optionally 1 heteroatom, substituted with hydroxy, acyloxy, alkoxycarboxy, or aryloxycarboxy attached to a carbon atom that is three atoms from an oxygen attached to the phosphorus; or together V and W are connected to form a cyclic group containing 3 carbon atoms substituted with hydroxy, acyloxy, alkoxycarboxy, alkylthiocarboxy, hydroxymethyl, and aryloxycarboxy attached to a carbon atom that is three atoms from an oxygen attached to the phosphorus;

Z is selected from the group consisting of —CH$_2$OH, —CH$_2$OCOR$^3$, —CH$_2$OC(O)SR$^3$, —CH$_2$OCO$_2$R$^3$, —SR$^3$, —S(O)R$^3$, —CH$_2$N$_3$, —CH$_2$NR$^2_2$, —CH$_2$Ar, —CH(Ar)OH, —CH(CH=CR$^2$R$^2$)OH, —CH(C≡CR$^2$)OH, and —R$^2$;

with the provisos that:
a) V, Z, W are not all —H; and
b) when Z is —R$^2$, then at least one of V and W is not —H or —R$^9$;

R$^2$ is selected from the group consisting of R$^3$ and —H;

R$^3$ is selected from the group consisting of alkyl, aryl, alicyclic, and aralkyl;

R$^4$ is independently selected from the group consisting of —H, lower alkyl, lower alicyclic, lower aralkyl, and lower aryl;

R$^5$ is selected from the group consisting of lower alkyl, lower aryl, lower aralkyl, and lower alicyclic;

R$^6$ is independently selected from the group consisting of —H, and lower alkyl;

R$^7$ is independently selected from the group consisting of —H, lower alkyl, lower alicyclic, lower aralkyl, lower aryl, and —C(O)R$^{10}$;

R$^8$ is independently selected from the group consisting of —H, lower alkyl, lower aralkyl, lower aryl, lower alicyclic, —C(O)R$^{10}$, or together said R$^8$ groups form a bidentate alkyl;

R$^9$ is selected from the group consisting of alkyl, aralkyl, and alicyclic;

R$^{10}$ is selected from the group consisting of —H, lower alkyl, —NH$_2$, lower aryl, and lower perhaloalkyl;

R$^{11}$ is selected from the group consisting of alkyl, aryl, —OH, —NH$_2$ and —OR$^3$; and pharmaceutically acceptable prodrugs and salts thereof.

44. A method of treating an animal for a disease derived from abnormally elevated insulin levels, comprising administering to said animal a therapeutically effective amount of a fructose-1,6-bisphosphatase inhibitor which binds to the AMP site of FBPase wherein said inhibitor is a compound of formula (1):

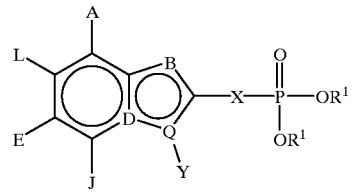

wherein:

B is selected from the group consisting of —NH—, and —CH=;

D is

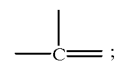

;

Q is selected from the group consisting of—C= and —N— with the proviso that when B is —NH— then Q is —C= and D is

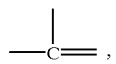

and when B is —CH= then Q is

and D is —C=;

A, E, and L are selected from the group consisting of —NR$^8_2$, —NO$_2$, —H, —OR$^7$, —SR$^7$, —C(O)NR$^4_2$, halo, —COR$^{11}$, —SO$_2$R$^3$, guanidine, amidine, —NHSO$_2$R$^5$, —SO$_2$NR$^4_2$, —CN, sulfoxide, perhaloacyl, perhaloalkyl, perhaloalkoxy, C1–C5 alkyl, C2–C5 alkenyl, C2–C5 alkynyl, and lower alicyclic, or together A and L form a cyclic group, or together L and E form a cyclic group, or together E and J form a cyclic group including aryl, cyclic alkyl, and heterocyclic;

J is selected from the group consisting of —NR$^8_2$, —NO$_2$, —H, —OR$^7$, —SR$^7$, —C(O)NR$^4_2$, halo, —C(O)R$^{11}$, —CN, sulfonyl, sulfoxide, perhaloalkyl, hydroxyalkyl, perhaloalkoxy, alkyl, haloalkyl, aminoalkyl, alkenyl, alkynyl, alicyclic, aryl, and aralkyl, or together with Y forms a cyclic group including aryl, cyclic alkyl and heterocyclic alkyl;

X is selected from the group consisting of alkylamino, alkyl(hydroxy), alkyl(carboxyl), alkyl(phosphonate), alkyl, alkenyl, alkynyl, alkyl(sulfonate), aryl, heteroaryl, carbonylalkyl, 1,1-dihaloalkyl, aminocarbonylamino, alkylaminoalkyl, alkoxyalkyl, alkylthioalkyl, alkylthio, alkylaminocarbonyl, alkylcarbonylamino, alicyclic, aralkyl, and alkylaryl, all optionally substituted; or together with Y forms a cyclic group including aryl, cyclic alkyl, and heterocyclic;

Y is selected from the group consisting of -H, alkyl, alkenyl, alkynyl, aryl, alicyclic, aralkyl, aryloxyalkyl, alkoxyalkyl, —C(O)R$^3$, —S(O)2R$^3$, —C(O)—OR$^3$, —CONHR$^3$, —NR$^2_2$, and —OR$^3$, all except H are optionally substituted; or together with X forms a cyclic group including aryl, cyclic alkyl, and heterocyclic;

R$^1$ is independently selected from the group consisting of —H, alkyl, aryl, alicyclic where the cyclic moiety contains a carbonate or thiocarbonate, —C(R$^2$)$_2$-aryl, alkylaryl, —C(R$^2$)$_2$OOC(O)NR$^2_2$, —NR$^2$—C(O)—R$^3$, —C(R$^2$)$_2$—OC(O)R$^3$, C(R$^2$)$_2$—O—C(O)OR$^3$, —C(R 2)$_2$OC(O)SR$^3$, alkyl-S—C(O)R$^3$, alkyl-S—S-alkylhydroxy, and alkyl-S—S—S-alkylhydroxy, or together R$^1$ and R$^1$ are -alkyl-S—S-alkyl to form a cyclic group, or together R$^1$ and R$^1$ are

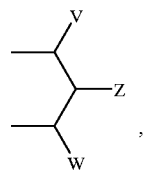

wherein

V and W are independently selected from the group consisting of hydrogen, aryl, substituted aryl, heteroaryl, substituted heteroaryl, 1-alkenyl, 1-alkynyl, and —R$^9$; or together V and Z are connected to form a cyclic group containing 3–5 atoms, optionally 1 heteroatom, substituted with hydroxy, acyloxy, alkoxycarboxy, or aryloxycarboxy attached to a carbon atom that is three atoms from an oxygen attached to the phosphorus; or together V and W are connected to form a cyclic group containing 3 carbon atoms substituted with hydroxy, acyloxy, alkoxycarboxy, alkylthiocarboxy, hydroxymethyl, and aryloxycarboxy attached to a carbon atom that is three atoms from an oxygen attached to the phosphorus;

Z is selected from the group consisting of —CH$_2$OH, —CH$_2$OCOR$^3$, —CH$_2$OC(O)SR$^3$, —CH$_2$OCO$_2$R$^3$, —SR$^3$, —S(O)R$^3$, —CH$_2$N$_3$, —CH$_2$NR 2$_2$, —CH$_2$Ar, —CH(Ar)OH, —CH(CH=CR$^2$R$^2$)OH, CH(C≡CR$^2$)OH, and —R$^2$;

with the provisos that:
a) V, Z, W are not all —H; and
b) when Z is —R$^2$, then at least one of V and W is not —H or —R$^9$;

R$^2$ is selected from the group consisting of R$^3$ and —H;

R$^3$ is selected from the group consisting of alkyl, aryl, alicyclic, and aralkyl;

R$^4$ is independently selected from the group consisting of —H, lower alkyl, lower alicyclic, lower aralkyl, and lower aryl;

R$^5$ is selected from the group consisting of lower alkyl, lower aryl, lower aralkyl, and lower alicyclic;

R$^5$ is independently selected from the group consisting of —H, and lower alkyl;

R$^7$ is independently selected from the group consisting of —H, lower alkyl, lower alicyclic, lower aralkyl, lower aryl, and —C(O)R$^{10}$;

R$^8$ is independently selected from the group consisting of —H, lower alkyl, lower aralkyl, lower aryl, lower alicyclic, —C(O)R$^{10}$, or together said R$^8$ groups form a bidentate alkyl;

R$^9$ is selected from the group consisting of alkyl, aralkyl, and alicyclic;

R$^{10}$ is selected from the group consisting of —H, lower alkyl, —NH$_2$, lower aryl, and lower perhaloalkyl;

R$^{11}$ is selected from the group consisting of alkyl, aryl, —OH, —NH$_2$ and —OR$^3$; and pharmaceutically acceptable prodrugs and salts thereof.

45. A method of treating an animal with excess glycogen storage disease, comprising administering to said animal in need thereof a therapeutically effective amount of a fructose-1,6-bisphosphatase inhibitor which binds to the AMP site of FBPase wherein said inhibitor is a compound of formula (1):

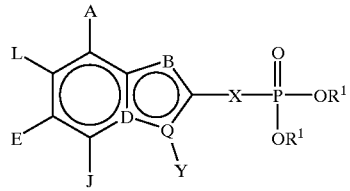

wherein:

B is selected from the group consisting of—NH—, and —CH=;

D is

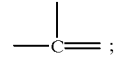

Q is selected from the group consisting of —C= and —N— with the proviso that when B is —NH— then Q is —C= and D is

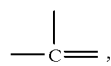

and when B is —CH= then Q is

and D is —C=;

A, E, and L are selected from the group consisting of —NR$^8{}_2$, —NO$_2$, —H, —OR$^7$, —SR$^7$, —C(O)NR$^4{}_2$, halo, —COR$^{11}$, —SO$_2$R$^3$, guanidine, amidine, —NHSO$_2$R$^5$, —SO$_2$NR$^4{}_2$, —CN, sulfoxide, perhaloacyl, perhaloalkyl, perhaloalkoxy, C1–C5 alkyl, C2–C5 alkenyl, C2–C5 alkynyl, and lower alicyclic, or together A and L form a cyclic group, or together L and E form a cyclic group, or together E and J form a cyclic group including aryl, cyclic alkyl, and heterocyclic;

J is selected from the group consisting of —NR$^8{}_2$, —NO$_2$, —H, —OR$^7$, —SR$^7$, —C(O)NR$^4{}_2$, halo, —C(O)R$^{11}$, —CN, sulfonyl, sulfoxide, perhaloalkyl, hydroxyalkyl, perhaloalkoxy, alkyl, haloalkyl, aminoalkyl, alkenyl, alkynyl, alicyclic, aryl, and aralkyl, or together with Y forms a cyclic group including aryl, cyclic alkyl and heterocyclic alkyl;

X is selected from the group consisting of alkylamino, alkyl(hydroxy), alkyl(carboxyl), alkyl(phosphonate), alkyl, alkenyl, alkynyl, alkyl(sulfonate), aryl, heteroaryl, carbonylalkyl, 1,1-dihaloalkyl, aminocarbonylamino, alkylaminoalkyl, alkoxyalkyl, alkylthioalkyl, alkylthio, alkylaminocarbonyl, alkylcarbonylamino, alicyclic, aralkyl, and alkylaryl, all optionally substituted; or together with Y forms a cyclic group including aryl, cyclic alkyl, and heterocyclic;

Y is selected from the group consisting of -H, alkyl, alkenyl, alkynyl, aryl, alicyclic, aralkyl, aryloxyalkyl, alkoxyalkyl, —C(O)R$^3$, —S(O)2R$^3$, —C(O)—OR$^3$, —CONHR$^3$, —NR$^2{}_2$, and —OR$^3$, all except H are optionally substituted; or together with X forms a cyclic group including aryl, cyclic alkyl, and heterocyclic;

R$^1$ is independently selected from the group consisting of —H, alkyl, aryl, alicyclic where the cyclic moiety contains a carbonate or thiocarbonate, —C(R$^2$)$_2$-aryl, alkylaryl, —C(R$^2$)$_2$OC(O)NR$^2{}_2$, —NR$^2$—C(O)—R$^3$, —C(R$^2$)$_2$—OC(O)R$^3$, C(R$^2$)$_2$—O—C(O)OR$^3$, —C(R$^2$)$_2$OC(O)SR$^3$, alkyl-S—C(O)R$^3$, alkyl-S—S-alkylhydroxy, and alkyl-S—S—S-alkylhydroxy, or together R$^1$ and R$^1$ are -alkyl-S—S-alkyl to form a cyclic group, or together R$^1$ and R$^1$ are

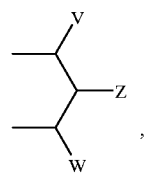

wherein

V and W are independently selected from the group consisting of hydrogen, aryl, substituted aryl, heteroaryl, substituted heteroaryl, 1-alkenyl, 1-alkynyl, and —R$^9$; or together V and Z are connected to form a cyclic group containing 3–5 atoms, optionally 1 heteroatom, substituted with hydroxy, acyloxy, alkoxycarboxy, or aryloxycarboxy attached to a carbon atom that is three atoms from an oxygen attached to the phosphorus; or together V and W are connected to form a cyclic group containing 3 carbon atoms substituted with hydroxy, acyloxy, alkoxycarboxy, alkylthiocarboxy, hydroxymethyl, and aryloxycarboxy attached to a carbon atom that is three atoms from an oxygen attached to the phosphorus;

Z is selected from the group consisting of —CH$_2$OH, —CH$_2$OCOR$^3$, —CH$_2$OC(O)SR$^3$, —CH$_2$OCO$_2$R$^3$, —SR$^3$, —S(O)R$^3$, —CH$_2$N$_3$, —CH$_2$NR$^2{}_2$, —CH$_2$Ar, —CH(Ar)OH, —CH(CH=CR$^2$R$^2$)OH, —CH(C≡CR$^2$)OH, and —R$^2$;

with the provisos that:

a) V, Z, W are not all —H; and b) when Z is —R$^2$, then at least one of V and W is not —H or —R$^9$;

R$^2$ is selected from the group consisting of R$^3$ and —H;

R$^3$ is selected from the group consisting of alkyl, aryl, alicyclic, and aralkyl;

R$^4$ is independently selected from the group consisting of —H, lower alkyl, lower alicyclic, lower aralkyl, and lower aryl;

R$^5$ is selected from the group consisting of lower alkyl, lower aryl, lower aralkyl, and lower alicyclic;

R$^6$ is independently selected from the group consisting of —H, and lower alkyl;

R$^7$ is independently selected from the group consisting of —H, lower alkyl, lower alicyclic, lower aralkyl, lower aryl, and —C(O)R$^{10}$;

R$^8$ is independently selected from the group consisting of —H, lower alkyl, lower aralkyl, lower aryl, lower alicyclic, —C(O)R$^{10}$, or together said R$^8$ groups form a bidentate alkyl;

R$^9$ is selected from the group consisting of alkyl, aralkyl, and alicyclic;

R$^{10}$ is selected from the group consisting of —H, lower alkyl, —NH$_2$, lower aryl, and lower perhaloalkyl;

R$^{11}$ is selected from the group consisting of alkyl, aryl, —OH, —NH$_2$ and —OR$^3$; and pharmaceutically acceptable prodrugs and salts thereof.

46. The methods of claims 40, 41, 42, 43, 44 or 45 wherein said compounds are administered orally.

47. The methods of claims 40, 41, 42, 43, 44 or 45 wherein

A, L, and E are independently selected from the group consisting of —NR$^8{}_2$, —H, hydroxy, halogen lower alkoxy, lower alkyl and lower perhaloalkyl;

J is selected from the group consisting of —H, halogen, lower alkyl, lower hydroxy alkyl, —NR$^8_2$, lower R$^8_2$N-alkyl, lower haloalkyl, lower alkenyl, alicyclic, and aryl;

X is selected from the group consisting of aryl, heteroaryl, alkoxyalkyl, alkyl, alkylthio, 1,1-dihaloalkyl, carbonylalkyl, alkyl(hydroxy), alkyl(sulfonate), alkylaminocarbonyl, and alkylcarbonylamino;

and each R$^4$ and R$^7$ is independently selected from the group consisting of —H and lower alkyl;

with the provisos that:

a) R$^1$ is not lower alkyl of 1–4 carbon atoms;

b) X is not alkylamine and alkylaminoalkyl substituted with phosphonic esters or acids; and c) X is not aryl, and alkylaryl linked 1,4 through a 6-membered aromatic ring.

* * * * *